United States Patent
Root et al.

(10) Patent No.: US 10,765,552 B2
(45) Date of Patent: Sep. 8, 2020

(54) COOLING CUP APPLICATORS WITH CONTOURED HEADS AND LINER ASSEMBLIES

(71) Applicant: Zeltiq Aesthetics, Inc., Pleasanton, CA (US)

(72) Inventors: Austin Root, Pleasanton, CA (US); William Pennybacker, Livermore, CA (US); George Frangineas, Fremont, CA (US); Clive Heke, Pleasanton, CA (US); Leonard C. DeBenedictis, Dublin, CA (US)

(73) Assignee: Zeltiq Aesthetics, Inc., Pleasanton, CA (US)

(*) Notice: Subject to any disclaimer, the term of this patent is extended or adjusted under 35 U.S.C. 154(b) by 474 days.

(21) Appl. No.: 15/435,179

(22) Filed: Feb. 16, 2017

(65) Prior Publication Data
US 2017/0239079 A1 Aug. 24, 2017

Related U.S. Application Data

(60) Provisional application No. 62/297,054, filed on Feb. 18, 2016.

(51) Int. Cl.
*A61F 7/00* (2006.01)
*A61F 7/02* (2006.01)

(52) U.S. Cl.
CPC ...... *A61F 7/007* (2013.01); *A61F 2007/0054* (2013.01); *A61F 2007/0075* (2013.01);
(Continued)

(58) Field of Classification Search
CPC combination set(s) only.
See application file for complete search history.

(56) References Cited

U.S. PATENT DOCUMENTS

| 681,806 A | 9/1901 | Mignault et al. |
| 889,810 A | 6/1908 | Robinson et al. |

(Continued)

FOREIGN PATENT DOCUMENTS

| AU | 2011253768 A1 | 6/2012 |
| CA | 2441489 A1 | 3/2005 |

(Continued)

OTHER PUBLICATIONS

Aguilar et al., "Modeling Cryogenic Spray Temperature and Evaporation Rate Based on Single-Droplet Analysis," Eighth International Conference on Liquid Atomization and Spray Systems, Pasadena, CA, USA, Jul. 2000, 7 pages.

(Continued)

*Primary Examiner* — Joseph A Stoklosa
*Assistant Examiner* — Adam J Avigan
(74) *Attorney, Agent, or Firm* — Perkins Coie LLP

(57) ABSTRACT

Systems for treating a subject's tissue can include a thermally conductive cup, a sealing member, and/or a liner assembly. The systems can include an applicator capable of being reconfigured for a particular treatment site. Components of the applicator can be replaced to achieve a desired configuration. The replaceable components can include contoured heads, liners, and/or sensors. The applicator can draw a vacuum to install various components and/or draw tissue into the applicator. The applicator can cool and/or heat the tissue to affect targeted tissue.

2 Claims, 17 Drawing Sheets

(52) U.S. Cl.
CPC . *A61F 2007/0093* (2013.01); *A61F 2007/029* (2013.01); *A61F 2007/0239* (2013.01)

(56) References Cited

U.S. PATENT DOCUMENTS

| | | | |
|---|---|---|---|
| 2,516,491 A | 7/1950 | Swastek |
| 2,521,780 A | 9/1950 | Dodd et al. |
| 2,726,658 A | 12/1955 | Chessey |
| 2,766,619 A | 10/1956 | Tribus et al. |
| 2,851,602 A | 9/1958 | Cramwinckel et al. |
| 3,093,135 A | 6/1963 | Hirschhorn |
| 3,132,688 A | 5/1964 | Nowak |
| 3,133,539 A | 5/1964 | Eidus et al. |
| 3,282,267 A | 11/1966 | Eidus |
| 3,502,080 A | 3/1970 | Hirschhorn |
| 3,566,871 A | 3/1971 | Richter et al. |
| 3,587,577 A | 6/1971 | Zubkov et al. |
| 3,591,645 A | 7/1971 | Selwitz |
| 3,703,897 A | 11/1972 | Mack et al. |
| 3,710,784 A | 1/1973 | Taylor |
| 3,786,814 A | 1/1974 | Armao |
| 3,827,436 A | 8/1974 | Andera et al. |
| 3,942,519 A | 3/1976 | Shock |
| 3,948,269 A | 4/1976 | Zimmer |
| 3,986,385 A | 10/1976 | Johnston et al. |
| 3,993,053 A | 11/1976 | Grossan |
| 4,002,221 A | 1/1977 | Buchalter |
| 4,026,299 A | 5/1977 | Sauder |
| 4,140,130 A | 2/1979 | Storm |
| 4,149,529 A | 4/1979 | Copeland et al. |
| 4,178,429 A | 12/1979 | Scheffer |
| 4,202,336 A | 5/1980 | Van Gerven |
| 4,266,043 A | 5/1981 | Fujii et al. |
| 4,269,068 A | 5/1981 | Molina |
| 4,381,009 A | 4/1983 | Del Bon |
| 4,396,011 A | 8/1983 | Mack et al. |
| 4,459,854 A | 7/1984 | Richardson et al. |
| 4,470,263 A | 9/1984 | Lehovec et al. |
| 4,483,341 A | 11/1984 | Witteles |
| 4,528,979 A | 7/1985 | Marchenko et al. |
| 4,531,524 A | 7/1985 | Mioduski |
| 4,548,212 A | 10/1985 | Leung |
| 4,555,313 A | 11/1985 | Duchane et al. |
| 4,585,002 A | 4/1986 | Kissin |
| 4,603,076 A | 7/1986 | Bowditch et al. |
| 4,614,191 A | 9/1986 | Perler et al. |
| 4,644,955 A | 2/1987 | Mioduski |
| 4,664,110 A | 5/1987 | Schanzlin |
| 4,700,701 A | 10/1987 | Montaldi |
| 4,718,429 A | 1/1988 | Smidt |
| 4,741,338 A | 5/1988 | Miyamae |
| 4,764,463 A | 8/1988 | Mason et al. |
| 4,802,475 A | 2/1989 | Weshahy |
| 4,832,022 A | 5/1989 | Tjulkov et al. |
| 4,846,176 A | 7/1989 | Golden |
| 4,850,340 A | 7/1989 | Onishi |
| 4,869,250 A | 9/1989 | Bitterly |
| 4,880,564 A | 11/1989 | Abel et al. |
| 4,905,697 A | 3/1990 | Heggs et al. |
| 4,906,463 A | 3/1990 | Cleary et al. |
| 4,930,317 A | 6/1990 | Klein |
| 4,935,345 A | 6/1990 | Guilbeau et al. |
| 4,961,422 A | 10/1990 | Marchosky et al. |
| 4,962,761 A | 10/1990 | Golden |
| 4,990,144 A | 2/1991 | Blott et al. |
| 5,007,433 A | 4/1991 | Hermsdoerffer et al. |
| 5,018,521 A | 5/1991 | Campbell et al. |
| 5,024,650 A | 6/1991 | Hagiwara et al. |
| 5,065,752 A | 11/1991 | Sessions et al. |
| 5,069,208 A | 12/1991 | Noppel et al. |
| 5,084,671 A | 1/1992 | Miyata et al. |
| 5,108,390 A | 4/1992 | Potocky et al. |
| 5,119,674 A | 6/1992 | Nielsen |
| 5,139,496 A | 8/1992 | Hed |
| 5,143,063 A | 9/1992 | Fellner |
| 5,148,804 A | 9/1992 | Hill et al. |
| 5,158,070 A | 10/1992 | Dory |
| 5,160,312 A | 11/1992 | Voelkel |
| 5,169,384 A | 12/1992 | Bosniak et al. |
| 5,197,466 A | 3/1993 | Marchosky et al. |
| 5,207,674 A | 5/1993 | Hamilton |
| 5,221,726 A | 6/1993 | Dabi et al. |
| 5,264,234 A | 11/1993 | Windhab et al. |
| 5,277,030 A | 1/1994 | Miller |
| 5,314,423 A | 5/1994 | Seney et al. |
| 5,327,886 A | 7/1994 | Chiu |
| 5,330,745 A | 7/1994 | Mcdow et al. |
| 5,333,460 A | 8/1994 | Lewis et al. |
| 5,334,131 A | 8/1994 | Omandam et al. |
| 5,336,616 A | 8/1994 | Livesey et al. |
| 5,339,541 A | 8/1994 | Owens |
| 5,342,617 A | 8/1994 | Gold et al. |
| 5,351,677 A | 10/1994 | Kami et al. |
| 5,358,467 A | 10/1994 | Milstein et al. |
| 5,362,966 A | 11/1994 | Rosenthal et al. |
| 5,363,347 A | 11/1994 | Nguyen |
| 5,372,608 A | 12/1994 | Johnson |
| 5,386,837 A | 2/1995 | Sterzer |
| 5,411,541 A | 5/1995 | Bell et al. |
| 5,427,772 A | 6/1995 | Hagan et al. |
| 5,433,717 A | 7/1995 | Rubinsky et al. |
| 5,456,703 A | 10/1995 | Beeuwkes, III et al. |
| 5,472,416 A | 12/1995 | Blugerman et al. |
| 5,486,207 A | 1/1996 | Mahawili |
| 5,497,596 A | 3/1996 | Zatkulak |
| 5,501,655 A | 3/1996 | Rolt et al. |
| 5,505,726 A | 4/1996 | Meserol |
| 5,505,730 A | 4/1996 | Edwards et al. |
| 5,507,790 A | 4/1996 | Weiss |
| 5,514,105 A | 5/1996 | Goodman, Jr. et al. |
| 5,514,170 A | 5/1996 | Mauch |
| 5,516,505 A | 5/1996 | Mcdow |
| 5,531,742 A | 7/1996 | Barken |
| 5,562,604 A | 10/1996 | Yablon et al. |
| 5,571,801 A | 11/1996 | Segall et al. |
| 5,575,812 A | 11/1996 | Owens et al. |
| 5,603,221 A | 2/1997 | Maytal |
| 5,628,769 A | 5/1997 | Saringer |
| 5,634,890 A | 6/1997 | Morris |
| 5,634,940 A | 6/1997 | Panyard |
| 5,647,051 A | 7/1997 | Neer |
| 5,647,868 A | 7/1997 | Chinn |
| 5,650,450 A | 7/1997 | Lovette et al. |
| 5,651,773 A | 7/1997 | Perry et al. |
| 5,654,279 A | 8/1997 | Rubinsky et al. |
| 5,654,546 A | 8/1997 | Lindsay et al. |
| 5,660,836 A | 8/1997 | Knowlton et al. |
| 5,665,053 A | 9/1997 | Jacobs |
| 5,672,172 A | 9/1997 | Zupkas |
| 5,700,284 A | 12/1997 | Owens et al. |
| 5,725,483 A | 3/1998 | Podolsky |
| 5,733,280 A | 3/1998 | Avitall |
| 5,741,248 A | 4/1998 | Stern et al. |
| 5,746,702 A | 5/1998 | Gelfgat et al. |
| 5,746,736 A | 5/1998 | Tankovich |
| 5,755,663 A | 5/1998 | Larsen et al. |
| 5,755,753 A | 5/1998 | Knowlton et al. |
| 5,755,755 A | 5/1998 | Panyard |
| 5,759,182 A | 6/1998 | Varney et al. |
| 5,759,764 A | 6/1998 | Polovina et al. |
| 5,769,879 A | 6/1998 | Richards et al. |
| 5,785,955 A | 7/1998 | Fischer |
| 5,792,080 A | 8/1998 | Ookawa et al. |
| 5,800,490 A | 9/1998 | Patz et al. |
| 5,814,040 A | 9/1998 | Nelson et al. |
| 5,817,050 A | 10/1998 | Klein et al. |
| 5,817,149 A | 10/1998 | Owens et al. |
| 5,817,150 A | 10/1998 | Owens et al. |
| 5,830,208 A | 11/1998 | Muller et al. |
| 5,833,685 A | 11/1998 | Tortal et al. |
| 5,844,013 A | 12/1998 | Kenndoff et al. |
| 5,865,841 A | 2/1999 | Kolen et al. |
| 5,871,524 A | 2/1999 | Knowlton |
| 5,871,526 A | 2/1999 | Gibbs et al. |

(56) References Cited

U.S. PATENT DOCUMENTS

| | | |
|---|---|---|
| 5,885,211 A | 3/1999 | Eppstein et al. |
| 5,891,617 A | 4/1999 | Watson et al. |
| 5,895,418 A | 4/1999 | Saringer |
| 5,901,707 A | 5/1999 | Goncalves |
| 5,902,256 A | 5/1999 | Benaron |
| 5,919,219 A | 7/1999 | Knowlton et al. |
| 5,944,748 A | 8/1999 | Mager et al. |
| 5,948,011 A | 9/1999 | Knowlton et al. |
| 5,954,680 A | 9/1999 | Augustine et al. |
| 5,964,092 A | 10/1999 | Tozuka et al. |
| 5,964,749 A | 10/1999 | Eckhouse et al. |
| 5,967,976 A | 10/1999 | Larsen et al. |
| 5,980,561 A | 11/1999 | Kolen et al. |
| 5,986,167 A | 11/1999 | Arteman et al. |
| 5,989,286 A | 11/1999 | Owens et al. |
| 5,997,530 A | 12/1999 | Nelson et al. |
| 6,017,337 A | 1/2000 | Pira |
| 6,023,932 A | 2/2000 | Johnston |
| 6,032,675 A | 3/2000 | Rubinsky |
| 6,039,694 A | 3/2000 | Larson et al. |
| 6,041,787 A | 3/2000 | Rubinsky |
| 6,047,215 A | 4/2000 | McClure et al. |
| 6,049,927 A | 4/2000 | Thomas et al. |
| 6,051,159 A | 4/2000 | Hao et al. |
| 6,071,239 A | 6/2000 | Cribbs et al. |
| 6,074,415 A | 6/2000 | Der Ovanesian |
| 6,093,230 A | 7/2000 | Johnson et al. |
| 6,102,885 A | 8/2000 | Bass |
| 6,104,952 A | 8/2000 | Tu et al. |
| 6,104,959 A | 8/2000 | Spertell et al. |
| 6,106,517 A | 8/2000 | Zupkas |
| 6,113,558 A | 9/2000 | Rosenschein et al. |
| 6,113,559 A | 9/2000 | Klopotek |
| 6,113,626 A | 9/2000 | Clifton et al. |
| 6,120,519 A | 9/2000 | Weber et al. |
| 6,139,544 A | 10/2000 | Mikus et al. |
| 6,150,148 A | 11/2000 | Nanda et al. |
| 6,151,735 A | 11/2000 | Koby et al. |
| 6,152,952 A | 11/2000 | Owens et al. |
| 6,171,301 B1 | 1/2001 | Nelson et al. |
| 6,180,867 B1 | 1/2001 | Hedengren et al. |
| 6,226,996 B1 | 5/2001 | Weber et al. |
| 6,241,753 B1 | 6/2001 | Knowlton |
| 6,264,649 B1 | 7/2001 | Whitcroft et al. |
| 6,273,884 B1 | 8/2001 | Altshuler et al. |
| 6,290,988 B1 | 9/2001 | Van Vilsteren et al. |
| 6,311,090 B1 | 10/2001 | Knowlton |
| 6,311,497 B1 | 11/2001 | Chung |
| 6,312,453 B1 | 11/2001 | Stefanile et al. |
| 6,350,276 B1 | 2/2002 | Knowlton |
| 6,354,297 B1 | 3/2002 | Eiseman |
| 6,357,907 B1 | 3/2002 | Cleveland et al. |
| 6,375,673 B1 | 4/2002 | Clifton et al. |
| 6,377,854 B1 | 4/2002 | Knowlton |
| 6,377,855 B1 | 4/2002 | Knowlton |
| 6,381,497 B1 | 4/2002 | Knowlton |
| 6,381,498 B1 | 4/2002 | Knowlton |
| 6,387,380 B1 | 5/2002 | Knowlton |
| 6,401,722 B1 | 6/2002 | Krag |
| 6,405,090 B1 | 6/2002 | Knowlton |
| 6,413,255 B1 | 7/2002 | Stern |
| 6,425,912 B1 | 7/2002 | Knowlton |
| 6,426,445 B1 | 7/2002 | Young et al. |
| 6,430,446 B1 | 8/2002 | Knowlton |
| 6,430,956 B1 | 8/2002 | Haas et al. |
| 6,438,424 B1 | 8/2002 | Knowlton |
| 6,438,954 B1 | 8/2002 | Goetz et al. |
| 6,438,964 B1 | 8/2002 | Giblin |
| 6,453,202 B1 | 9/2002 | Knowlton |
| 6,458,888 B1 | 10/2002 | Hood et al. |
| 6,461,378 B1 | 10/2002 | Knowlton |
| 6,470,216 B1 | 10/2002 | Knowlton |
| 6,471,693 B1 | 10/2002 | Carroll et al. |
| 6,475,211 B2 | 11/2002 | Chess et al. |
| 6,478,811 B1 | 11/2002 | Dobak, III et al. |
| 6,494,844 B1 | 12/2002 | Van Bladel et al. |
| 6,497,721 B2 | 12/2002 | Ginsburg et al. |
| 6,508,831 B1 | 1/2003 | Kushnir |
| 6,514,244 B2 | 2/2003 | Pope et al. |
| 6,519,964 B2 | 2/2003 | Bieberich |
| 6,523,354 B1 | 2/2003 | Tolbert |
| 6,527,765 B2 | 3/2003 | Kelman et al. |
| 6,527,798 B2 | 3/2003 | Ginsburg et al. |
| 6,544,248 B1 | 4/2003 | Bass |
| 6,547,811 B1 | 4/2003 | Becker et al. |
| 6,548,297 B1 | 4/2003 | Kuri-Harcuch et al. |
| 6,551,255 B2 | 4/2003 | Van Bladel et al. |
| 6,551,341 B2 | 4/2003 | Boylan et al. |
| 6,551,348 B1 | 4/2003 | Blalock et al. |
| 6,551,349 B2 | 4/2003 | Lasheras et al. |
| 6,569,189 B1 | 5/2003 | Augustine et al. |
| 6,585,652 B2 | 7/2003 | Lang et al. |
| 6,592,577 B2 | 7/2003 | Abboud et al. |
| 6,605,080 B1 | 8/2003 | Altshuler et al. |
| 6,607,498 B2 | 8/2003 | Eshel |
| 6,620,187 B2 | 9/2003 | Carson et al. |
| 6,620,188 B1 | 9/2003 | Ginsburg et al. |
| 6,620,189 B1 | 9/2003 | Machold et al. |
| 6,623,430 B1 | 9/2003 | Slayton et al. |
| 6,626,854 B2 | 9/2003 | Friedman et al. |
| 6,632,219 B1 | 10/2003 | Baranov et al. |
| 6,635,053 B1 | 10/2003 | Lalonde et al. |
| 6,643,535 B2 | 11/2003 | Damasco et al. |
| 6,645,162 B2 | 11/2003 | Friedman et al. |
| 6,645,229 B2 | 11/2003 | Matsumura et al. |
| 6,645,232 B2 | 11/2003 | Carson |
| 6,648,904 B2 | 11/2003 | Altshuler et al. |
| 6,656,208 B2 | 12/2003 | Grahn et al. |
| 6,660,027 B2 | 12/2003 | Gruszecki et al. |
| 6,662,054 B2 | 12/2003 | Kreindel et al. |
| 6,682,550 B2 | 1/2004 | Clifton et al. |
| 6,685,731 B2 | 2/2004 | Kushnir et al. |
| 6,694,170 B1 | 2/2004 | Mikus et al. |
| 6,695,874 B2 | 2/2004 | Machold et al. |
| 6,697,670 B2 | 2/2004 | Chornenky |
| 6,699,237 B2 | 3/2004 | Weber et al. |
| 6,699,266 B2 | 3/2004 | Lachenbruch et al. |
| 6,699,267 B2 | 3/2004 | Voorhees et al. |
| 6,718,785 B2 | 4/2004 | Bieberich |
| 6,741,895 B1 | 5/2004 | Gafni et al. |
| 6,743,222 B2 | 6/2004 | Durkin et al. |
| 6,746,474 B2 | 6/2004 | Saadat |
| 6,749,624 B2 | 6/2004 | Knowlton |
| 6,753,182 B1 | 6/2004 | Kadkade et al. |
| 6,764,493 B1 | 7/2004 | Weber et al. |
| 6,764,502 B2 | 7/2004 | Bieberich |
| 6,789,545 B2 | 9/2004 | Littrup et al. |
| 6,795,728 B2 | 9/2004 | Chornenky et al. |
| 6,820,961 B2 | 11/2004 | Johnson |
| 6,821,274 B2 | 11/2004 | McHale et al. |
| 6,840,955 B2 | 1/2005 | Ein |
| 6,849,075 B2 | 2/2005 | Bertolero et al. |
| 6,878,144 B2 | 4/2005 | Altshuler et al. |
| 6,889,090 B2 | 5/2005 | Kreindel |
| 6,892,099 B2 | 5/2005 | Jaafar et al. |
| 6,904,956 B2 | 6/2005 | Noel |
| 6,918,903 B2 | 7/2005 | Bass |
| 6,927,316 B1 | 8/2005 | Faries, Jr. et al. |
| 6,942,022 B2 | 9/2005 | Blangetti et al. |
| 6,945,942 B2 | 9/2005 | Van Bladel et al. |
| 6,948,903 B2 | 9/2005 | Ablabutyan et al. |
| 6,969,399 B2 | 11/2005 | Schock et al. |
| 7,005,558 B1 | 2/2006 | Johansson et al. |
| 7,006,874 B2 | 2/2006 | Knowlton et al. |
| 7,022,121 B2 | 4/2006 | Stern et al. |
| 7,037,326 B2 | 5/2006 | Lee |
| 7,054,685 B2 | 5/2006 | Dimmer et al. |
| 7,060,061 B2 | 6/2006 | Altshuler et al. |
| 7,077,858 B2 | 7/2006 | Fletcher et al. |
| 7,081,111 B2 | 7/2006 | Svaasand et al. |
| 7,083,612 B2 | 8/2006 | Littrup et al. |
| 7,096,204 B1 | 8/2006 | Chen et al. |
| 7,112,712 B1 | 9/2006 | Ancell |
| 7,115,123 B2 | 10/2006 | Knowlton et al. |

(56) References Cited

U.S. PATENT DOCUMENTS

| | | |
|---|---|---|
| 7,141,049 B2 | 11/2006 | Stern et al. |
| 7,183,360 B2 | 2/2007 | Daniel et al. |
| 7,189,252 B2 | 3/2007 | Krueger |
| 7,192,426 B2 | 3/2007 | Baust et al. |
| 7,204,832 B2 | 4/2007 | Altshuler et al. |
| 7,220,778 B2 | 5/2007 | Anderson et al. |
| 7,229,436 B2 | 6/2007 | Stern et al. |
| 7,258,674 B2 | 8/2007 | Cribbs et al. |
| 7,267,675 B2 | 9/2007 | Stern et al. |
| 7,276,058 B2 | 10/2007 | Altshuler et al. |
| 7,318,821 B2 | 1/2008 | Lalonde et al. |
| 7,331,951 B2 | 2/2008 | Eshel et al. |
| 7,347,855 B2 | 3/2008 | Eshel et al. |
| 7,367,341 B2 | 5/2008 | Anderson et al. |
| 7,532,201 B2 | 5/2009 | Quistgaard et al. |
| 7,572,268 B2 | 8/2009 | Babaev |
| 7,604,632 B2 | 10/2009 | Howlett et al. |
| 7,613,523 B2 | 11/2009 | Eggers et al. |
| 7,615,016 B2 | 11/2009 | Barthe et al. |
| 7,713,266 B2 | 5/2010 | Elkins et al. |
| 7,780,656 B2 | 8/2010 | Tankovich |
| 7,799,018 B2 | 9/2010 | Goulko |
| 7,824,437 B1 | 11/2010 | Saunders |
| 7,828,831 B1 | 11/2010 | Tanhehco et al. |
| 7,850,683 B2 | 12/2010 | Elkins et al. |
| 7,854,754 B2 | 12/2010 | Ting et al. |
| 7,862,558 B2 | 1/2011 | Elkins et al. |
| RE42,277 E | 4/2011 | Jaafar et al. |
| 7,938,824 B2 | 5/2011 | Chornenky et al. |
| 7,959,657 B1 | 6/2011 | Harsy et al. |
| 7,963,959 B2 | 6/2011 | Da Silva et al. |
| 7,967,763 B2 | 6/2011 | Deem et al. |
| 7,993,330 B2 | 8/2011 | Goulko |
| 7,998,137 B2 | 8/2011 | Elkins et al. |
| RE42,835 E | 10/2011 | Chornenky et al. |
| RE43,009 E | 12/2011 | Chornenky et al. |
| 8,133,180 B2 | 3/2012 | Slayton et al. |
| 8,133,191 B2 | 3/2012 | Rosenberg et al. |
| 8,192,474 B2 | 6/2012 | Levinson |
| 8,246,611 B2 | 8/2012 | Paithankar et al. |
| 8,275,442 B2 | 9/2012 | Allison |
| 8,285,390 B2 | 10/2012 | Levinson et al. |
| 8,333,700 B1 | 12/2012 | Barthe et al. |
| 8,337,539 B2 | 12/2012 | Ting et al. |
| 8,366,622 B2 | 2/2013 | Slayton et al. |
| 8,372,130 B2 | 2/2013 | Young et al. |
| 8,397,518 B1 | 3/2013 | Vistakula et al. |
| 8,414,631 B2 | 4/2013 | Quisenberry et al. |
| 8,433,400 B2 | 4/2013 | Prushinskaya et al. |
| 8,506,486 B2 | 8/2013 | Slayton et al. |
| 8,523,775 B2 | 9/2013 | Barthe et al. |
| 8,523,791 B2 | 9/2013 | Castel |
| 8,523,927 B2 | 9/2013 | Levinson et al. |
| 8,535,228 B2 | 9/2013 | Slayton et al. |
| 8,603,073 B2 | 12/2013 | Allison |
| 8,636,665 B2 | 1/2014 | Slayton et al. |
| 8,641,622 B2 | 2/2014 | Barthe et al. |
| 8,663,112 B2 | 3/2014 | Slayton et al. |
| 8,672,848 B2 | 3/2014 | Slayton et al. |
| 8,676,332 B2 | 3/2014 | Fahey |
| 8,690,778 B2 | 4/2014 | Slayton et al. |
| 8,690,779 B2 | 4/2014 | Slayton et al. |
| 8,690,780 B2 | 4/2014 | Slayton et al. |
| 8,702,774 B2 | 4/2014 | Baker et al. |
| 8,758,215 B2 | 6/2014 | Legendre et al. |
| 8,764,693 B1 | 7/2014 | Graham et al. |
| 8,834,547 B2 | 9/2014 | Anderson et al. |
| 9,861,520 B2 | 1/2018 | Baker et al. |
| 2001/0005791 A1 | 6/2001 | Ginsburg et al. |
| 2001/0007952 A1 | 7/2001 | Shimizu |
| 2001/0023364 A1 | 9/2001 | Ahn |
| 2001/0031459 A1 | 10/2001 | Fahy et al. |
| 2001/0039439 A1 | 11/2001 | Elkins et al. |
| 2001/0045104 A1 | 11/2001 | Bailey, Sr. et al. |
| 2001/0047196 A1 | 11/2001 | Ginsburg et al. |
| 2002/0026226 A1 | 2/2002 | Ein |
| 2002/0032473 A1 | 3/2002 | Kushnir et al. |
| 2002/0042607 A1 | 4/2002 | Palmer et al. |
| 2002/0049483 A1 | 4/2002 | Knowlton |
| 2002/0058975 A1 | 5/2002 | Bieberich |
| 2002/0062142 A1 | 5/2002 | Knowlton |
| 2002/0068338 A1 | 6/2002 | Nanda et al. |
| 2002/0082668 A1 | 6/2002 | Ingman |
| 2002/0103520 A1 | 8/2002 | Latham |
| 2002/0107558 A1 | 8/2002 | Clifton et al. |
| 2002/0117293 A1 | 8/2002 | Campbell |
| 2002/0120315 A1 | 8/2002 | Furuno et al. |
| 2002/0128648 A1 | 9/2002 | Weber et al. |
| 2002/0151830 A1 | 10/2002 | Kahn |
| 2002/0151887 A1 | 10/2002 | Stern et al. |
| 2002/0156509 A1 | 10/2002 | Cheung |
| 2002/0188286 A1 | 12/2002 | Quijano et al. |
| 2002/0198518 A1 | 12/2002 | Mikus et al. |
| 2003/0032900 A1 | 2/2003 | Ella |
| 2003/0044764 A1 | 3/2003 | Soane et al. |
| 2003/0055414 A1 | 3/2003 | Altshuler et al. |
| 2003/0062040 A1 | 4/2003 | Lurie et al. |
| 2003/0069618 A1 | 4/2003 | Smith, III et al. |
| 2003/0077326 A1 | 4/2003 | Newton et al. |
| 2003/0077329 A1 | 4/2003 | Kipp et al. |
| 2003/0079488 A1 | 5/2003 | Bieberich |
| 2003/0100936 A1 | 5/2003 | Altshuler et al. |
| 2003/0109908 A1 | 6/2003 | Lachenbruch et al. |
| 2003/0109910 A1 | 6/2003 | Lachenbruch et al. |
| 2003/0109911 A1 | 6/2003 | Lachenbruch et al. |
| 2003/0109912 A1 | 6/2003 | Joye et al. |
| 2003/0114885 A1 | 6/2003 | Nova et al. |
| 2003/0120268 A1 | 6/2003 | Bertolero et al. |
| 2003/0125649 A1 | 7/2003 | McIntosh et al. |
| 2003/0187488 A1 | 10/2003 | Kreindel et al. |
| 2003/0199226 A1 | 10/2003 | Sommer et al. |
| 2003/0199859 A1 | 10/2003 | Altshuler et al. |
| 2003/0220594 A1 | 11/2003 | Halvorson et al. |
| 2003/0220635 A1 | 11/2003 | Knowlton et al. |
| 2003/0220674 A1 | 11/2003 | Anderson et al. |
| 2003/0236487 A1 | 12/2003 | Knowlton |
| 2004/0002705 A1 | 1/2004 | Knowlton et al. |
| 2004/0006328 A1 | 1/2004 | Anderson |
| 2004/0009936 A1 | 1/2004 | Tang et al. |
| 2004/0024437 A1 | 2/2004 | Machold et al. |
| 2004/0030332 A1 | 2/2004 | Knowlton et al. |
| 2004/0034341 A1 | 2/2004 | Altshuler et al. |
| 2004/0039312 A1 | 2/2004 | Hillstead et al. |
| 2004/0044384 A1 | 3/2004 | Leber et al. |
| 2004/0049178 A1 | 3/2004 | Abboud et al. |
| 2004/0073079 A1 | 4/2004 | Altshuler et al. |
| 2004/0074629 A1 | 4/2004 | Noel |
| 2004/0077977 A1 | 4/2004 | Ella et al. |
| 2004/0082886 A1 | 4/2004 | Timpson |
| 2004/0093042 A1 | 5/2004 | Altshuler et al. |
| 2004/0104012 A1 | 6/2004 | Zhou et al. |
| 2004/0106867 A1 | 6/2004 | Eshel et al. |
| 2004/0133251 A1 | 7/2004 | Altshuler et al. |
| 2004/0162596 A1 | 8/2004 | Altshuler et al. |
| 2004/0176667 A1 | 9/2004 | Mihai et al. |
| 2004/0186535 A1 | 9/2004 | Knowlton |
| 2004/0199226 A1 | 10/2004 | Shadduck |
| 2004/0206365 A1 | 10/2004 | Knowlton |
| 2004/0210214 A1 | 10/2004 | Knowlton |
| 2004/0210287 A1 | 10/2004 | Greene |
| 2004/0215294 A1 | 10/2004 | Littrup et al. |
| 2004/0249427 A1 | 12/2004 | Nabilsi et al. |
| 2004/0259855 A1 | 12/2004 | Anderson et al. |
| 2004/0260209 A1 | 12/2004 | Ella et al. |
| 2004/0260210 A1 | 12/2004 | Ella et al. |
| 2004/0260211 A1 | 12/2004 | Maalouf |
| 2005/0010197 A1 | 1/2005 | Lau et al. |
| 2005/0033957 A1 | 2/2005 | Enokida |
| 2005/0049526 A1 | 3/2005 | Baer |
| 2005/0049543 A1 | 3/2005 | Anderson et al. |
| 2005/0049661 A1 | 3/2005 | Koffroth |
| 2005/0113725 A1 | 5/2005 | Masuda |
| 2005/0143781 A1 | 6/2005 | Carbunaru et al. |
| 2005/0145372 A1 | 7/2005 | Noel |

(56) References Cited

U.S. PATENT DOCUMENTS

| | | |
|---|---|---|
| 2005/0149153 A1 | 7/2005 | Nakase et al. |
| 2005/0154314 A1 | 7/2005 | Quistgaard |
| 2005/0154431 A1 | 7/2005 | Quistgaard et al. |
| 2005/0159986 A1 | 7/2005 | Breeland et al. |
| 2005/0177075 A1 | 8/2005 | Meunier et al. |
| 2005/0182462 A1 | 8/2005 | Chornenky et al. |
| 2005/0187495 A1 | 8/2005 | Quistgaard et al. |
| 2005/0187597 A1 | 8/2005 | Vanderschuit |
| 2005/0203446 A1 | 9/2005 | Takashima |
| 2005/0215987 A1 | 9/2005 | Slatkine |
| 2005/0222565 A1 | 10/2005 | Manstein |
| 2005/0251117 A1 | 11/2005 | Anderson et al. |
| 2005/0251120 A1 | 11/2005 | Anderson et al. |
| 2005/0261753 A1 | 11/2005 | Littrup et al. |
| 2005/0277859 A1 | 12/2005 | Carlsmith et al. |
| 2005/0283144 A1 | 12/2005 | Shiono et al. |
| 2006/0030778 A1 | 2/2006 | Mendlein et al. |
| 2006/0035380 A1 | 2/2006 | Saint-Leger |
| 2006/0036300 A1 | 2/2006 | Kreindel |
| 2006/0041704 A1 | 2/2006 | Choi |
| 2006/0074313 A1 | 4/2006 | Slayton et al. |
| 2006/0079852 A1 | 4/2006 | Bubb et al. |
| 2006/0094988 A1 | 5/2006 | Tosaya et al. |
| 2006/0106836 A1 | 5/2006 | Masugi et al. |
| 2006/0122509 A1 | 6/2006 | Desilets |
| 2006/0188832 A1* | 8/2006 | McCarren .................. F23D 5/04 431/125 |
| 2006/0189964 A1 | 8/2006 | Anderson et al. |
| 2006/0195168 A1 | 8/2006 | Dunbar et al. |
| 2006/0200063 A1 | 9/2006 | Munro et al. |
| 2006/0206040 A1 | 9/2006 | Greenberg et al. |
| 2006/0206110 A1 | 9/2006 | Knowlton et al. |
| 2006/0234899 A1 | 10/2006 | Nekmard et al. |
| 2006/0259102 A1 | 11/2006 | Slatkine |
| 2006/0265032 A1 | 11/2006 | Hennings et al. |
| 2006/0270745 A1 | 11/2006 | Hunt et al. |
| 2006/0293734 A1 | 12/2006 | Scott et al. |
| 2007/0010811 A1 | 1/2007 | Stern et al. |
| 2007/0010861 A1 | 1/2007 | Anderson et al. |
| 2007/0032561 A1 | 2/2007 | Lin et al. |
| 2007/0038156 A1 | 2/2007 | Rosenberg |
| 2007/0055156 A1 | 3/2007 | Desilets et al. |
| 2007/0055173 A1 | 3/2007 | DeLonzor et al. |
| 2007/0055179 A1 | 3/2007 | Deem et al. |
| 2007/0055180 A1 | 3/2007 | Deem et al. |
| 2007/0055181 A1 | 3/2007 | Deem et al. |
| 2007/0073367 A1 | 3/2007 | Jones et al. |
| 2007/0078502 A1 | 4/2007 | Weber et al. |
| 2007/0100398 A1 | 5/2007 | Sloan |
| 2007/0106342 A1 | 5/2007 | Schumann |
| 2007/0129714 A1 | 6/2007 | Elkins et al. |
| 2007/0135876 A1 | 6/2007 | Weber |
| 2007/0141265 A1 | 6/2007 | Thomson |
| 2007/0179482 A1 | 8/2007 | Anderson |
| 2007/0198071 A1 | 8/2007 | Ting et al. |
| 2007/0219540 A1 | 9/2007 | Masotti et al. |
| 2007/0239075 A1 | 10/2007 | Rosenberg et al. |
| 2007/0239150 A1 | 10/2007 | Zvuloni et al. |
| 2007/0249519 A1 | 10/2007 | Guha et al. |
| 2007/0255187 A1 | 11/2007 | Branch |
| 2007/0255274 A1 | 11/2007 | Stern et al. |
| 2007/0255362 A1* | 11/2007 | Levinson .................. A61F 7/10 607/96 |
| 2007/0265585 A1 | 11/2007 | Joshi et al. |
| 2007/0265614 A1 | 11/2007 | Stern et al. |
| 2007/0270925 A1 | 11/2007 | Levinson |
| 2007/0282249 A1 | 12/2007 | Quisenberry et al. |
| 2007/0282318 A1 | 12/2007 | Spooner et al. |
| 2008/0014627 A1 | 1/2008 | Merchant et al. |
| 2008/0046047 A1 | 2/2008 | Jacobs |
| 2008/0058784 A1 | 3/2008 | Manstein et al. |
| 2008/0077201 A1 | 3/2008 | Levinson et al. |
| 2008/0077202 A1 | 3/2008 | Levinson |
| 2008/0077211 A1 | 3/2008 | Levinson et al. |
| 2008/0139901 A1 | 6/2008 | Altshuler et al. |
| 2008/0140061 A1 | 6/2008 | Toubia et al. |
| 2008/0140371 A1 | 6/2008 | Warner |
| 2008/0161892 A1 | 7/2008 | Mercuro et al. |
| 2008/0183164 A1 | 7/2008 | Elkins et al. |
| 2008/0188915 A1 | 8/2008 | Mills et al. |
| 2008/0248554 A1 | 10/2008 | Merchant et al. |
| 2008/0269851 A1 | 10/2008 | Deem et al. |
| 2008/0287839 A1 | 11/2008 | Rosen et al. |
| 2008/0312651 A1 | 12/2008 | Pope et al. |
| 2009/0012434 A1 | 1/2009 | Anderson |
| 2009/0018623 A1 | 1/2009 | Levinson et al. |
| 2009/0018624 A1 | 1/2009 | Levinson et al. |
| 2009/0018625 A1 | 1/2009 | Levinson et al. |
| 2009/0018626 A1 | 1/2009 | Levinson et al. |
| 2009/0018627 A1 | 1/2009 | Levinson et al. |
| 2009/0024023 A1 | 1/2009 | Welches et al. |
| 2009/0076488 A1 | 3/2009 | Welches et al. |
| 2009/0112134 A1 | 4/2009 | Avni |
| 2009/0118722 A1 | 5/2009 | Ebbers et al. |
| 2009/0149929 A1 | 6/2009 | Levinson et al. |
| 2009/0149930 A1 | 6/2009 | Schenck |
| 2009/0171253 A1 | 7/2009 | Davenport |
| 2009/0171334 A1 | 7/2009 | Elkins et al. |
| 2009/0221938 A1 | 9/2009 | Rosenberg et al. |
| 2009/0276018 A1 | 11/2009 | Brader |
| 2009/0281464 A1 | 11/2009 | Cioanta et al. |
| 2009/0299234 A1 | 12/2009 | Cho et al. |
| 2009/0306749 A1 | 12/2009 | Mulindwa |
| 2009/0312676 A1 | 12/2009 | Rousso et al. |
| 2009/0312693 A1 | 12/2009 | Thapliyal et al. |
| 2009/0326621 A1 | 12/2009 | El-Galley |
| 2010/0015190 A1 | 1/2010 | Hassler |
| 2010/0028969 A1 | 2/2010 | Mueller et al. |
| 2010/0030306 A1 | 2/2010 | Edelman et al. |
| 2010/0036295 A1 | 2/2010 | Altshuler et al. |
| 2010/0042087 A1 | 2/2010 | Goldboss et al. |
| 2010/0049178 A1 | 2/2010 | Deem et al. |
| 2010/0081971 A1 | 4/2010 | Allison |
| 2010/0087806 A1 | 4/2010 | Da Silva et al. |
| 2010/0152824 A1 | 6/2010 | Allison |
| 2010/0168726 A1 | 7/2010 | Brookman |
| 2010/0179531 A1 | 7/2010 | Nebrigic et al. |
| 2010/0198064 A1 | 8/2010 | Perl et al. |
| 2010/0217349 A1 | 8/2010 | Fahey et al. |
| 2010/0268220 A1 | 10/2010 | Johnson et al. |
| 2010/0280582 A1* | 11/2010 | Baker ...................... A61F 7/007 607/113 |
| 2011/0009860 A1 | 1/2011 | Chornenky et al. |
| 2011/0040235 A1 | 2/2011 | Castel |
| 2011/0040299 A1 | 2/2011 | Kim et al. |
| 2011/0046523 A1 | 2/2011 | Altshuler et al. |
| 2011/0060323 A1 | 3/2011 | Baust et al. |
| 2011/0066083 A1 | 3/2011 | Tosaya et al. |
| 2011/0066216 A1 | 3/2011 | Ting et al. |
| 2011/0077557 A1 | 3/2011 | Wing et al. |
| 2011/0077723 A1 | 3/2011 | Parish et al. |
| 2011/0112405 A1 | 5/2011 | Barthe et al. |
| 2011/0112520 A1 | 5/2011 | Kreindel |
| 2011/0144631 A1 | 6/2011 | Elkins et al. |
| 2011/0152849 A1 | 6/2011 | Baust et al. |
| 2011/0172651 A1 | 7/2011 | Altshuler et al. |
| 2011/0189129 A1 | 8/2011 | Qiu et al. |
| 2011/0196395 A1 | 8/2011 | Maschke |
| 2011/0196438 A1 | 8/2011 | Mnozil et al. |
| 2011/0202048 A1 | 8/2011 | Nebrigic et al. |
| 2011/0238050 A1 | 9/2011 | Allison et al. |
| 2011/0238051 A1 | 9/2011 | Levinson et al. |
| 2011/0257642 A1 | 10/2011 | Griggs, III |
| 2011/0300079 A1 | 12/2011 | Martens et al. |
| 2011/0301585 A1 | 12/2011 | Goulko |
| 2011/0313411 A1 | 12/2011 | Anderson et al. |
| 2011/0313412 A1 | 12/2011 | Kim et al. |
| 2012/0010609 A1 | 1/2012 | Deem et al. |
| 2012/0016239 A1 | 1/2012 | Barthe et al. |
| 2012/0022518 A1 | 1/2012 | Levinson |
| 2012/0022622 A1 | 1/2012 | Johnson et al. |
| 2012/0035475 A1 | 2/2012 | Barthe et al. |
| 2012/0035476 A1 | 2/2012 | Barthe et al. |
| 2012/0041525 A1 | 2/2012 | Karni |

(56) References Cited

U.S. PATENT DOCUMENTS

| | | |
|---|---|---|
| 2012/0046547 A1 | 2/2012 | Barthe et al. |
| 2012/0053458 A1 | 3/2012 | Barthe et al. |
| 2012/0065629 A1 | 3/2012 | Elkins et al. |
| 2012/0083862 A1 | 4/2012 | Altshuler et al. |
| 2012/0101549 A1 | 4/2012 | Schumann |
| 2012/0109041 A1 | 5/2012 | Munz |
| 2012/0158100 A1 | 6/2012 | Schomacker |
| 2012/0209363 A1 | 8/2012 | Williams, III et al. |
| 2012/0233736 A1 | 9/2012 | Tepper et al. |
| 2012/0239123 A1 | 9/2012 | Weber et al. |
| 2012/0253416 A1 | 10/2012 | Erez et al. |
| 2012/0259322 A1 | 10/2012 | Fourkas et al. |
| 2012/0277674 A1 | 11/2012 | Clark, III et al. |
| 2012/0310232 A1 | 12/2012 | Erez |
| 2013/0018236 A1 | 1/2013 | Altshuler et al. |
| 2013/0019374 A1 | 1/2013 | Schwartz |
| 2013/0035680 A1* | 2/2013 | Ben-Haim ......... A61B 18/1815 606/33 |
| 2013/0066309 A1 | 3/2013 | Levinson |
| 2013/0073017 A1 | 3/2013 | Liu et al. |
| 2013/0079684 A1 | 3/2013 | Rosen et al. |
| 2013/0116758 A1 | 5/2013 | Levinson et al. |
| 2013/0116759 A1 | 5/2013 | Levinson et al. |
| 2013/0150844 A1 | 6/2013 | Deem et al. |
| 2013/0158440 A1 | 6/2013 | Allison |
| 2013/0158636 A1 | 6/2013 | Ting et al. |
| 2013/0166003 A1 | 6/2013 | Johnson et al. |
| 2013/0190744 A1 | 7/2013 | Avram et al. |
| 2013/0238062 A1 | 9/2013 | Ron Edoute et al. |
| 2013/0245507 A1 | 9/2013 | Khorassani Zadeh |
| 2013/0253384 A1 | 9/2013 | Anderson et al. |
| 2013/0253493 A1 | 9/2013 | Anderson et al. |
| 2013/0253494 A1 | 9/2013 | Anderson et al. |
| 2013/0253495 A1 | 9/2013 | Anderson et al. |
| 2013/0253496 A1 | 9/2013 | Anderson et al. |
| 2013/0303904 A1 | 11/2013 | Barthe et al. |
| 2013/0303905 A1 | 11/2013 | Barthe et al. |
| 2013/0331914 A1 | 12/2013 | Lee et al. |
| 2014/0005759 A1 | 1/2014 | Fahey et al. |
| 2014/0005760 A1 | 1/2014 | Levinson et al. |
| 2014/0067025 A1 | 3/2014 | Levinson et al. |
| 2014/0142469 A1 | 5/2014 | Britva et al. |
| 2014/0200487 A1 | 7/2014 | Ramdas et al. |
| 2014/0200488 A1 | 7/2014 | Seo et al. |
| 2014/0222121 A1 | 8/2014 | Spence et al. |
| 2014/0277219 A1 | 9/2014 | Nanda |
| 2014/0277302 A1 | 9/2014 | Weber et al. |
| 2014/0277303 A1 | 9/2014 | Biser et al. |
| 2014/0303697 A1 | 10/2014 | Anderson et al. |
| 2015/0209174 A1 | 7/2015 | Abreu |
| 2015/0216719 A1 | 8/2015 | DeBenedictis et al. |
| 2015/0216720 A1 | 8/2015 | DeBenedictis et al. |
| 2015/0216816 A1 | 8/2015 | O'Neil et al. |
| 2015/0223975 A1 | 8/2015 | Anderson et al. |
| 2015/0328077 A1 | 11/2015 | Levinson |
| 2015/0335468 A1 | 11/2015 | Rose et al. |
| 2015/0342780 A1 | 12/2015 | Levinson et al. |
| 2016/0051308 A1 | 2/2016 | Pennybacker et al. |
| 2016/0051401 A1 | 2/2016 | Yee et al. |
| 2016/0135985 A1 | 5/2016 | Anderson |
| 2016/0324684 A1 | 11/2016 | Levinson et al. |
| 2017/0007309 A1 | 1/2017 | DeBenedictis et al. |
| 2017/0079833 A1 | 3/2017 | Frangineas, Jr. et al. |
| 2017/0105869 A1 | 4/2017 | Frangineas, Jr. et al. |
| 2017/0165105 A1 | 6/2017 | Anderson et al. |
| 2017/0196731 A1 | 7/2017 | DeBenedictis et al. |
| 2017/0239079 A1 | 8/2017 | Root et al. |
| 2017/0325992 A1 | 11/2017 | DeBenedictis et al. |
| 2017/0325993 A1 | 11/2017 | Jimenez Lozano et al. |
| 2017/0326042 A1 | 11/2017 | Zeng et al. |
| 2017/0326346 A1 | 11/2017 | Jimenez Lozano et al. |
| 2018/0161197 A1 | 6/2018 | Baker et al. |
| 2019/0125424 A1 | 5/2019 | DeBenedictis et al. |
| 2019/0142493 A1 | 5/2019 | Debenedictis et al. |

FOREIGN PATENT DOCUMENTS

| | | |
|---|---|---|
| CA | 2585214 A1 | 10/2007 |
| CH | 333982 A | 11/1958 |
| CN | 86200604 U | 10/1987 |
| CN | 2514795 Y | 10/2002 |
| CN | 2514811 Y | 10/2002 |
| CN | 1511503 A | 7/2004 |
| CN | 1741777 A | 3/2006 |
| CN | 1817990 A | 8/2006 |
| CN | 2843367 Y | 12/2006 |
| CN | 2850584 Y | 12/2006 |
| CN | 2850585 Y | 12/2006 |
| CN | 200970265 Y | 11/2007 |
| CN | 101259329 A | 9/2008 |
| CN | 101309657 A | 11/2008 |
| DE | 532976 C | 9/1931 |
| DE | 2851602 A1 | 6/1980 |
| DE | 4213584 A1 | 11/1992 |
| DE | 4224595 A1 | 1/1994 |
| DE | 4238291 A1 | 5/1994 |
| DE | 4445627 A1 | 6/1996 |
| DE | 19800416 A1 | 7/1999 |
| EP | 263069 A2 | 4/1988 |
| EP | 0397043 A1 | 11/1990 |
| EP | 0406244 A1 | 1/1991 |
| EP | 560309 A1 | 9/1993 |
| EP | 0598824 A1 | 6/1994 |
| EP | 1030611 A1 | 8/2000 |
| EP | 1201266 A1 | 5/2002 |
| EP | 1568395 A1 | 8/2005 |
| EP | 2260801 A2 | 12/2010 |
| EP | 2289598 A1 | 3/2011 |
| EP | 2527005 A1 | 11/2012 |
| FR | 854937 A | 4/1940 |
| FR | 2744358 A1 | 8/1997 |
| FR | 2745935 A1 | 9/1997 |
| FR | 2767476 A1 | 2/1999 |
| FR | 2776920 A1 | 10/1999 |
| FR | 2789893 A | 8/2000 |
| FR | 2805989 A1 | 9/2001 |
| GB | 387960 A | 2/1933 |
| GB | 2120944 A | 12/1983 |
| GB | 2202447 A | 9/1988 |
| GB | 2248183 A | 4/1992 |
| GB | 2263872 A | 8/1993 |
| GB | 2286660 A | 8/1995 |
| GB | 2323659 A | 9/1998 |
| JP | 58187454 A | 11/1983 |
| JP | S6094113 U | 6/1985 |
| JP | 6282977 A | 4/1987 |
| JP | 63076895 A | 4/1988 |
| JP | 01223961 A | 9/1989 |
| JP | 03051964 A | 3/1991 |
| JP | 03259975 A | 11/1991 |
| JP | 04093597 A | 3/1992 |
| JP | 06261933 A | 9/1994 |
| JP | 07194666 A | 8/1995 |
| JP | 07268274 A | 10/1995 |
| JP | 09164163 A | 6/1997 |
| JP | 10216169 A | 8/1998 |
| JP | 10223961 A | 8/1998 |
| JP | 3065657 B2 | 7/2000 |
| JP | 2001046416 A | 2/2001 |
| JP | 2002125993 A | 5/2002 |
| JP | 2002224051 A | 8/2002 |
| JP | 2002282295 A | 10/2002 |
| JP | 2002290397 A | 10/2002 |
| JP | 2002543668 A | 12/2002 |
| JP | 2003190201 A | 7/2003 |
| JP | 2004013600 A | 1/2004 |
| JP | 2004073812 A | 3/2004 |
| JP | 2004159666 A | 6/2004 |
| JP | 2005039790 A | 2/2005 |
| JP | 2005065984 A | 3/2005 |
| JP | 2005110755 A | 4/2005 |
| JP | 2005509977 A | 4/2005 |
| JP | 3655820 B2 | 6/2005 |
| JP | 2005520608 A | 7/2005 |

(56) References Cited

FOREIGN PATENT DOCUMENTS

| | | |
|---|---|---|
| JP | 2005237908 A | 9/2005 |
| JP | 2005323716 A | 11/2005 |
| JP | 2006026001 A | 2/2006 |
| JP | 2006130055 A | 5/2006 |
| JP | 2006520949 A | 9/2006 |
| JP | 2007270459 A | 10/2007 |
| JP | 2008532591 A | 8/2008 |
| JP | 2009515232 A | 4/2009 |
| JP | 2009189757 A | 8/2009 |
| KR | 200173222 Y1 | 12/1999 |
| KR | 20040094508 A | 11/2004 |
| KR | 20090000258 U | 1/2009 |
| KR | 1020130043299 A | 4/2013 |
| KR | 1020140038165 A | 3/2014 |
| RU | 2036667 C1 | 6/1995 |
| SU | 532976 A1 | 11/1978 |
| TW | 0476644 B | 2/2002 |
| WO | 8503216 A1 | 8/1985 |
| WO | 9114417 A1 | 10/1991 |
| WO | 9300807 A1 | 1/1993 |
| WO | 9404116 A1 | 3/1994 |
| WO | 9623447 A1 | 8/1996 |
| WO | 9626693 A1 | 9/1996 |
| WO | 9636293 A1 | 11/1996 |
| WO | 9637158 A1 | 11/1996 |
| WO | 9704832 A1 | 2/1997 |
| WO | 9705828 A1 | 2/1997 |
| WO | 9722262 A2 | 6/1997 |
| WO | 9724088 A1 | 7/1997 |
| WO | 9725798 A1 | 7/1997 |
| WO | 9748440 A1 | 12/1997 |
| WO | 9829134 A2 | 7/1998 |
| WO | 9831321 A1 | 7/1998 |
| WO | 9841156 A1 | 9/1998 |
| WO | 9841157 A1 | 9/1998 |
| WO | 9909928 A1 | 3/1999 |
| WO | 9916502 A1 | 4/1999 |
| WO | 9938469 A1 | 8/1999 |
| WO | 9949937 A1 | 10/1999 |
| WO | 0044346 A1 | 8/2000 |
| WO | 0044349 A1 | 8/2000 |
| WO | 0065770 A1 | 11/2000 |
| WO | 0067685 A1 | 11/2000 |
| WO | 0100269 A1 | 1/2001 |
| WO | 0113989 A1 | 3/2001 |
| WO | 0114012 A1 | 3/2001 |
| WO | 0134048 A1 | 5/2001 |
| WO | 0205736 A1 | 1/2002 |
| WO | 02102921 A1 | 12/2002 |
| WO | 03007859 A1 | 1/2003 |
| WO | 03078596 A2 | 9/2003 |
| WO | 03079916 A1 | 10/2003 |
| WO | 2004000098 A2 | 12/2003 |
| WO | 2004080279 A2 | 9/2004 |
| WO | 2004090939 A2 | 10/2004 |
| WO | 2005033957 A1 | 4/2005 |
| WO | 2005046540 A1 | 5/2005 |
| WO | 2005060354 A2 | 7/2005 |
| WO | 2005096979 A1 | 10/2005 |
| WO | 2005112815 A1 | 12/2005 |
| WO | 2006066226 A1 | 6/2006 |
| WO | 2006094348 A1 | 9/2006 |
| WO | 2006106836 A1 | 10/2006 |
| WO | 2006116603 A2 | 11/2006 |
| WO | 2006127467 A2 | 11/2006 |
| WO | 2007012083 A2 | 1/2007 |
| WO | 2007028975 A1 | 3/2007 |
| WO | 2007041642 A2 | 4/2007 |
| WO | 2007101039 A2 | 9/2007 |
| WO | 2007127924 A2 | 11/2007 |
| WO | 2007145421 A1 | 12/2007 |
| WO | 2007145422 A1 | 12/2007 |
| WO | 2008006018 A2 | 1/2008 |
| WO | 2008039556 A1 | 4/2008 |
| WO | 2008039557 A1 | 4/2008 |
| WO | 2008055243 A2 | 5/2008 |
| WO | 2008143678 A1 | 11/2008 |
| WO | 2009011708 A1 | 1/2009 |
| WO | 2009026471 A1 | 2/2009 |
| WO | 2010077841 A1 | 7/2010 |
| WO | 2010127315 A2 | 11/2010 |
| WO | 2012012296 A1 | 1/2012 |
| WO | 2012103242 A1 | 8/2012 |
| WO | 2013013059 A1 | 1/2013 |
| WO | 2013075006 A1 | 5/2013 |
| WO | 2013075016 A1 | 5/2013 |
| WO | 2013190337 A1 | 12/2013 |
| WO | 2014151872 A3 | 9/2014 |
| WO | 2014191263 A1 | 12/2014 |
| WO | 2015117001 A1 | 8/2015 |
| WO | 2015117005 A1 | 8/2015 |
| WO | 2015117026 A2 | 8/2015 |
| WO | 2015117032 A1 | 8/2015 |
| WO | 2015117036 A2 | 8/2015 |
| WO | 2016028796 A1 | 2/2016 |
| WO | 2016048721 A1 | 3/2016 |

OTHER PUBLICATIONS

Al-Sakere, B. et al. "Tumor Ablation with Irreversible Electroporation," PLoS One, Issue 11, Nov. 2007, 8 pages.

Alster, T. et al., "Cellulite Treatment Using a Novel Combination Radiofrequency, Infrared Light, and Mechanical Tissue Manipulation Device," Journal of Cosmetic and Laser Therapy, vol. 7, 2005, pp. 81-85.

Ardevol, A. et al., "Cooling Rates of Tissue Samples During Freezing with Liquid Nitrogen," Journal of Biochemical and Biophysical Methods, vol. 27, 1993, pp. 77-86.

Arena, C. B. et al., "High-Frequency Irreversible Electroporation (H-FIRE) for Non-Thermal Ablation Without Muscle Contraction," BioMedical Engineering OnLine 2011, 10:102, Nov. 21, 2011, 21 pgs.

Becker, S. M. et al. "Local Temperature Rises Influence In Vivo Electroporation Pore Development: A Numerical Stratum Corneum Lipid Phase Transition Model," Journal of Biomechanical Engineering, vol. 129, Oct. 2007, pp. 712-721.

Bohm, T. et al., "Saline-Enhanced Radiofrequency Ablation of Breast Tissue: an in Vitro Feasibility Study," Investigative Radiology, vol. 35 (3), 2000, pp. 149-157.

Bondei, E. et al., "Disorders of Subcutaneous Tissue (Cold Panniculitis)," Dermatology in General Medicine, Fourth Edition, vol. 1, Chapter 108, 1993, Section 16, pp. 1333-1334.

Burge, S.M. et al., "Hair Follicle Destruction and Regeneration in Guinea Pig Skin after Cutaneous Freeze Injury," Cryobiology, 27(2), 1990, pp. 153-163.

Coban, Y. K. et al., "Ischemia-Reperfusion Injury of Adipofascial Tissue: An Experimental Study Evaluating Early Histologic and Biochemical Alterations in Rats," Mediators of Inflammation, 2005, 5, pp. 304-308.

Del Pino, M. E. et al. "Effect of Controlled Volumetric Tissue Heating with Radiofrequency on Cellulite and the Subcutaneous Tissue of the Buttocks and Thighs," Journal of Drugs in Dermatology, vol. 5, Issue 8, Sep. 2006, pp. 714-722.

Donski, P. K. et al., "The Effects of Cooling no Experimental Free Flap Survival," British Journal of Plastic Surgery, vol. 33, 1980, pp. 353-360.

Duck, F. A., Physical Properties of Tissue, Academic Press Ltd., chapters 4 & 5, 1990, pp. 73-165.

Duncan, W. C. et al., "Cold Panniculitis," Archives of Dermatology, vol. 94, Issue 6, Dec. 1966, pp. 722-724.

Epstein, E. H. et al., "Popsicle Panniculitis," The New England Journal of Medicine, 282(17), Apr. 23, 1970, pp. 966-967.

Fournier, L. et al. "Lattice Model for the Kinetics of Rupture of Fluid Bilayer Membranes," Physical Review, vol. 67, 2003, pp. 051908-1-051908-11.

Gabriel, S. et al., "The Dielectric Properties of Biological Tissues: II. Measurements in the Frequency Range 10 Hz to 20 GHz," Physics in Medicine and Biology, vol. 41, 1996, pp. 2251-2269.

(56) References Cited

OTHER PUBLICATIONS

Gage, A. "Current Progress in Cryosurgery," Cryobiology 25, 1988, pp. 483-486.
Gatto, H. "Effects of Thermal Shocks on Interleukin-1 Levels and Heat Shock Protein 72 (HSP72) Expression in Normal Human Keratinocytes," PubMed, Archives of Dermatological Research, vol. 284, Issue 7, 1992: pp. 414-417 [Abstract].
Hale, H. B. et al., "Influence of Chronic Heat Exposure and Prolonged Food Deprivation on Excretion of Magnesium, Phosphorus, Calcium, Hydrogen Ion & Ketones," Aerospace Medicine, vol. 39—No. 9, Sep. 1968, pp. 919-926.
Heller Page, E. et al., "Temperature-dependent skin disorders," Journal of the American Academy of Dermatology, vol. 18, No. 5, Pt 1, May 1988, pp. 1003-1019.
Hemmingsson, A. et al. "Attenuation in Human Muscle and Fat Tissue in Vivo and in Vitro," Acra Radiologica Diagnosis, vol. 23, No. 2, 1982, pp. 149-151.
Henry, F. et al., "Les Dermatoses Hivernales," Rev Med Liege, 54:11, 1999, pp. 864-866.
Hernan, P. et al., "Study for the evaluation of the efficacy of Lipocryolysis (EEEL)", Nov. 30, 2011.
Hernan, R. P., "A Study to Evaluate the Action of Lipocryolysis", 33(3) CryoLellers, 2012, pp. 176-180.
Holland, DB. et al. "Cold shock induces the synthesis of stress proteins in human keratinocytes," PubMed Journal of Investigative Dermatology; 101(2): Aug. 1993, pp. 196-199.
Holman, W. L. et al., "Variation in Cryolesion Penetration Due to Probe Size and Tissue Thermal Conductivity," The Annals of Thoracic Surgery, vol. 53, 1992, pp. 123-126.
Hong, J.S. et al., "Patterns of Ice Formation in Normal and Malignant Breast Tissue," Cryobiology 31, 1994, pp. 109-120.
Huang et al. "Comparative Proteomic Profiling of Murine Skin," Journal of Investigative Dermatology, vol. 121(1), Jul. 2003, pp. 51-64.
Isambert, H. "Understanding the Electroporation of Cells and Artificial Bilayer Membranes," Physical Review Letters, vol. 80, No. 15, 1998, pp. 3404-3707.
Jalian, H. R. et al., "Cryolipolysis: A Historical Perspective and Current Clinical Practice", 32(1) Semin. Cutan. Med. Surg., 2013, pp. 31-34.
Kellum, R. E. et al., "Sclerema Neonatorum: Report of Case and Analysis of Subcutaneous and Epidermal-Dermal Lipids by Chromatographic Methods," Archives of Dermatology, vol. 97, Apr. 1968, pp. 372-380.
Koska, J. et al., "Endocrine Regulation of Subcutaneous Fat Metabolism During Cold Exposure in Humans," Annals of the New York Academy of Sciences, vol. 967, 2002, pp. 500-505.
Kumakura et al.; Office Action: Notification of Reason for Rejection; Japanese Patent Application No. 2010-213871; Dispatch No. 254910; Dispatched; Apr. 16, 2012; Drawn up on: Apr. 12, 2012.
Kundu, S. K. et al., "Breath Acetone Analyzer: Diagnostic Tool to Monitor Dietary Fat Loss," Clinical Chemistry, vol. 39, Issue (1), 1993, pp. 87-92.
Kundu, S. K. et al., "Novel Solid-Phase Assay of Ketone Bodies in Urine," Clinical Chemistry, vol. 37, Issue (9), 1991, pp. 1565-1569.
Kuroda, S. et al. "Thermal Distribution of Radio-Frequency Inductive Hyperthermia Using an Inductive Aperture-Type Applicator: Evaluation of the Effect of Tumor Size and Depth", Medical and Biological Engineering and Computing, vol. 37, 1999, pp. 285-290.
Laugier, P. et al., "In Vivo Results with a New Device for Ultrasonic Monitoring of Pig Skin Cryosurgery: The Echographic Cryprobe," The Society for Investigative Dermatology, Inc., vol. 111, No. 2, Aug. 1998, pp. 314-319.
Levchenko et al., "Effect of Dehydration on Lipid Metabolism" Ukrainskii Biokhimicheskii Zhurnal, vol. 50, Issue 1, 1978, pp. 95-97.
Lidagoster, MD et al., "Comparison of Autologous Fat Transfer in Fresh, Refrigerated, and Frozen Specimens: An Animal Model," Annals of Plastic Surgery, vol. 44, No. 5, May 2000, pp. 512-515.
Liu, A. Y.-C. et al., "Transient Cold Shock Induces the Heat Shock Response upon Recovery at 37 C in Human Cells," Journal of Biological Chemistry, , 269(20), May 20, 1994, pp. 14768-14775.
L'Vova, S.P. "Lipid Levels and Lipid Peroxidation in Frog Tissues During Hypothermia and Hibernation" Ukrainskii Biokhimicheskii Zhurnal, vol. 62, Issue 1, 1990, pp. 65-70.
Maize, J.C. "Panniculitis," Cutaneous Pathology, Chapter 13, 1998, 327-344.
Malcolm, G. T. et al., "Fatty Acid Composition of Adipose Tissue in Humans: Differences between Subcutaneous Sites," The American Journal of Clinical Nutrition, vol. 50, 1989, pp. 288-291.
Manstein, D. et al. "A Novel Cryotherapy Method of Non-invasive, Selective Lipolysis," LasersSurg.Med 40:S20, 2008, p. 104.
Manstein, D. et al. "Selective Cryolysis: A Novel Method of Non-Invasive Fat Removal," Lasers in Surgery and Medicine: The Official Journal of the ASLMS, vol. 40, No. 9, Nov. 2008, pp. 595-604.
Mayoral, "Case Reports: Skin Tightening with a Combined Unipolar and Bipolar Radiofrequency Device," Journal of Drugs in Dermatology, 2007, pp. 212-215.
Mazur, P. "Cryobiology: The Freezing of Biological Systems," Science, 68, 1970, pp. 939-949.
Merrill, T. "A Chill to the Heart: A System to Deliver Local Hypothermia Could One Day Improve the Lives of Heart-Attack Patients," Mechanical Engineering Magazine, Oct. 2010, 10 pages.
Miklavcic, D. et al. "Electroporation-Based Technologies and Treatments," The Journal of Membrane Biology (2010) 236:1-2, 2 pgs.
Moschella, S. L. et al., "Diseases of the Subcutaneous Tissue," in Dermatology, Second Edition, vol. 2, 1985 Chapter 19, Section II (W.B. Saunders Company, 1980) pp. 1169-1181.
Murphy, J. V. et al., "Frostbite: Pathogenesis and Treatment" The Journal of Trauma: Injury, Infection, and Critical Care, vol. 48, No. 1, Jan. 2000, pp. 171-178.
Nagao, T. et al., "Dietary Diacylglycerol Suppresses Accumulation of Body Fat Compared to Triacylglycerol in Men a Double-Blind Controlled Trial," The Journal of Nutrition, vol. 130, Issue (4), 2000, pp. 792-797.
Nagle, W. A. et al. "Cultured Chinese Hamster Cells Undergo Apoptosis After Exposure to Cold but Nonfreezing Temperatures," Cryobiology 27, 1990, pp. 439-451.
Nagore, E. et al., "Lipoatrophia Semicircularis—a Traumatic Panniculitis: Report of Seven Cases and Review of the Literature," Journal of the American Academy of Dermatology, vol. 39, Nov. 1998, pp. 879-881.
Nanda, G.S. et al., "Studies on electroporation of thermally and chemically treated human erythrocytes," Bioelectrochemistry and Bioenergetics, 34, 1994, pp. 129-134, 6 pgs.
Narins, D.J. et al. "Non-Surgical Radiofrequency Facelift", The Journal of Drugs in Dermatology, vol. 2, Issue 5, 2003, pp. 495-500.
Nielsen, B. "Thermoregulation in Rest and Exercise," Acta Physiologica Scandinavica Supplementum, vol. 323 (Copenhagen 1969), pp. 7-74.
Nishikawa, H. et al. "Ultrastructural Changes and Lipid Peroxidation in Rat Adipomusculocutaneous Flap Isotransplants after Normothermic Storage and Reperfusion," Transplantation, vol. 54, No. 5,1992, pp. 795-801.
Nurnberger, F. "So-Called Cellulite: An Invented Disease," Journal of Dermatologic Surgery and Oncology, Mar. 1978, pp. 221-229.
Pease, G. R. et al., "An Integrated Probe for Magnetic Resonance Imaging Monitored Skin Cryosurgery," Journal of Biomedical Engineering, vol. 117, Feb. 1995, pp. 59-63.
Pech, P. et al., "Attenuation Values, Volume Changes and Artifacts in Tissue Due to Freezing," Acta Radiologica ,vol. 28, Issue 6, 1987, pp. 779-782.
Peterson, L. J. et al., "Bilateral Fat Necrosis of the Scrotum," Journal of Urology, vol. 116, 1976, pp. 825-826.
Phinney, S. D. et al., "Human Subcutaneous Adipose Tissue Shows Site-Specific Differences in Fatty Acid Composition," The American Journal of Clinical Nutrition, vol. 60, 1994, pp. 725-729.
Pierard, G.E. et al., "Cellulite: From Standing Fat Herniation to Hypodermal Stretch Marks," The American Journal of Dermatology, vol. 22, Issue 1, 2000, pp. 34-37.

(56) References Cited

OTHER PUBLICATIONS

Pope, K. et al. "Selective Fibrous Septae Heating: An Additional Mechanism of Action for Capacitively Coupled Monopolar Radiofrequency" Thermage, Inc. Article, Feb. 2005, 6pgs.

Quinn, P. J. "A Lipid-Phase Separation Model of Low-Temperature Damage to Biological Membranes," Cryobiology, 22, 1985, 128-146.

Rabi, T. et al., "Metabolic Adaptations in Brown Adipose Tissue of the Hamster in Extreme Ambient Temperatures," American Journal of Physiology, vol. 231, Issue 1, Jul. 1976, pp. 153-160.

Renold, A.E. et al. "Adipose Tissue" in Handbook of Physiology, Chapter 15, (Washington, D.C., 1965) pp. 169-176.

Rossi, A. B. R. et al. "Cellulite: a Review," European Academy of Dermatology and Venercology, 2000, pp. 251-262, 12 pgs.

Rubinsky, B. "Principles of Low Temperature Cell Preservation," Heart Failure Reviews, vol. 8, 2003, pp. 277-284.

Rubinsky, B. et al., "Cryosurgery: Advances in the Application of low Temperatures to Medicine," International Journal of Refrigeration, vol. 14, Jul. 1991, pp. 190-199.

Saleh, K.Y. et al., "Two-Dimensional Ultrasound Phased Array Design for Tissue Ablation for Treatment of Benign Prostatic Hyperplasia," International Journal of Hyperthermia, vol. 20, No. 1, Feb. 2004, pp. 7-31.

Schoning, P. et al., "Experimental Frostbite: Freezing Times, Rewarming Times, and Lowest Temperatures of Pig Skin Exposed to Chilled Air," Cryobiology 27, 1990, pp. 189-193.

Shephard, R. J. "Adaptation to Exercise in the Cold," Sports Medicine, vol. 2, 1985, pp. 59-71.

Sigma-Aldrich "Poly (ethylene glycol) and Poly (ethylene oxide)," http://www.sigmaaldrich.com/materials-science/materialscience-;products.htmi?TablePage=2020411 0, accessed Oct. 19, 2012.

Smalls, L. K. et al. "Quantitative Model of Cellulite: Three Dimensional Skin Surface Topography, Biophysical Characterization, and Relationship to Human Perception," International Journal of Cosmetic Science, vol. 27, Issue 5, Oct. 2005, 17 pgs.

Thermage, News Release, "Study Published in Facial Plastic Surgery Journal Finds Selective Heating of Fibrous Septae Key to Success and Safety of Thermage ThermaCool System," Jun. 20, 2005, 2 pages.

Thermage, Inc. Tech Brochure, "ThermaCool Monopolar Capacitive Radiofrequency, the one choice for nonablative tissue tightening and contouring", Nov. 30, 2005, 8 pgs.

Vallerand et al. "Cold Stress Increases Lipolysis, FFA Ra and TG/FFA Cycling in Humans," Aviation, Space, and Environmental Medicine 70(1), 1999, pp. 42-50.

Wang, X. et al., "Cryopreservation of Cell/Hydrogel Constructs Based on a new Cell-Assembling Technique," Sep. 5, 2009, 40 pages.

Wharton, D. A. et al., "Cold Acclimation and Cryoprotectants in a Freeze-Tolerant Antarctic Nematode, Panagrolaimus Davidi,", Journal of Comparative Physiology, vol. 170, No. 4, Mar. 2000, 2 pages.

Winkler, C. et al., "Gene Transfer in Laboratory Fish: Model Organisms for the Analysis of Gene Function," in Transgenic Animals, Generation and Use (The Netherlands 1997), pp. 387-395.

Young, H. E. et al. "Isolation of Embryonic Chick Myosatellite and Pluripotent Stem Cells" The Journal of Tissue Culture Methods, vol. 14, Issue 2, 1992, pp. 85-92.

Zelickson, B. et al., "Cryolipolysis for Noninvasive Fat Cell Destruction: Initial Results from a Pig Model", 35 Dermatol. Sug., 2009, pp. 1-9.

Zouboulis, C. C. et al., "Current Developments and Uses of Cryosurgery in the Treatment of Keloids and Hypertrophic Scars," Wound Repair and Regeneration, vol. 10, No. 2, 2002, pp. 98-102.

\* cited by examiner

COOLING CUP APPLICATORS WITH CONTOURED HEADS AND LINER ASSEMBLIES

CROSS-REFERENCE TO RELATED APPLICATION

The present application claims the benefit of and priority under 35 U.S.C. § 119(e) to U.S. Provisional Patent Application No. 62/297,054, filed Feb. 18, 2016, which is incorporated herein by reference in its entirety.

INCORPORATION BY REFERENCE OF APPLICATIONS AND PATENTS

The following commonly assigned U.S. Patent Applications and U.S. Patents are incorporated herein by reference in their entireties:
U.S. Patent Publication No. 2008/0287839 entitled "METHOD OF ENHANCED REMOVAL OF HEAT FROM SUBCUTANEOUS LIPID-RICH CELLS AND TREATMENT APPARATUS HAVING AN ACTUATOR";
U.S. Pat. No. 6,032,675 entitled "FREEZING METHOD FOR CONTROLLED REMOVAL OF FATTY TISSUE BY LIPOSUCTION";
U.S. Patent Publication No. 2007/0255362 entitled "CRYOPROTECTANT FOR USE WITH A TREATMENT DEVICE FOR IMPROVED COOLING OF SUBCUTANEOUS LIPID-RICH CELLS";
U.S. Pat. No. 7,854,754 entitled "COOLING DEVICE FOR REMOVING HEAT FROM SUBCUTANEOUS LIPID-RICH CELLS";
U.S. Pat. No. 8,337,539 entitled "COOLING DEVICE FOR REMOVING HEAT FROM SUBCUTANEOUS LIPID-RICH CELLS";
U.S. Patent Publication No. 2008/0077201 entitled "COOLING DEVICES WITH FLEXIBLE SENSORS";
U.S. Pat. No. 9,132,031 entitled "COOLING DEVICE HAVING A PLURALITY OF CONTROLLABLE COOLING ELEMENTS TO PROVIDE A PREDETERMINED COOLING PROFILE";
U.S. Patent Publication No. 2009/0118722, filed Oct. 31, 2007, entitled "METHOD AND APPARATUS FOR COOLING SUBCUTANEOUS LIPID-RICH CELLS OR TISSUE";
U.S. Patent Publication No. 2009/0018624 entitled "LIMITING USE OF DISPOSABLE SYSTEM PATIENT PROTECTION DEVICES";
U.S. Pat. No. 8,523,927 entitled "SYSTEM FOR TREATING LIPID-RICH REGIONS";
U.S. Patent Publication No. 2009/0018625 entitled "MANAGING SYSTEM TEMPERATURE TO REMOVE HEAT FROM LIPID-RICH REGIONS";
U.S. Patent Publication No. 2009/0018627 entitled "SECURE SYSTEM FOR REMOVING HEAT FROM LIPID-RICH REGIONS";
U.S. Patent Publication No. 2009/0018626 entitled "USER INTERFACES FOR A SYSTEM THAT REMOVES HEAT FROM LIPID-RICH REGIONS";
U.S. Pat. No. 6,041,787 entitled "USE OF CRYOPROTECTIVE AGENT COMPOUNDS DURING CRYOSURGERY";
U.S. Pat. No. 8,285,390 entitled "MONITORING THE COOLING OF SUBCUTANEOUS LIPID-RICH CELLS, SUCH AS THE COOLING OF ADIPOSE TISSUE";
U.S. Pat. No. 8,275,442 entitled "TREATMENT PLANNING SYSTEMS AND METHODS FOR BODY CONTOURING APPLICATIONS";
U.S. patent application Ser. No. 12/275,002 entitled "APPARATUS WITH HYDROPHILIC RESERVOIRS FOR COOLING SUBCUTANEOUS LIPID-RICH CELLS";
U.S. patent application Ser. No. 12/275,014 entitled "APPARATUS WITH HYDROPHOBIC FILTERS FOR REMOVING HEAT FROM SUBCUTANEOUS LIPID-RICH CELLS";
U.S. patent application Ser. No. 15/400,885 entitled "TEMPERATURE-DEPENDENT ADHESION BETWEEN APPLICATOR AND SKIN DURING COOLING OF TISSUE";
U.S. Pat. No. 8,603,073 entitled "SYSTEMS AND METHODS WITH INTERRUPT/RESUME CAPABILITIES FOR COOLING SUBCUTANEOUS LIPID-RICH CELLS";
U.S. Pat. No. 8,192,474 entitled "TISSUE TREATMENT METHODS";
U.S. Pat. No. 8,702,774 entitled "DEVICE, SYSTEM AND METHOD FOR REMOVING HEAT FROM SUBCUTANEOUS LIPID-RICH CELLS";
U.S. Pat. No. 8,676,338 entitled "COMBINED MODALITY TREATMENT SYSTEMS, METHODS AND APPARATUS FOR BODY CONTOURING APPLICATIONS";
U.S. Pat. No. 9,314,368 entitled "HOME-USE APPLICATORS FOR NON-INVASIVELY REMOVING HEAT FROM SUBCUTANEOUS LIPID-RICH CELLS VIA PHASE CHANGE COOLANTS, AND ASSOCIATED DEVICES, SYSTEMS AND METHODS";
U.S. Publication No. 2011/0238051 entitled "HOME-USE APPLICATORS FOR NON-INVASIVELY REMOVING HEAT FROM SUBCUTANEOUS LIPID-RICH CELLS VIA PHASE CHANGE COOLANTS, AND ASSOCIATED DEVICES, SYSTEMS AND METHODS";
U.S. Publication No. 2012/0239123 entitled "DEVICES, APPLICATION SYSTEMS AND METHODS WITH LOCALIZED HEAT FLUX ZONES FOR REMOVING HEAT FROM SUBCUTANEOUS LIPID-RICH CELLS";
U.S. Pat. No. 9,545,523 entitled "MULTI-MODALITY TREATMENT SYSTEMS, METHODS AND APPARATUS FOR ALTERING SUBCUTANEOUS LIPID-RICH TISSUE";
U.S. Patent Publication No. 2014/0277302 entitled "TREATMENT SYSTEMS WITH FLUID MIXING SYSTEMS AND FLUID-COOLED APPLICATORS AND METHODS OF USING THE SAME";
U.S. Pat. No. 9,132,031 entitled "COOLING DEVICE HAVING A PLURALITY OF CONTROLLABLE COOLING ELEMENTS TO PROVIDE A PREDETERMINED COOLING PROFILE;"
U.S. Pat. No. 8,285,390 entitled "MONITORING THE COOLING OF SUBCUTANEOUS LIPID-RICH CELLS, SUCH AS THE COOLING OF ADIPOSE TISSUE;" and
U.S. Patent Publication No. 2016/0054101 entitled "TREATMENT SYSTEMS, SMALL VOLUME APPLICATORS, AND METHODS FOR TREATING SUBMENTAL TISSUE."

TECHNICAL FIELD

The present disclosure relates generally to treatment systems and contoured applicators with cooling cups. Several embodiments are directed to cooling cup applicators with contoured heads and/or liner assemblies.

BACKGROUND

Excess body fat, or adipose tissue, may be present at various locations of a subject's body and may detract from personal appearance. Aesthetic improvement of the human body often involves the selective removal of adipose tissue located at the abdomen, thighs, buttocks, knees, submental region, face and arms, as well as other locations. Invasive procedures (e.g., liposuction), however, tend to be associated with relative high costs, long recovery times, and increased risk of complications. Injection of drugs for reducing adipose tissue can cause significant swelling, bruising, pain, numbness, and/or induration.

Conventional non-invasive treatments for reducing adipose tissue often include regular exercise, application of topical agents, use of weight-loss drugs, dieting, or a combination of these treatments. One drawback of these non-invasive treatments is that they may not be effective or even possible under certain circumstances. For example, when a person is physically injured or ill, regular exercise may not be an option. Topical agents and orally administered weight-loss drugs are not an option if, as another example, they cause an undesirable reaction, such as an allergic or negative reaction. Additionally, non-invasive treatments may be ineffective for selectively reducing specific regions of adiposity, such as localized adipose tissue along the hips, abdomen, thighs, or the like.

Conventional non-invasive vacuum cooling devices suck a fold of skin between two spaced apart cooled plates that are generally parallel to one another. The cooling device can cool and thermally damage targeted tissue. Unfortunately, only opposites sides of the skin fold contact the cooled plates, which limits the cooling capabilities of the cooling devices. Additionally, the end of the tissue fold located in a gap between the plates may experience pooling of blood. A vacuum may cause rupturing of blood vessels and lead to bruising of the skin located in the gap. Accordingly, conventional invasive and non-invasive treatments are not suitable for many subjects and cannot effectively target certain regions of tissue.

BRIEF DESCRIPTION OF THE DRAWINGS

In the drawings, identical reference numbers identify similar elements or acts.

DETAILED DESCRIPTION

A. Overview

Figure 1:
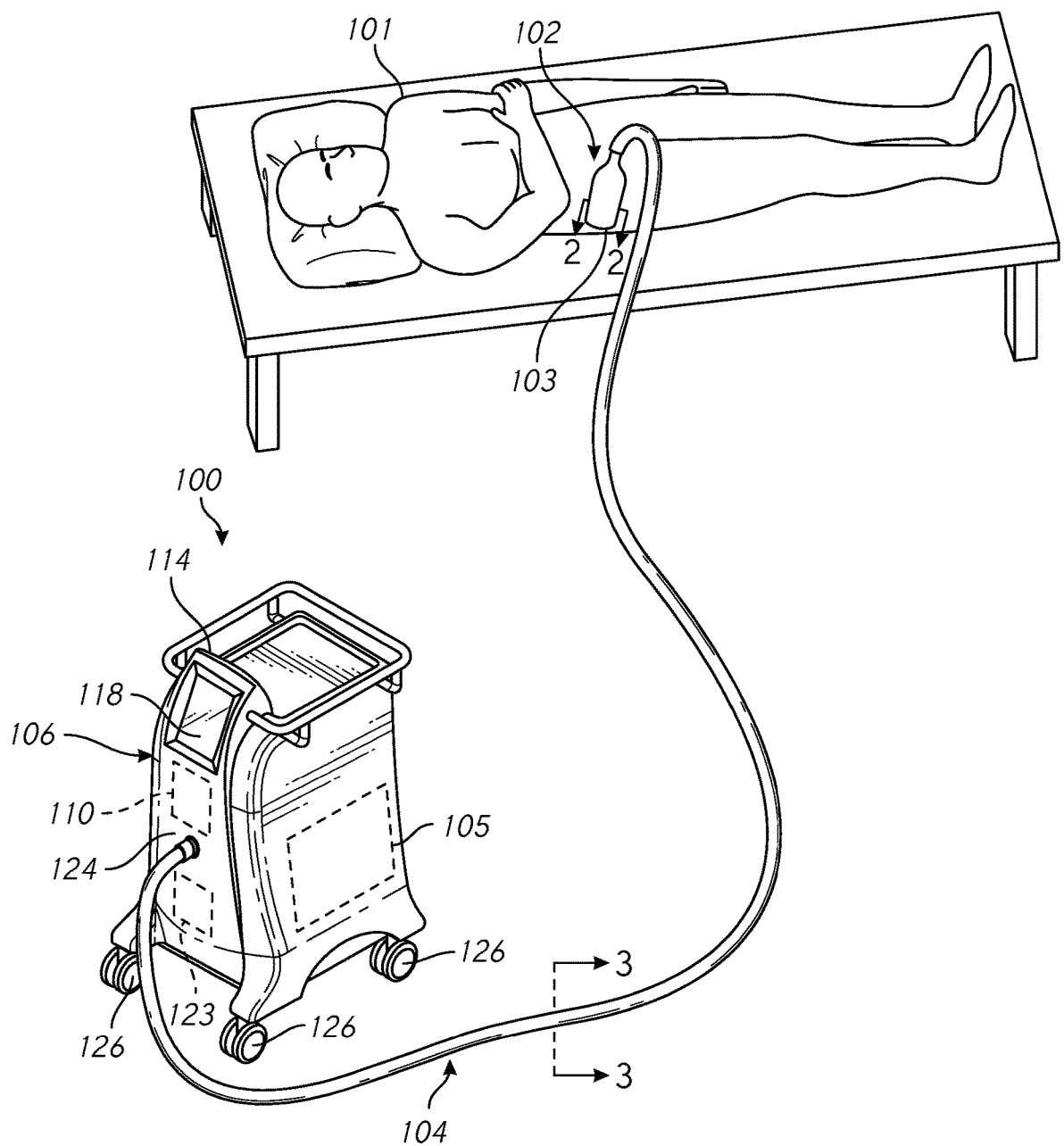
FIG. 1 is a partially schematic, isometric view of a treatment system for non-invasively affecting target regions of a subject in accordance with an embodiment of the technology.

The present disclosure describes treatment systems, applicators, and methods for affecting targeted sites. Several embodiments are directed to non-invasive systems that cool/heat specific regions or volumes of tissue. The non-invasive systems can include applicators with thermally-conductive cooling cups for cooling the skin surface of a retained volume of tissue. The applicators can be reconfigurable to enable treatment at various sites. Several of the details set forth below are provided to describe the following examples and methods in a manner sufficient to enable a person skilled in the relevant art to practice, make, and use them. Several of the details and advantages described below, however, may not be necessary to practice certain examples and methods of the technology. Additionally, the technology may include other examples and methods that are within the scope of the technology but are not described in detail.

Systems for treating a subject's tissue can include a cooling cup applicator with a base unit having a tissue-receiving cavity. A contoured head can be coupled to the base unit to provide a suitable interface for sealing with the subject's skin. A sealing member can be disposed between the base unit and the contoured head to create and maintain a vacuum seal therebetween. Once the contoured head is pressed against the subject's skin, a vacuum can be drawn to pull tissue through the head into the tissue-receiving cavity.

A temperature-controlled surface of the cooling cup can then conductively cool/heat the skin. Different contoured heads can be alternatively attached to the base unit and sealing member to create various sizes of applicators to be able to treat various treatment sites, specific volumes of tissue, or the like. Sealing members can be located at various locations to provide sealing (e.g., liquid-tight sealing, air-tight sealing, etc.) between components of the applicators. The seals can be maintained throughout treatment.

A disposable liner assembly can optionally be coupled to or integrated with the applicator to provide a sanitary patient-contact surface. The applicator can securely hold the liner assembly to allow repositioning of the applicator along the patient. The liner assembly can be replaced with another linear assembly to perform procedures on another patient to, for example, prevent cross-contamination between patients. The liner assembly can include a liner which is attached to the sealing member, with the liner extending across the tissue receiving cavity of the base unit. In some treatments, contoured heads, liner assemblies, and/or patient contact elements can be replaced to avoid cross-contamination between patients. Accordingly, most or all of the surfaces of the applicator that contact the patient can be replaced at any time.

The applicator can have one or more vacuum ports used to draw the liner assembly and/or tissue into the tissue-receiving cavity. In some embodiments, the liner assembly has an adhesive surface for adhering to the cooling cup and can be perforated to allow air flow therethrough. The liner assembly can be made, in whole or in part, of plastic, rubber, or other suitable material and can include, without limitation, one or more sealing members, sensors, release liners, carriers, alignment features, or the like.

Tissue can be pulled into the applicator such that the tissue fills most or substantially all of the tissue-receiving cavity. In some embodiments, a vacuum can be drawn to pull the skin against a relatively large area of the cup, thereby providing a relatively large skin-cup interface for heat transfer. A temperature-controlled conductive surface of the cooling cup can extend continuously along spaced apart sidewalls and bottom of the cooling cup and can thermally contact an area of the subject's skin that is equal to or less than about 20 $cm^2$, 40 $cm^2$, 80 $cm^2$, 100 $cm^2$, 140 $cm^2$, 160 $cm^2$, 180 $cm^2$, 200 $cm^2$, 300 $cm^2$, or other suitable area. In some embodiments, the temperature-controlled conductive surface can be cooled to a temperature equal to or less than a selected temperature (e.g., 5° C., 0° C., −2° C., −5° C., −7° C., −10° C., −15° C., −20° C., −25° C., etc.) to cool most of the skin surface of the retained tissue. In some embodiments, most of a heat-exchanging surface of the cup can be cooled to a temperature equal to or less than about 0° C., −2° C., −5° C., −10° C., or −15° C. The temperature-controlled surface area of the cooling cup can be, for example, equal to or less than 20 $cm^2$, 40 $cm^2$, 80 $cm^2$, 100 $cm^2$, 140 $cm^2$, 160 $cm^2$, 180 $cm^2$, 200 $cm^2$, 300 $cm^2$, or another suitable area.

In some embodiments, an apparatus for treating a subject's tissue includes an applicator configured to cool targeted tissue and a controller. The applicator includes a base unit, a head, a sealing member, and optionally a liner. The base unit has a temperature-controlled cup with a conductive heat-exchanging surface defining a tissue-receiving cavity. The head is removably coupleable to the base unit and includes a mounting body and a contoured mouth. The mounting body is configured to be coupled to the base unit to position an opening defined by the contoured mouth with respect to an entrance of the tissue-receiving cavity. The sealing member is disposed between the base unit and the head to create a vacuum seal therebetween. When the liner is used, a liner assembly can include the sealing member and the liner. The sealing member is positionable between the mounting body of the head and the base unit such that the liner extends across the entrance of the tissue-receiving cavity. The liner can be drawn into the tissue-receiving cavity until the liner lines the conductive surface. A majority or the entire liner can be located within the apparatus when the liner lines the conductive surface. The controller can be programmed to command the applicator to draw a vacuum in the tissue-receiving cavity to pull the liner against the conductive heat-exchanging surface.

In another embodiment, an apparatus for treating a subject's tissue comprises a base unit, a head, and a sealing member. The base unit includes a temperature-controlled cup having a conductive surface defining a tissue-receiving cavity. The head includes a mounting body and a contoured mouth. The mounting body is configured to be coupled to the base unit to position an opening defined by the contoured mouth with respect to an entrance of the tissue-receiving cavity. The sealing member is between the base unit and the head to create a seal (e.g., a vacuum seal or other desired seal) therebetween. A liner assembly can include the sealing member and a liner. The sealing member is positionable between the mounting body of the head and the base unit such that the liner extends across the entrance of the tissue-receiving cavity. The liner assembly can be drawn through the tissue-receiving cavity and against at least a portion of the conductive surface of the cup. Sealing members can be installed at other locations to inhibit or prevent leakage (e.g., air leakage into or out of the applicator).

In some embodiments, a contoured head can be configured to clamp onto a base unit via the sealing member to form an applicator. The applicator can be applied to treatment sites while the sealing member remains secured to the applicator, and one can release the sealing member and separate the contoured head from the base unit so as to install another contoured head and sealing member to the base unit. In some embodiments, a liner assembly can be sandwiched between the base unit and contoured head of the applicator. The liner assemblies can be located at suitable joints to limit or reduce deformation, movement, etc. of the liner assembly.

In some procedures, a contoured head is positioned over a liner assembly, which is positioned on a base unit, to clamp together components of the applicator. The liner assembly can be sucked against the entire cup surface for heating/cooling tissue such that the liner adheres to the cup. For example, the liner assembly can be adhered to sidewalls, bottom, or another portion of the cup. One or more holes can be formed (e.g., punched) along the liner assembly to establish vacuum pathways through the liner assembly. Filters, gel traps, and/or other features can be inserted into the holes to inhibit or prevent substances (e.g., cryoprotectants) from being sucked into components of the base unit. The vacuum can be reduced or stopped to place to place the applicator on a subject and then tissue can be suck into the applicator. Temperature sensors, contact sensors, and/or other sensors can be used to monitor, for example, temperatures (e.g., tissue temperatures, cup temperatures, etc.), the presence of tissue, tissue draw (e.g., movement of tissue, amount of tissue in the applicator, etc.), tissue retention, applicator operation, and so forth.

At least some methods for treating a subject's tissue include positioning one or more sealing members between a head and a base unit of an applicator. Optionally a liner assembly can be used that includes a liner that extends across an entrance of a tissue-receiving cavity of the applicator. A vacuum can be drawn in the tissue-receiving cavity to move an adhesive surface of the liner into physical contact with a conductive surface of the temperature-controlled cup. After adhering the liner to the conductive surface, the liner assembly can be perforated to establish fluid communication between at least one vacuum port of the applicator and the tissue-receiving cavity. This allows tissue to be pulled into the applicator via a vacuum.

Some of the embodiments disclosed herein can be for cosmetically beneficial alterations of target regions. Some cosmetic procedures may be for the sole purpose of altering a target region to conform to a cosmetically desirable look, feel, size, shape and/or other desirable cosmetic characteristic or feature. Accordingly, at least some embodiments of the cosmetic procedures can be performed without providing an appreciable therapeutic effect (e.g., no therapeutic effect). For example, some cosmetic procedures may not include restoration of health, physical integrity, or the physical well-being of a subject. The cosmetic methods can target subcutaneous regions to change a subject's appearance and can include, for example, procedures performed on subject's submental region, abdomen, hips, legs, face, neck, ankle region, or the like. In other embodiments, however, cosmetically desirable treatments may have therapeutic outcomes (whether intended or not), such as psychological benefits, alteration of body hormones levels (by the reduction of adipose tissue), etc.

Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, stages, or characteristics may be combined in any suitable manner in one or more examples of the technology. The headings provided herein are for convenience only and are not intended to limit or interpret the scope or meaning of the technology.

B. Cryotherapy

FIG. 1 and the following discussion provide a brief, general description of a treatment system 100 in accordance with some embodiments of the technology. The treatment system 100 can be a temperature-controlled system for exchanging heat with a subject 101 and can include a non-invasive tissue-cooling apparatus in the form of a cooling cup applicator 102 ("applicator 102") configured to selectively cool/heat tissue to reduce and/or eliminate targeted tissue, structures, or the like. The illustrated applicator 102 is positioned along a subject's hip and can be reconfigured to treat various sites. In some embodiments, applicator 102 has disposable or reusable components for contacting tissue, facilitating tissue draw into a base unit 103 of the applicator 102, preventing cross-contamination between patients, aiding in patient comfort, and/or affecting treatment by, for example, enhancing heat transfer, achieving desired temperature profiles, and so forth.

The treatment system 100 can perform medical treatments to provide therapeutic effects and/or cosmetic procedures for cosmetically beneficial effects. Without being bound by theory, selective effects of cooling are believed to result in, for example, membrane disruption, cell shrinkage, disabling, disrupting, damaging, destroying, removing, killing and/or other methods of lipid-rich cell alteration. Such alteration is believed to stem from one or more mechanisms acting alone or in combination. It is thought that such mechanism(s) trigger an apoptotic cascade, which is believed to be the dominant form of lipid-rich cell death by non-invasive cooling. In any of these embodiments, the effect of tissue cooling can be the selectively reduction of lipid-rich cells by a desired mechanism of action, such as apoptosis, lipolysis, or the like. In some procedures, the applicator 102 can cool the skin surface and/or targeted tissue to cooling temperature in a range of from about −25° C. to about 20° C. In other embodiments, the cooling temperatures can be from about −20° C. to about 10° C., from about −18° C. to about 5° C., from about −15° C. to about 5° C., or from about −15° C. to about 0° C. In further embodiments, the cooling temperatures can be equal to or less than −5° C., −10° C., −15° C., or in yet another embodiment, from about −15° C. to about −25° C. Other cooling temperatures and temperature ranges can be used.

Apoptosis, also referred to as "programmed cell death", is a genetically-induced death mechanism by which cells self-destruct without incurring damage to surrounding tissues. An ordered series of biochemical events induce cells to morphologically change. These changes include cellular blebbing, loss of cell membrane asymmetry and attachment, cell shrinkage, chromatin condensation and chromosomal DNA fragmentation. Injury via an external stimulus, such as cold exposure, is one mechanism that can induce cellular apoptosis in cells. Nagle, W. A., Soloff, B. L., Moss, A. J. Jr., Henle, K. J. "Cultured Chinese Hamster Cells Undergo Apoptosis After Exposure to Cold but Nonfreezing Temperatures" Cryobiology 27, 439-451 (1990).

One aspect of apoptosis, in contrast to cellular necrosis (a traumatic form of cell death causing local inflammation), is that apoptotic cells express and display phagocytic markers on the surface of the cell membrane, thus marking the cells for phagocytosis by macrophages. As a result, phagocytes can engulf and remove the dying cells (e.g., the lipid-rich cells) without eliciting an immune response. Temperatures that elicit these apoptotic events in lipid-rich cells may contribute to long-lasting and/or permanent reduction and reshaping of subcutaneous adipose tissue.

One mechanism of apoptotic lipid-rich cell death by cooling is believed to involve localized crystallization of lipids within the adipocytes at temperatures that do not induce crystallization in non-lipid-rich cells. The crystallized lipids selectively may injure these cells, inducing apoptosis (and may also induce necrotic death if the crystallized lipids damage or rupture the bi-lipid membrane of the adipocyte). Another mechanism of injury involves the lipid phase transition of those lipids within the cell's bi-lipid membrane, which results in membrane disruption or dysfunction, thereby inducing apoptosis. This mechanism is well-documented for many cell types and may be active when adipocytes, or lipid-rich cells, are cooled. Mazur, P., "Cryobiology: the Freezing of Biological Systems" Science, 68: 939-949 (1970); Quinn, P. J., "A Lipid Phase Separation Model of Low Temperature Damage to Biological Membranes" Cryobiology, 22: 128-147 (1985); Rubinsky, B., "Principles of Low Temperature Preservation" Heart Failure Reviews, 8, 277-284 (2003). Other possible mechanisms of adipocyte damage, described in U.S. Pat. No. 8,192,474, relate to ischemia/reperfusion injury that may occur under certain conditions when such cells are cooled as described herein. For instance, during treatment by cooling as described herein, the targeted adipose tissue may experience a restriction in blood supply and thus be starved of oxygen due to isolation as a result of applied pressure, cooling which may affect vasoconstriction in the cooled tissue, or the like. In addition to the ischemic damage caused by oxygen starvation and the buildup of metabolic waste products in the tissue during the period of restricted blood flow, restoration of blood flow after cooling treatment may additionally produce reperfusion injury to the adipocytes due to inflammation and oxidative damage that is known to occur when oxygenated blood is restored to tissue that has undergone a period of ischemia. This type of injury may be accelerated by exposing the adipocytes to an energy source (via, e.g., thermal, electrical, chemical, mechanical, acoustic, or other means) or otherwise increasing the blood flow rate in connection with or after cooling treatment as described herein. Increasing vasoconstriction in such adipose tissue by, e.g., various mechanical means (e.g., application of pressure or massage), chemical means or certain cooling conditions, as well as the local introduction of oxygen radical-forming compounds to stimulate inflammation and/or leukocyte activity in adipose tissue may also contribute to accelerating injury to such cells. Other yet-to-be understood mechanisms of injury may exist.

In addition to the apoptotic mechanisms involved in lipid-rich cell death, local cold exposure is also believed to induce lipolysis (i.e., fat metabolism) of lipid-rich cells and has been shown to enhance existing lipolysis which serves to further increase the reduction in subcutaneous lipid-rich cells. Vallerand, A. L., Zamecnik. J., Jones, P. J. H., Jacobs, I. "Cold Stress Increases Lipolysis, FFA Ra and TG/FFA Cycling in Humans" Aviation, Space and Environmental Medicine 70, 42-50 (1999).

One expected advantage of the foregoing techniques is that the subcutaneous lipid-rich cells in the target region can be reduced generally without collateral damage to non-lipid-rich cells in the same region. In general, lipid-rich cells can be affected at low temperatures that do not affect non-lipid-rich cells. As a result, lipid-rich cells, such as those associated with highly localized adiposity (e.g., adiposity along the abdomen, submental adiposity, submandibular adiposity, facial adiposity, etc.), can be affected while non-lipid-rich cells (e.g., myocytes) in the same generally region are not damaged. The unaffected non-lipid-rich cells can be located underneath lipid-rich cells (e.g., cells deeper than a subcutaneous layer of fat), in the dermis, in the epidermis, and/or at other locations.

In some procedures, the treatment system 100 can remove heat from underlying tissue through the upper layers of tissue and create a thermal gradient with the coldest temperatures near the cooling surface, or surfaces, of the applicator 102 (i.e., the temperature of the upper layer(s) of the skin can be lower than that of the targeted underlying target cells). It may be challenging to reduce the temperature of the targeted cells low enough to be destructive to these target cells (e.g., induce apoptosis, cell death, etc.) while also maintaining the temperature of the upper and surface skin cells high enough so as to be protective (e.g., non-destructive). The temperature difference between these two thresholds can be small (e.g., approximately, 5° C. to about 10° C., less than 10° C., less than 15° C., etc.). Protection of the overlying cells (e.g., typically water-rich dermal and epidermal skin cells) from freeze damage during dermatological and related aesthetic procedures that involve sustained exposure to cold temperatures may include improving the freeze tolerance and/or freeze avoidance of these skin cells by using, for example, cryoprotectants for inhibiting or preventing such freeze damage.

Tissue can be rapidly rewarmed as soon as practicable after a freeze event has occurred to limit, reduce, or prevent damage and adverse side effects associated with the freeze event. After freezing begins, tissue can be rapidly warmed as soon as possible to minimize or limit damage to tissue, such as the epidermis. In some procedures, tissue is partially or completely frozen for a predetermined period of time and then warmed. According to one embodiment, an applicator can warm shallow tissue using, for example, thermoelectric elements in the device. Thermoelectric elements can include Peltier devices capable of operating to establish a desired temperature (or temperature profile) along the surface. In other embodiments, the applicator outputs energy to warm tissue. For example, the applicator has electrodes that output radiofrequency energy for warming tissue. In some procedures, the applicator can be warmed at a rate of about 1° C./s, 2° C./s, 2.5° C./s, 3° C./s, 5° C./s, or other rate selected to thaw frozen tissue after the tissue has been partially or completely frozen for about 10 seconds, 30 seconds, 1 minute, 2 minutes, 5 minutes, 10 minutes, or other suitable length of time.

C. Treatment Systems

Figure 2:
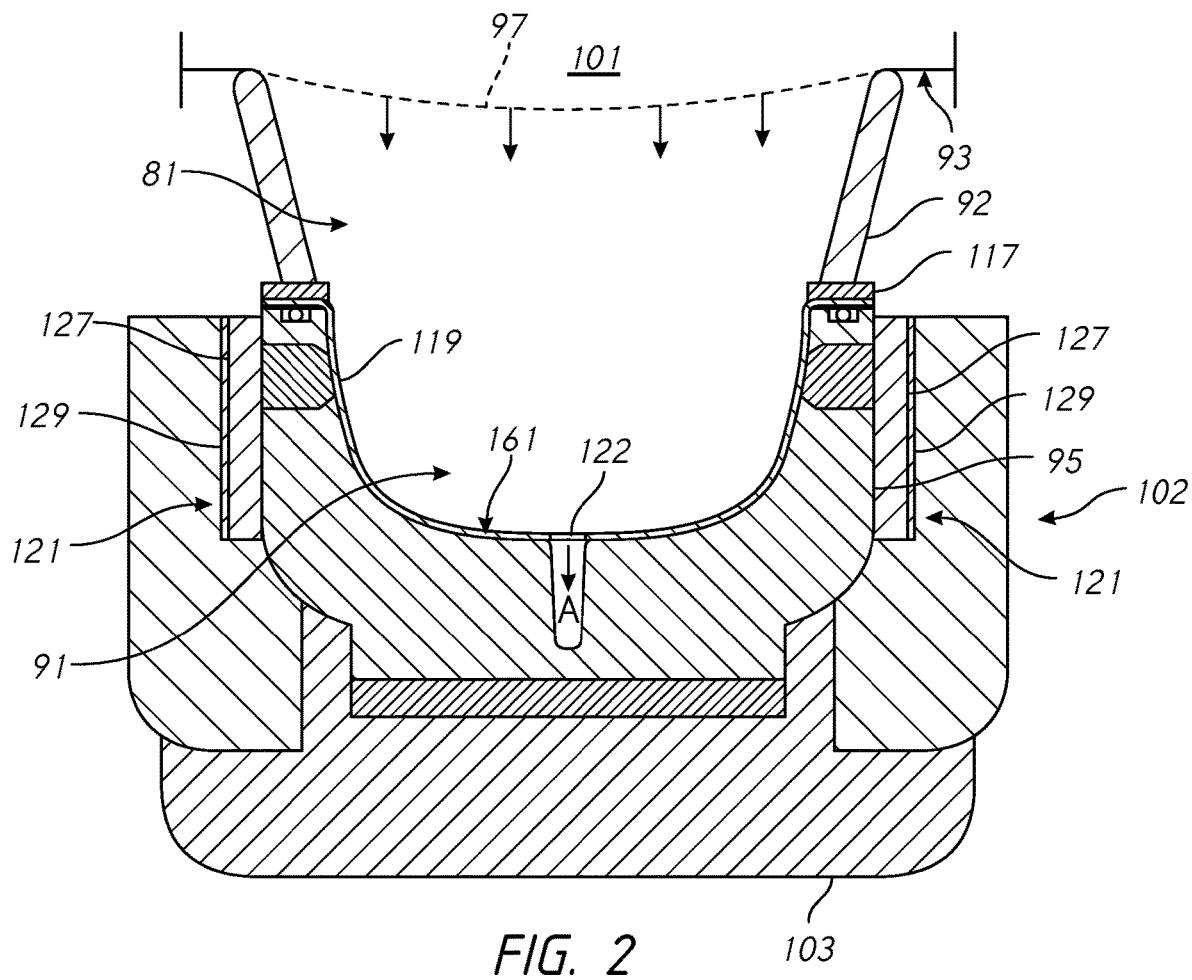
FIG. 2 is a cross-sectional view of an applicator taken along line 2-2 of FIG. 1.

FIG. 2 is a cross-sectional view of the applicator 102 taken along line 2-2 of FIG. 1. The applicator 102 includes a contoured head 92 ("head 92") and a liner assembly 117. The head 92 can conform closely to contours of the subject's body to sealingly engage a skin surface 93. The dashed line 97 shows the position of the tissue before being drawn (indicated by arrows) into a tissue-receiving cavity 81 of the applicator 102. An assortment of contoured heads can be used with the base unit 103, and each contoured head can correspond to a specific application and tissue size. The contoured heads can have different sizes and shapes to fit different body shapes. Accordingly, the single base unit 103 can be used with a set of contoured heads to perform treatments various sites along the subject.

The liner assembly 117 is configured to line a temperature-controlled three-dimensional conductive cup 95 ("cup 95"), which conductively cools tissue occupying a tissue-receiving cavity 91. The liner assembly 117 can include a flexible liner 119 that lines the cup 95. A vacuum can be drawn through an opening 122 in the liner 119 to draw tissue into and securely hold tissue in the tissue-receiving cavity 91. After establishing thermal contact between the tissue and the cup 95, the base unit 103 can cool/heat the retained tissue. Upon completion of the cryotherapy procedure, the applicator 102 can release the tissue (e.g., by reducing or stopping the vacuum) and can be used at another treatment site.

Most or substantially all of the skin surface of the volume of tissue in a cavity 91 is in thermal contact with the cup 95. The vacuum can be used to apply a generally uniform pressure to the subject's skin in the cavity 91. In some procedures, the tissue can contact a relative large contact area of the cup 95 to efficiently cool the entire volume of retained tissue. A vacuum can be sufficient to keep the tissue in contact with the bottom of the cup 95 so as to keep the cavity 81 filled with tissue while limiting or minimizing pooling of blood, vascular damage (e.g., rupturing of blood vessels), bruising, and other complications with folding tissue.

The base unit 103 can include cooling units 121 in thermal communication with a temperature-controlled heat-exchanging surface 161 of the cup 95. The cooling units 121 can include, without limitation, one or more thermoelectric elements 127 (e.g., Peltier-type elements), fluid-cooled elements 129, heat-exchanging units, or combinations thereof. In a cooling mode, a fluid-cooled element 129 can cool the backside of the thermoelectric elements 127 to keep the thermoelectric elements 127 at or below a target temperature. In a heating mode, the fluid-cooled element 129 can heat the backside of the thermoelectric elements 127 to keep the thermoelectric elements 127 at or above a target temperature. In some embodiments, the cooling units 121 include only fluid-cooled elements or only non-fluid cooled thermoelectric elements. The cooling unit 121 can be coupled to, incorporated into, or part of the cup 95. In some embodiments, the thermoelectric elements 121 can be embedded or otherwise disposed in the cup 95 to reduce the distance from the tissue to the thermoelectric elements.

Although the illustrated embodiment has two thermoelectric elements 121, it can have any desired number of thermoelectric elements. The number, positions, and operating temperatures of the cooling units 121 can be selected based on cooling/heating suitable for treatment. The configurations and components of the cooling units 121 can be selected based on the desired power consumption and target temperatures.

Figure 3:
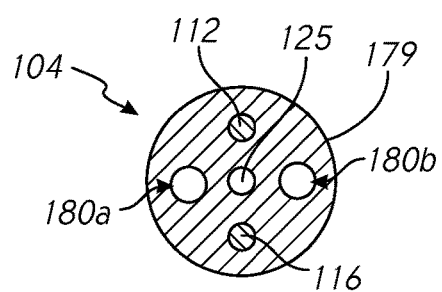
FIG. 3 is a cross-sectional view of a connector taken along line 3-3 of FIG. 1.

Referring again to FIG. 1, the connector 104 extends from the control module 106 to the applicator 102 and can provide suction for drawing tissue into the applicator 102 and energy (e.g., electrical energy) and fluid (e.g., coolant) from the control module 106 to the applicator 102. FIG. 3 is a cross-sectional view of the connector 104 taken along line 3-3 of FIG. 1 and shows the connector 104 including a main body 179, a supply fluid line or lumen 180a ("supply fluid line 180a"), and a return fluid line or lumen 180b ("return fluid line 180b"). The main body 179 may be configured (via one or more adjustable joints) to "set" in place for the treatment of the subject 101. The supply and return fluid lines 180a, 180b can be conduits comprising, in whole or in part, polyethylene, polyvinyl chloride, polyurethane, and/or other materials that can accommodate circulating coolant, such as water, glycol, synthetic heat transfer fluid, oil, a refrigerant, and/or any other suitable heat conducting fluid for passing through fluid-cooled element, such as the fluid-cooled elements 129 of FIG. 2 or other components. In one embodiment, each fluid line 180a, 180b can be a flexible hose surrounded by the main body 179.

The connector 104 can also include one or more electrical lines 112 for providing power to the applicator 102 and one or more control lines 116 for providing communication between the control module 106 (FIG. 1) and the applicator 102 (FIGS. 1 and 2). The electrical lines 112 can provide power to the thermoelectric elements (e.g., thermoelectric elements 127 of FIG. 2), sensors, and so forth. To provide suction, the connector 104 can include one or more vacuum lines 125. In various embodiments, the connector 104 can include a bundle of fluid conduits, a bundle of power lines, wired connections, vacuum lines, and other bundled and/or unbundled components selected to provide ergonomic comfort, minimize unwanted motion (and thus potential inefficient removal of heat from the subject), and/or to provide an aesthetic appearance to the treatment system 100.

The control module 106 can include a fluid system 105 (illustrated in phantom line), a power supply 110 (illustrated in phantom line), and a controller 114 carried by a housing 124 with wheels 126. The fluid system 105 can include a fluid chamber and a refrigeration unit, a cooling tower, a thermoelectric chiller, heaters, or any other device capable of controlling the temperature of coolant in the fluid chamber. The coolant can be continuously or intermittently delivered to the applicator 102 via the supply fluid line 180a (FIG. 3) and can circulate through the applicator 102 to absorb heat. The coolant, which has absorbed heat, can flow from the applicator 102 back to the control module 106 via the return fluid line 180b (FIG. 3). For warming periods, the control module 106 can heat the coolant that is circulated through the applicator 102. Alternatively, a municipal water supply (e.g., tap water) can be used in place of or in conjunction with the control module 106.

A pressurization device 123 can provide suction to the applicator 102 via the vacuum line 125 (FIG. 3) and can include one or more vacuum sources (e.g., pumps). Air pressure can be controlled by a regulator located between the pressurization device 123 and the applicator 102. The control module 106 can control the vacuum level to, for example, install the liner assembly and/or draw tissue into the applicator 102 while maintaining a desired level of comfort. If the vacuum level is too low, a liner assembly, tissue, etc. may not be drawn adequately (or at all) into and/or held within the applicator 102. If the vacuum level is too high when preparing the applicator, liner assembly can break (e.g., rupture, tear, etc.). If the vacuum level is too high during treatment, the patient can experience discomfort, bruising, or other complications. According to certain embodiments, approximately 0.5 inch Hg, 1 inch Hg, 2 inches Hg, 3 inches Hg, 5 inches Hg, 7 inches Hg, 8 inches Hg, 10 inches Hg, or 12 inches Hg vacuum is applied draw or hold the liner assembly 117, tissue, etc. Other vacuum levels can be selected based on the characteristics of the tissue, desired level of comfort, and vacuum leakage rates. Vacuum leak rates of the applicator 102 can be equal to or less than about 0.2, 0.5 LPM, 1 LPM, or 2 LPM at the pressure levels disclosed herein. For example, the vacuum leak rate can be equal to or less than about 0.2 LPM at 8 inches Hg, 0.5 LPM at 8 inches Hg, 1 LPM at 8 inches Hg, or 2 LPM at 8 inches Hg. The configuration of the pressurization device 123 and the applicator 102 can be selected based on the desired vacuum levels, leakage rates, and other operating parameters.

The power supply 110 can provide a direct current voltage for powering electrical elements of the applicator 102 via the line 112 (FIG. 3). The electrical elements can be thermal devices, sensors, actuators, controllers (e.g., a controller integrated into the applicator 102), or the like. An operator can use an input/output device in the form of a screen 118 ("input/output device 118") of the controller 114 to control operation of the treatment system 100, and the input/output device 118 can display the state of operation of the treatment system 100 and/or progress of a treatment protocol. In some embodiments, the controller 114 can exchange data with the applicator 102 via the line (e.g., link 116 of FIG. 3), a wireless communication link, or an optical communication link and can monitor and adjust treatment based on, without limitation, one or more treatment profiles and/or patient-specific treatment plans, such as those described, for example, in commonly assigned U.S. Pat. No. 8,275,442. The controller 114 can contain instructions to perform the treatment profiles and/or patient-specific treatment plans, which can include one or more segments, and each segment can include temperature profiles, vacuum levels, and/or specified durations (e.g., 1 minute, 5 minutes, 10 minutes, 20 minutes, 30 minutes, 1 hour, 2 hours, etc.). Additionally, if the treatment system 100 includes multiple applicators, a treatment profile can include specific profiles for each applicator to concurrently or sequentially treat multiple treatment sites, including, but not limited to, sites along the subject's torso, abdomen, legs, buttock, legs, face and/or neck (e.g., submental sites, submandibular sites, etc.), knees, back, arms, ankle region, or other treatment sites. In some embodiments, the controller 114 can be incorporated into the applicator 102 or another component of the treatment system 100.

D. Applicators

Figure 4:
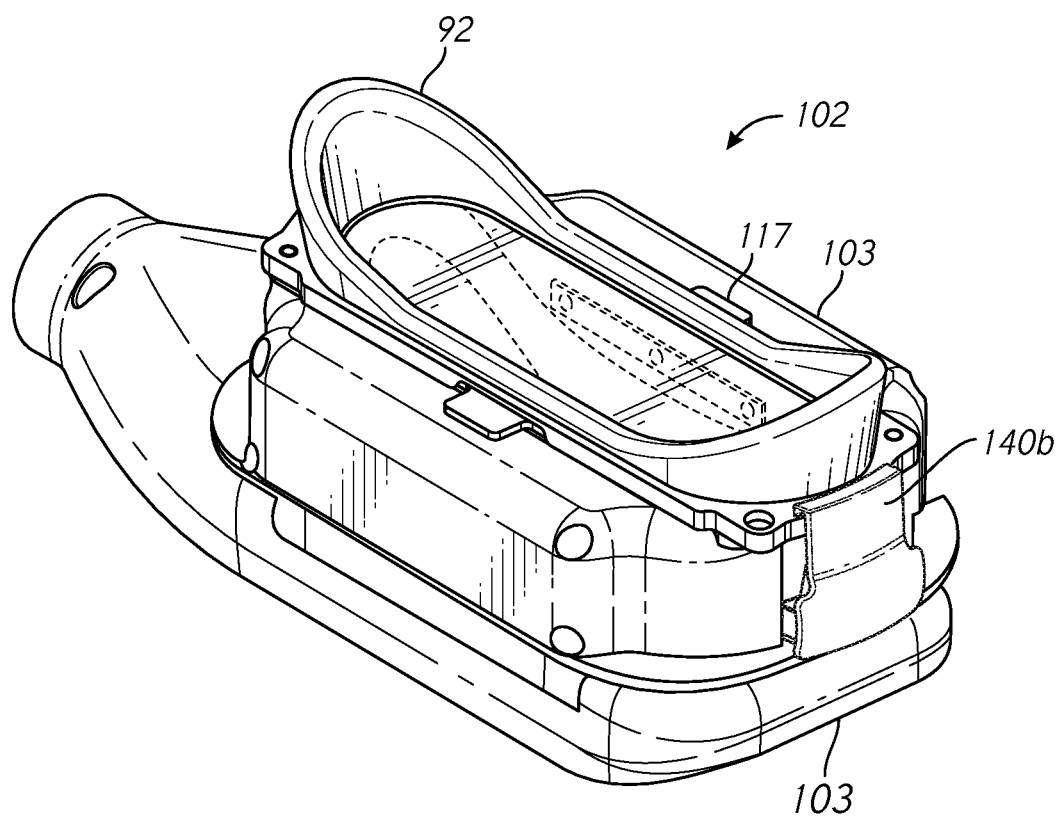
FIG. 4 is an isometric view of an applicator suitable for use with the system of FIG. 1 in accordance with an embodiment of the technology.
Figure 5:
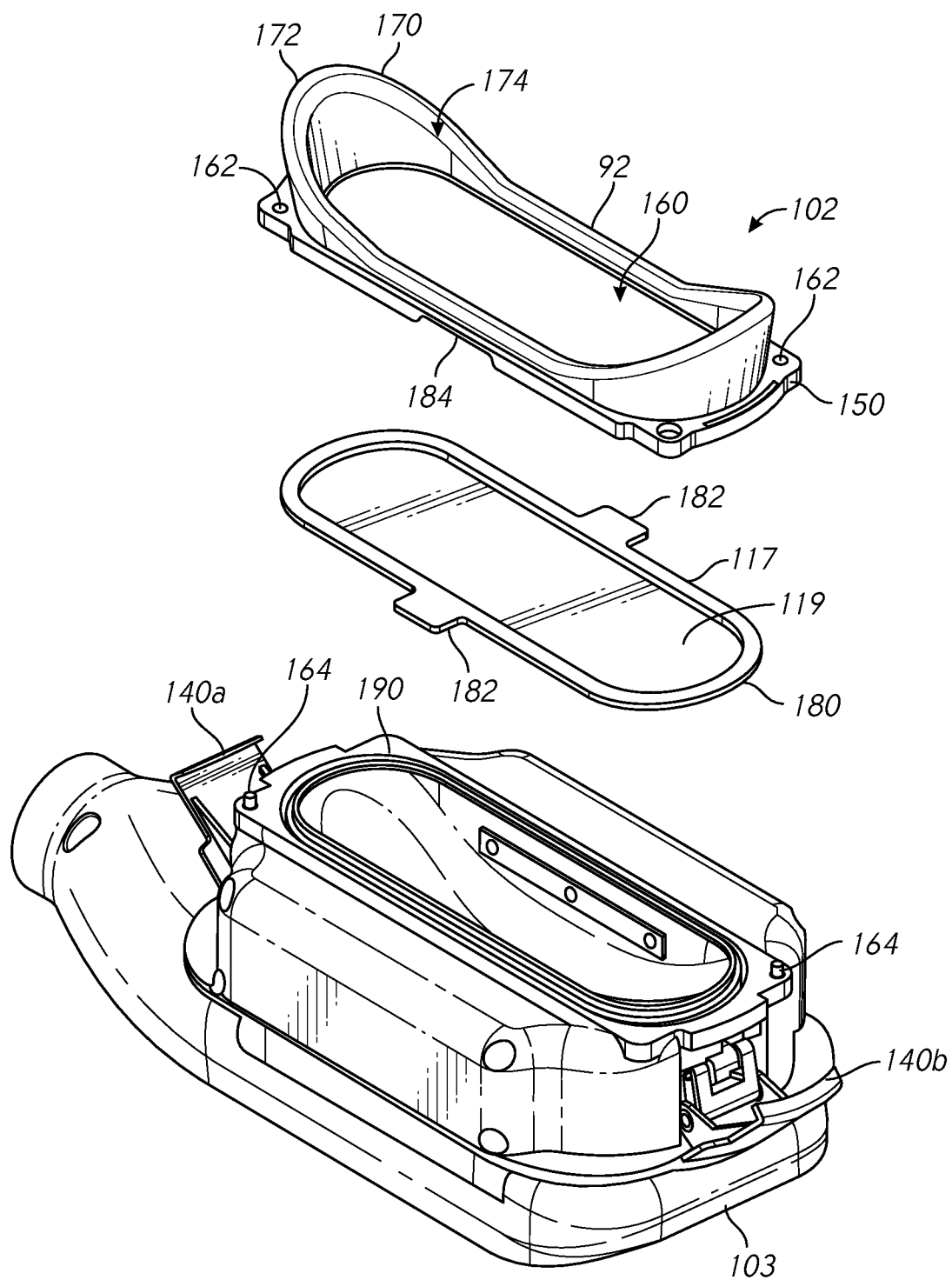
FIG. 5 is an exploded isometric view of the applicator of FIG. 4.

FIG. 4 is an isometric view of an applicator 102 ready to treat a subject. FIG. 5 is an exploded isometric view of the applicator 102 of FIG. 4 with the liner assembly 117 in a generally flat configuration. The base unit 103 includes latches 140a, 140b (collectively "latches 140") that can clamp the contoured head 92 to the base unit 103. When the base unit 103 is in a locked configuration, the liner assembly 117 can be securely held between the contoured head 92 and the base unit 103. The base unit 103, line assembly 117, and contoured head 92 can sealing engage one another. Various embodiments of the applicator 102 are discussed in connection with FIGS. 6-17F.

Figure 6:
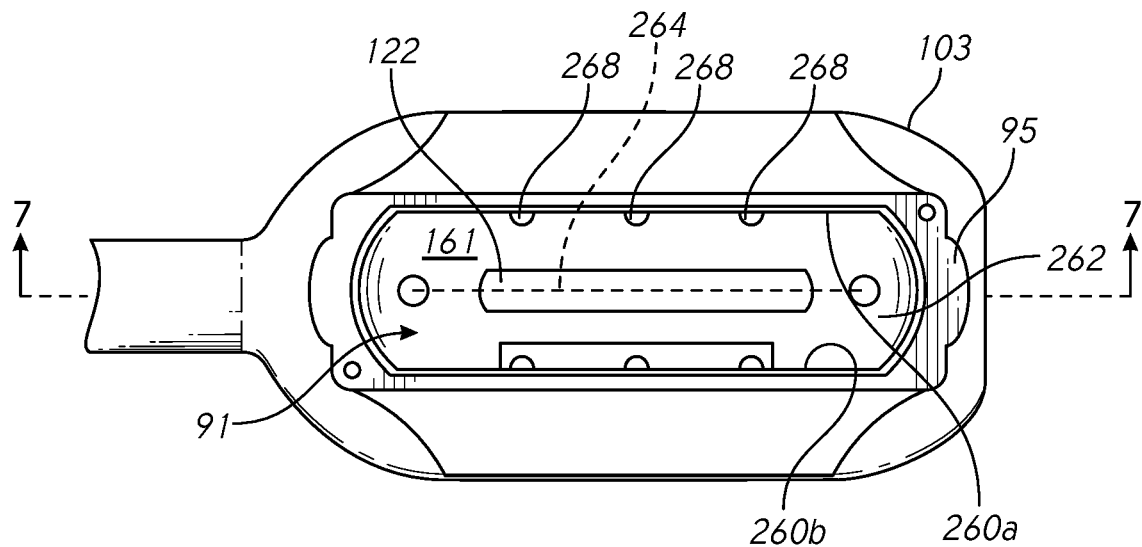
FIG. 6 is a top view of a base unit of an applicator in accordance with an embodiment of the technology.

FIG. 6 is a top view of the base unit 103 with the cup 95 capable of cooling from all directions to uniformly cool targeted tissue. The temperature-controlled heat-exchanging surface 161 ("surface 161") can be a smooth contoured surface that extends continuously along at least most of the cavity 91. When tissue is drawn against the surface 161, the tissue can be slightly stretched to reduce the thickness of the skin to increase heat transfer between targeted tissue and the surface 161. The cup 95 can comprise one or more thermally conductive materials, including, without limitation, metal (e.g., aluminum, stainless steel, pure copper, copper alloys, etc.) or other rigid or flexible high heat transfer materials, such as thermally conductive plastics. In some embodiments, the thermally conductive material of the cup 95 at room temperature has a thermal conductivity equal to or greater than about 25 W/(mK), 50 W/(mK), 100 W/(mK), 200 W/(mK), 300 W/(mK), 350 W/(mK), and ranges encompassing such thermal conductivities. The cup 95 can have a multi-piece construction with various pieces made of materials selected to provide different amounts of heat flow at different locations. In other embodiments, the cup 95 has a unitary construction and is made of a single material, such as metal.

The cup 95 can include sidewalls 260a, 260b and a bottom 262. A positive draft angle of the sidewalls 260a, 260b can be increased or decreased to decrease or increase, respectively, the vacuum level needed to fill the cavity 91 with tissue. A shown in FIG. 7, the bottom 262 can define a curved longitudinal profile shape in a longitudinal direction (e.g., a direction parallel to the axis 264 in FIG. 6), and the bottom of the cavity 91 can define a curved transverse profile shape in a transverse direction, as shown in FIG. 2. Tissue-receiving cavities disclosed herein can have substantially U-shaped cross sections (see cavity 91 cross section shown in FIG. 2), V-shaped cross sections, or partially circular/elliptical cross-sections, as well as or other cross sections suitable for receiving tissue. Thus, the thermal properties, shape, and/or configuration of the cup 95 can be selected based on, for example, target treatment temperatures and/or volume of the targeted tissue.

The cavity 91 can have a substantially uniform depth along most of longitudinal axis (e.g., longitudinal axis 264 of FIG. 6). Embodiments of the base unit 103 for treating large volumes of tissue (e.g., adipose tissue along the abdomen, hips, buttock, etc.) can have a maximum depth 266 (FIG. 7) equal to or less than about 2 cm, 5 cm, 10 cm, 15 cm, or 20 cm, for example. Embodiments of the base unit 203 for treating small volumes (e.g., a small volume of submental tissue) can have a maximum depth 266 equal to or less than about 0.5 cm, 2 cm, 2.5 cm, 3 cm, or 5 cm, for example. The maximum depth of the cup cavity 91 can be selected based on, for example, the volume of targeted tissue, characteristics of the targeted tissue, and/or desired level of patient comfort.

Referring again to FIG. 6, the cup 95 can include one or more vacuum ports in fluid communication with the cavity 91. Vacuum ports can be positioned along the sidewalls 260, bottom 262, or other suitable location along the cup 95. In some embodiments, an elongated vacuum port 122 (e.g., a slot vacuum port) is positioned near or at the bottom of the cavity 91 to comfortably draw tissue into thermal contact with the cup bottom 262, as well as the sidewalls 260. The number and locations of the vacuum ports can be selected based on, for example, considerations of patient comfort, desired vacuum levels, and/or other treatment parameters.

Sensors 268 can be temperature sensors, such as thermistors, positioned to detect temperature changes associated with warm tissue being drawn into and/or located in the cup 95. A control module (e.g., control module 106 of FIG. 1) can interpret the detected temperature increase associated with skin contact and can monitor, for example, the depth of tissue draw, tissue, freezing, thawing, or the like. In some embodiments, the sensors 268 measure heat flux and/or pressure (e.g., contact pressure) with the skin of the patient and can be positioned along the sidewalls 260, bottom 262, or other suitable locations. In yet further embodiments, the sensors 268 can be tissue impedance sensors, contact sensors, or other sensors used to determine the presence of tissue and/or whether tissue has been adequately drawn into the applicator so as to completely fill the cavity 91 to achieve a suitable level of thermal contact, limit or reduce voids or gaps, and/or hold tissue while limiting or reducing, for example, pooling of blood, discomfort, and so forth.

Sensor feedback can be collected in real-time and used in concert with treatment administration to efficaciously target specific tissue. The sensor measurements can also indicate other changes or anomalies that can occur during treatment administration. For example, an increase in temperature detected by the sensors 268 can indicate either a freezing event at the skin or movement of the applicator 102. An operator can inspect the subject's skin and/or applicator 102 in response to a detected increase in temperature. Methods and systems for collection of feedback data and monitoring of temperature measurements are described in commonly assigned U.S. Pat. No. 8,285,390.

Figure 7:
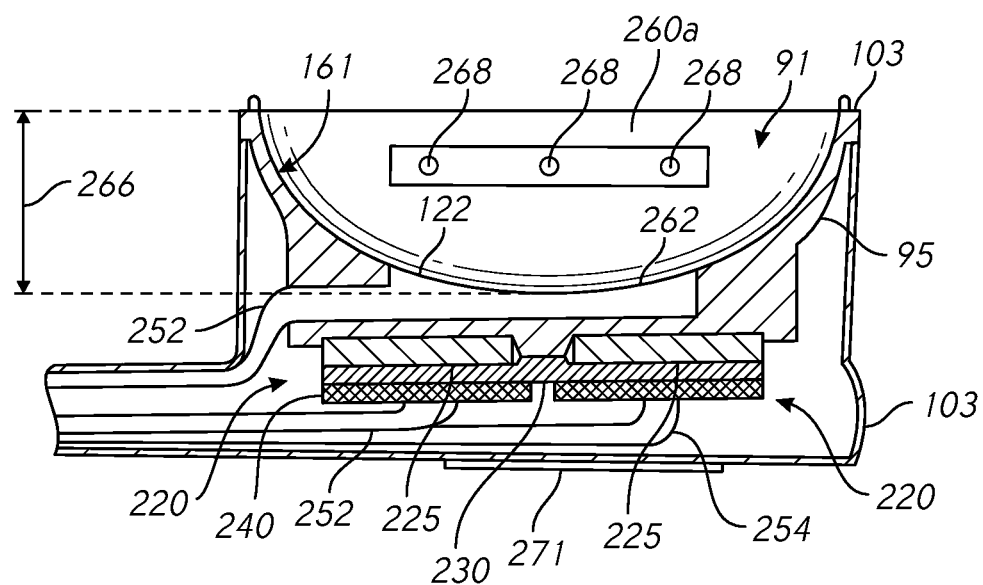
FIG. 7 is a cross-sectional view of the base unit taken along line 7-7 of FIG. 6 in accordance with an embodiment of the technology.

FIG. 7 is a cross-sectional view of the base unit 103 taken along the line 7-7 of FIG. 6 in accordance with one embodiment. As discussed in connection with FIG. 2, the sides of the cup 95 can be cooled. FIG. 7 shows an embodiment with cooling units 220 mounted directly to or incorporated into the cup 95. The cooling units 220 can include one or more thermal devices 225, fluid cooled devices 230, and connection assemblies 240. The thermal devices 225 can include, without limitation, one or more thermoelectric elements (e.g., Peltier-type elements), fluid-cooled elements, heat-exchanging units, or combinations thereof. In some embodiments, the applicator 102 includes only fluid-cooled elements or only non-fluid cooled thermoelectric elements. The connection assemblies 240 can include circuitry, a circuit board, fittings (e.g., inlet ports, outlet ports, etc.), or the like and can be connected to lines 252, 254. The lines 252, 254 can deliver coolant to and from the fluid cooled devices 230.

Other configurations and components of the applicator 102 can be selected to achieve suitable power consumption and cooling/heating capability.

The base unit 103 can also include an integrated controller with an input/output device 271 (e.g., a U/I touchpad) used by an operator to control operation the applicator 102. The input/output device 271 can include buttons, switches, screens, or the like and display information. The displayed information can include treatment plan information, sensor readings (e.g., skin temperatures, cup temperatures, etc.), vacuum level, and so forth.

Figure 8:
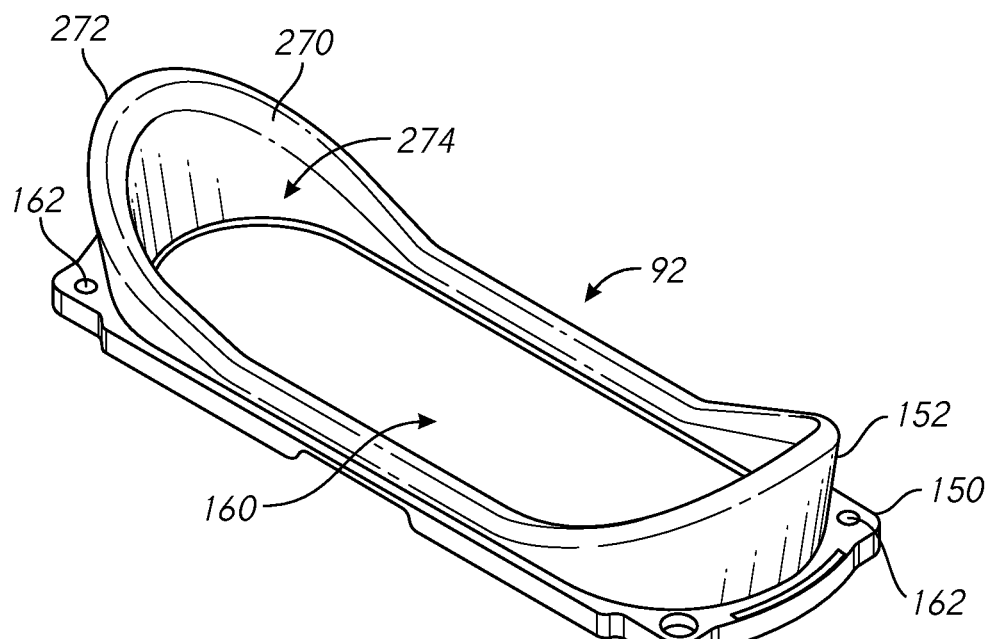
FIG. 8 is an isometric view of a contoured head in accordance with an embodiment of the technology.
Figure 9:
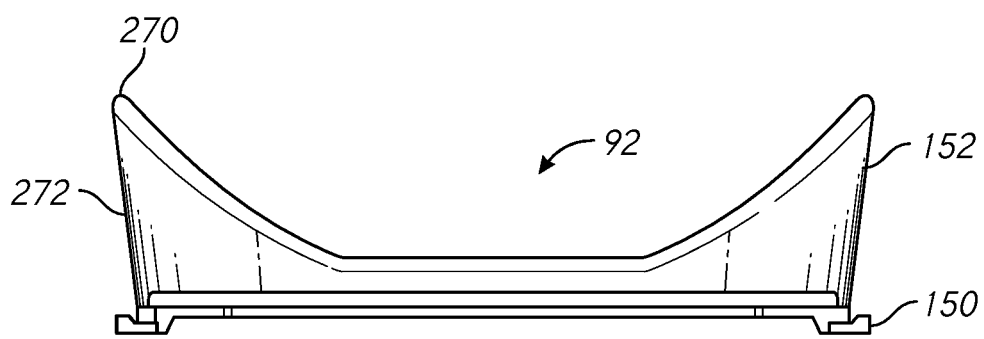
FIG. 9 is a side view of the head of FIG. 8.
Figure 10:
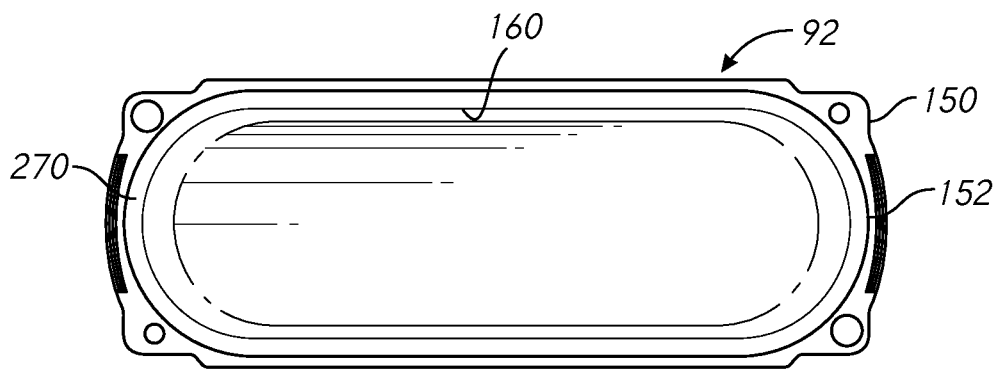
FIG. 10 is a top view of the head of FIG. 8.

FIGS. 8, 9, and 10 are an isometric view, a side view, and a top view of the contoured head 92. The head 92 can include a mounting body or frame 150 and a contoured mouth 152. The mounting body 150 is configured to surround an entrance of the tissue-receiving cavity (e.g., cavity in FIG. 91) and defines an opening 160 with a shape complementary to the underlying tissue-receiving cavity. The mounting body 150 can include one or more alignment features 162 configured to engage corresponding alignment features (e.g., alignment features 164 in FIG. 5) along the base unit 103. The alignment features 162 can be, for example, pins, apertures, recesses, dimples, magnets, ferrous elements (e.g., elements comprising ferrous material), and the alignment features 164 (FIG. 5) can be openings, protrusions, pins, and magnets. The number, types, and positions of the alignment features can be selected to achieve the desired positioning of the head 92 to limit or minimize offset edges on, for example, the inside of the cup 95. Multiple alignment features can cooperate to ensure that the applicator can withstand pressure and applied torques when applied to the subject. In various embodiments, contoured heads can be attached to the base unit 103 and/or liner assembly 117 via pins, clamps, magnets, screws, or other coupling means. Coupling features of the head 92 can extend through or into the liner assembly to inhibit or limit movement of the liner assembly with respect to, for example, the base unit 103 and/or the contoured head 95. In other embodiments, coupling features can couple the contoured head 92 directly to the base unit.

The mouth 152 can include a contoured lip 270 and a body 272. The lip 270 can define an entrance 274 and can be configured to sealingly engage, for example, the subject's skin. The lip 270 can have a rounded or curved cross-sectional shape for forming airtight seals with the subject's skin and can be made, in whole or in part, of silicon, rubber, soft plastic, or other suitable highly compliant materials. The mechanical properties, thermal properties, shape, and/or dimensions of the contoured lip 270 can be selected based on, for example, whether the contoured lip 270 contacts the subject's skin, liner assembly, a cryoprotectant gel pad, or the like. The body 272 is coupled to the frame 150 and can comprise a compliant material to allow the contoured mouth 252 expand or contract. When a vacuum is initially drawn into the mouth 252, the body 272 can deform inwardly due to the vacuum. As a tissue is pulled through the mouth 252 and toward the cup 95, the body 272 can deflect outwardly.

The frame 150 can be made, in whole or in part, of metal, plastic, rubber, combinations thereof, or the like. In some embodiments, the frame 150 comprises plastic and metal stiffeners (e.g., a steel rim) and is shaped to overlie a mounting region of the cup.

Figure 11:
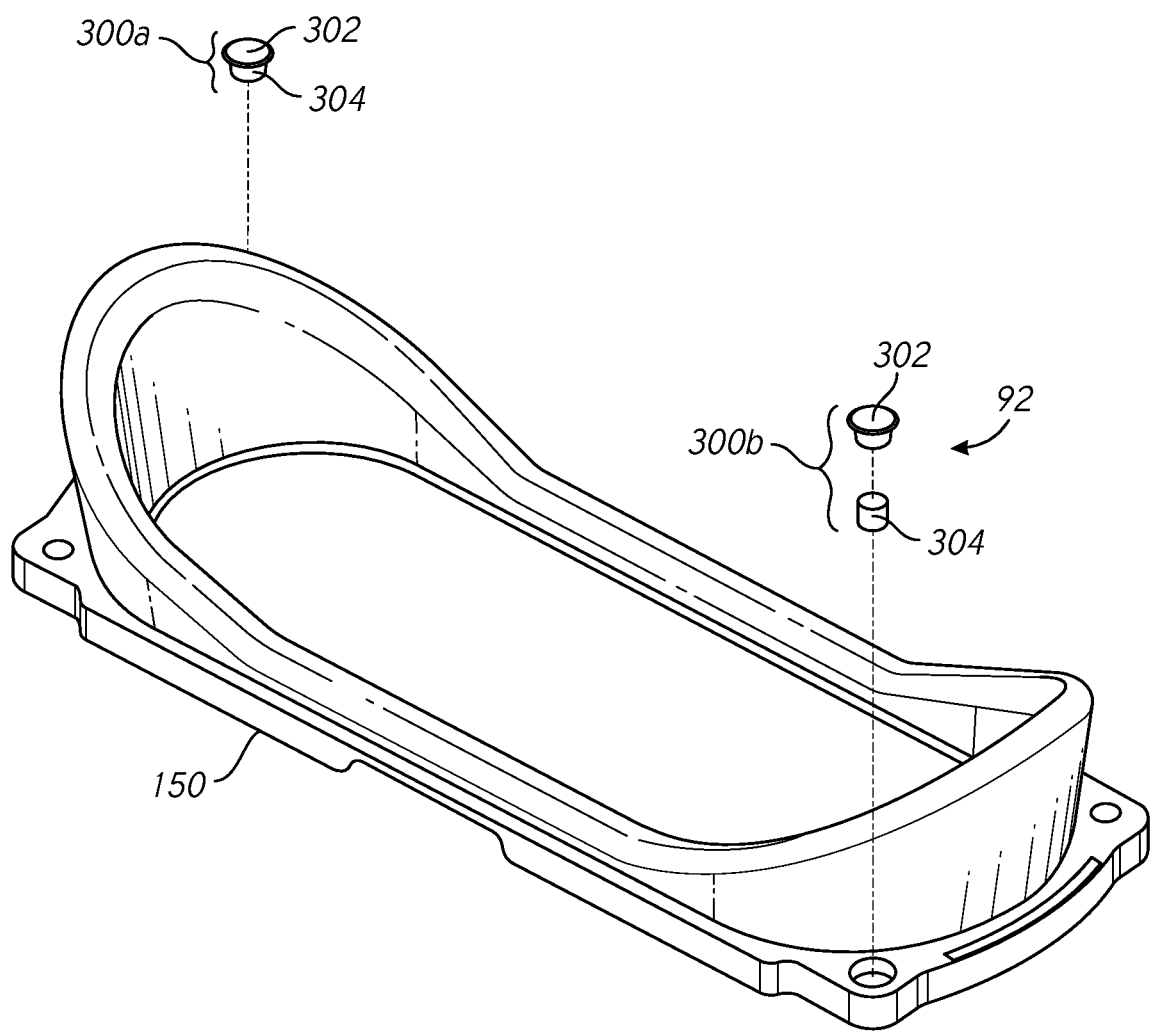
FIG. 11 is an exploded isometric view of a contoured head in accordance with an embodiment of the technology.

FIG. 11 is an exploded isometric view of the head 92 in accordance with one embodiment. The head 92 can include one or more sensing assemblies 300a, 300b (collectively "sensing assemblies 300") configured to provide information to, for example, the base unit, the treatment system 100, or other component, and/or to any entity having a communication link with the base unit, treatment system or other component. (The sensing assembly 300a is shown assembled, and the sensing assembly 300b is shown exploded.) Based on output from the sensing assemblies 300, the system 100 can determine, for example, the presence and/or type of contoured head.

Magnetic sensing can provide accurate detection without problems associated with mechanical sensors malfunctioning, even when used with cryotherapy gels (e.g., cryoprotectant gels, temperature-dependent substances, etc.). Each sensing assembly 300 can include a cap 302 and a magnetic element 304. When the cap 302 is installed, its orientation with respect to the frame 150 can indicate information about the head 92. The magnetic element 304 can be sensed by the base unit 103 to obtain information about the presence of the head 92, position of the head 92, information about the head 92 (e.g., type of head) and so forth. Information about the type of head being used can be communicated by the treatment system 100 to its manufacturer so the manufacturer can track usage of various heads and track any failures or treatment malfunctions or treatment parameters and treatment results associated with any head to better track and improve product performance. Once the contoured head 92 is installed, one or more sensors, detectors, readers of the base unit can determine the position of the magnetic element 304, which can correspond and communicate the type of head being used and optionally other information associated with or regarding the head being used. In various embodiments, the head 92 can include, without limitation, labels, barcodes, tags (e.g., radio frequency identification tags), or other devices capable of being read by, for example, a label reader, a barcode reader, communication device (e.g., sensing assemblies, transmitters, tags, etc.), or other component of the applicator 102.

Figure 12:
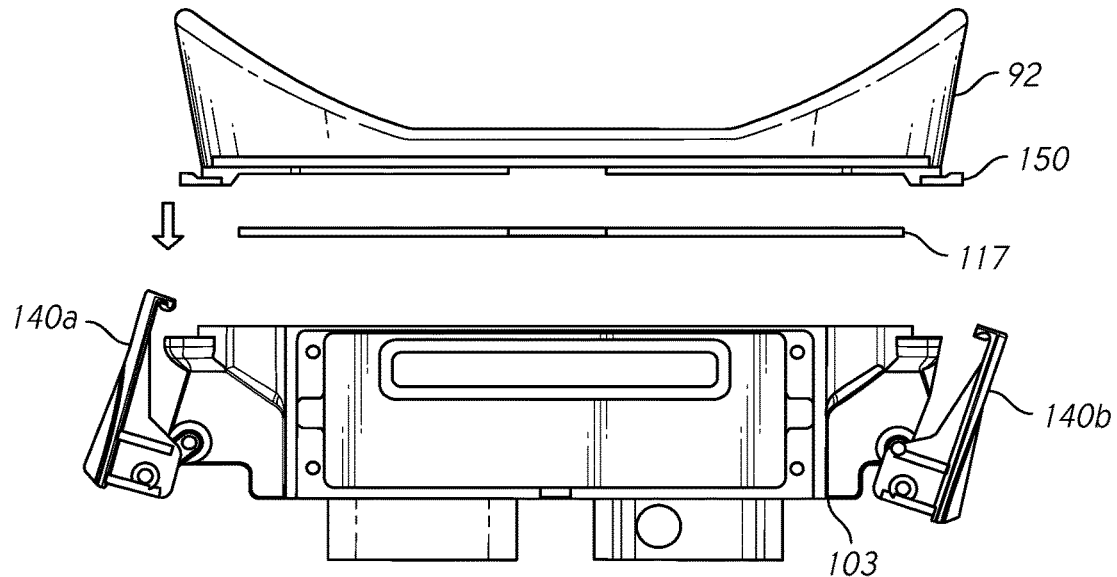
FIG. 12 is a side view of a contoured head, a liner assembly, and a base unit ready for assembly in accordance with an embodiment of the technology.
Figure 13:
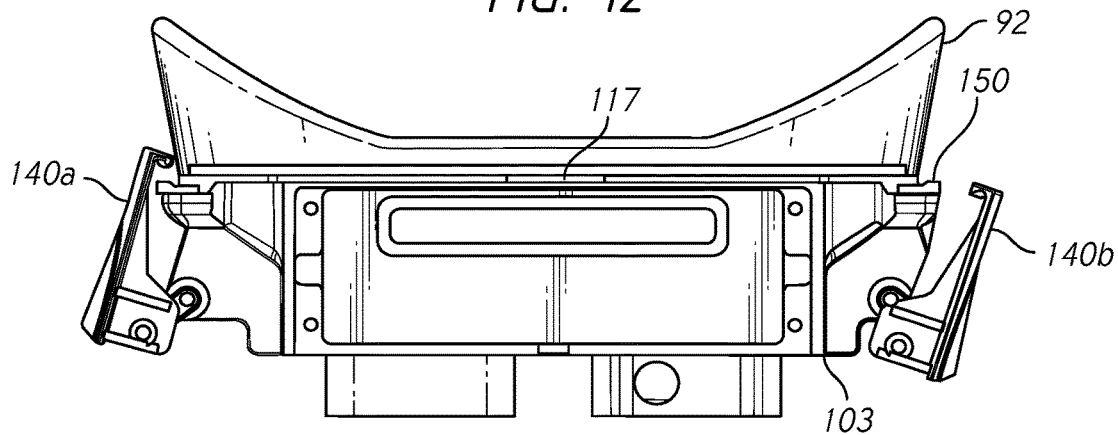
FIG. 13 is a side view of the head and liner assembly placed on the base unit in an unlocked configuration.
Figure 14:
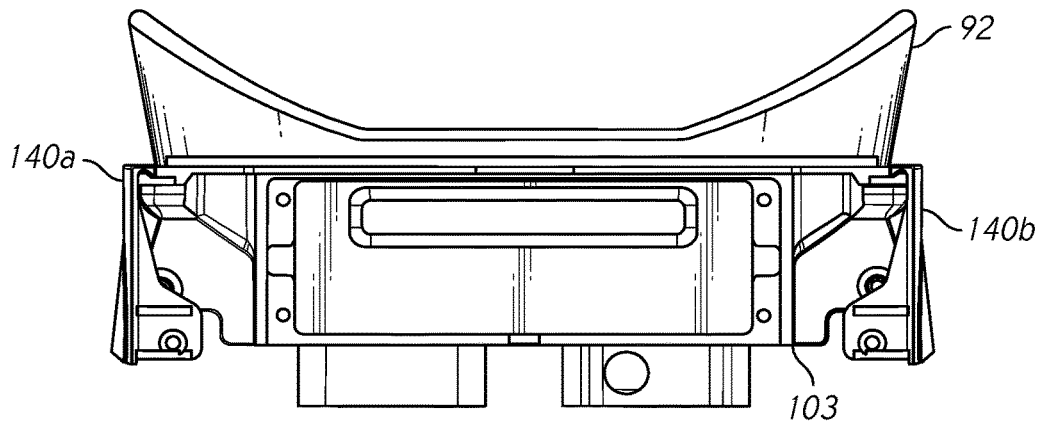
FIG. 14 is a side view of the installed head and liner assembly with the base unit in a locked configuration.

FIG. 12 is a side view of the contoured head 92 ready to be installed on a portion of the base unit 103. FIG. 13 is a side view of the base unit 103 in an unlocked configuration after the head 92 and liner assembly 117 have been placed on the base unit 103. FIG. 14 is a side view of the base unit 103 in a locked configuration. Referring now to FIG. 12, the base unit 103 has rotatable latches 140a, 140b positioned to allow installation of the head 92 and liner assembly 117. The latches 140a, 140b can be used to hold various types of contoured heads with, for example, geometrically congruent mounting bodies or frames. The latches 140a, 140b can include, without limitation, one or more biasing members (e.g., springs), stops, alignment guides, or the like. The configuration and operation of the latches can be selected based on the desired ease of installing and removing components.

Referring now to FIG. 13, the latches 140a, 140b can be operated to pull the frame 150 of the head 92 toward the base unit 103 as the latches 140a, 140b are moved to locked positions. FIG. 14 shows the latches 310a, 310b in locked positions. The latches 140a, 140b can apply sufficient compressive forces to the contoured head 92 to establish sealing (e.g., hermetic sealing) between mated components. To release the head 92 and liner assembly 117, the latches 140a, 140b can be moved back to the unlocked positions.

During a treatment session, contoured heads, line assemblies, and other components can be quickly replaced any number of times. Other types of heads, contours, and engagement features can be attached to the base unit 103. For example, contour elements disclosed in U.S. Publication 2010/0280582 can be used with the base unit 103, which may have magnets or other alignment features and can provide desired sealing, including generally air-tight seal cincturing. U.S. Publication 2010/0280582 is incorporated by reference in its entirety.

Figure 15:
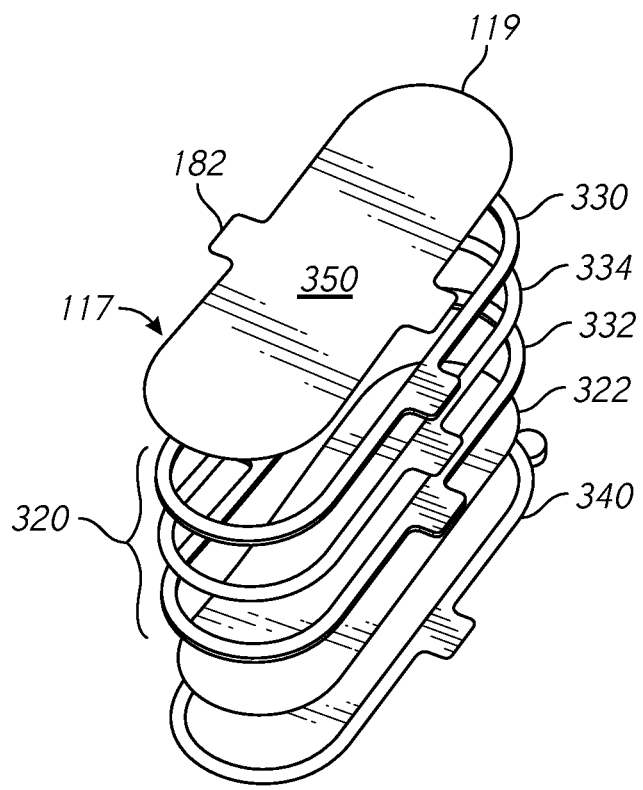
FIG. 15 is an exploded isometric view of a liner assembly in accordance with an embodiment of the technology.
Figure 16:
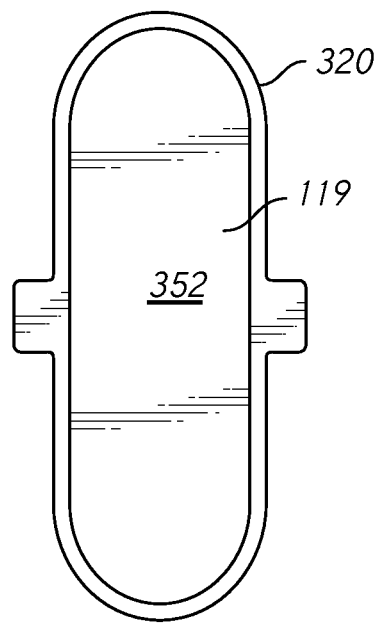
FIG. 16 is a bottom view of the liner assembly of FIG. 15.

FIG. 15 is an exploded isometric view of the liner assembly 117 in accordance with one embodiment of the technology. FIG. 16 is a bottom view of the liner assembly 117. Referring now to FIG. 15, the liner assembly 117 can include the liner 119, sealing member or gasket 320, a release liner 322, and a carrier 340. The liner 119 can be a flexible sheet or film made, in whole or in part, of urethane, nylon, rubber, silicon, Tegaderm™ or the like and can include tabs 182 (one identified). In some embodiments, the liner 119 is a transparent sheet that provides viewing of the underlying cup. To maintain normal skin function, the liner 119 can be air permeable to allow air to reach the skin while allowing moisture (e.g. moisture vapor) to escape. Such liner 119 can optionally be impermeable to substances (e.g., cryoprotectant gels, thermal coupling gels, etc.) used during therapy to keep the applied substances from clogging vacuum lines.

The liner 119 has a patient-contact surface 350 (FIG. 15) suitable for contacting the subject's skin and an opposing cup-contact surface 352 (FIG. 16). The cup-contact surface 352 can be an adhesive surface comprising, in whole or in part, acrylic adhesive, pressure-sensitive adhesive, butyl rubber, silicone rubber, and/or other adhesives. In multilayer embodiments, the liner 119 comprises a flexible polymer layer and an adhesive layer formed by applying adhesive via spraying, dipping process, or other suitable techniques. The number and compositions of the layers can be selected based on the desired characteristics of the liner 119. In other embodiments, the liner 119 can be a monolayer sheet that is adhered to the cup by an adhesive which has been applied to the cup.

Referring again to FIG. 15, the sealing member 320 can include compliant members 330, 332 and an intermediate layer 334. The compliant members 330, 332 can comprise, in whole or in part, foam (e.g., closed cell foam), rubber, silicon, or combinations thereof. The intermediate layer 334 can couple together the compliant members 330, 332. In other embodiments, the sealing member 320 can be a monolayer gasket made, in whole or in part, of urethane, rubber, silicon, or combinations thereof suitable for forming seals (e.g., air-tight seals or other desired seals). In some embodiments, the sealing member 320 can include, without limitation, one or more stiffeners to help maintain the shape of the liner assembly during, for example, installation. For example, the intermediate layer 334 can be a rigid metal or plastic layer. In some embodiments, the sealing member 320 can be relatively stiff compared to the liner 119 to, for example, help install the liner 119. The frame 150 can be relative stiff compared to the compliant members 330, 332 such that the sealing member 320 is sufficiently compliant for forming vacuum seals maintained during and/or after tissue draw.

Figure 17A:
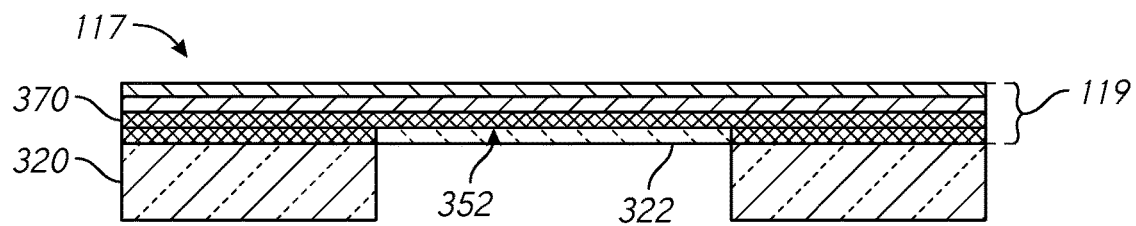
FIGS. 17A-17F show stages of a method for assembling an applicator in accordance with an embodiment of the technology.

FIGS. 17A-17F show stages of a method for preparing an applicator in accordance with an embodiment of the disclosed technology. FIG. 17A is a cross-sectional schematic view of the liner assembly 117 ready to be installed. An adhesive 370 couples the liner 119 and the gasket 320. The release liner 322 can be removed from the liner 119 to expose the adhesive cup-contact surface 352 ("adhesive surface 352").

Figure 17B:
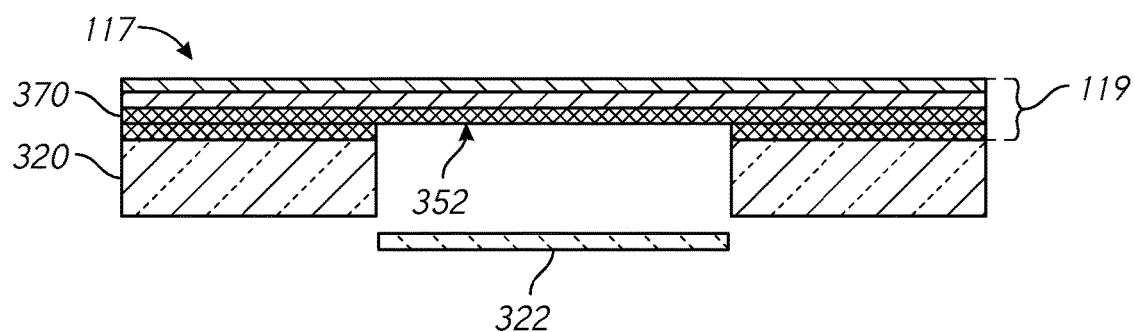

FIG. 17B shows the release liner 322 spaced apart from the adhesive surface 352. The release liner 322 can be discarded, and the liner assembly 117 can be placed on the base unit 103.

Figure 17C:
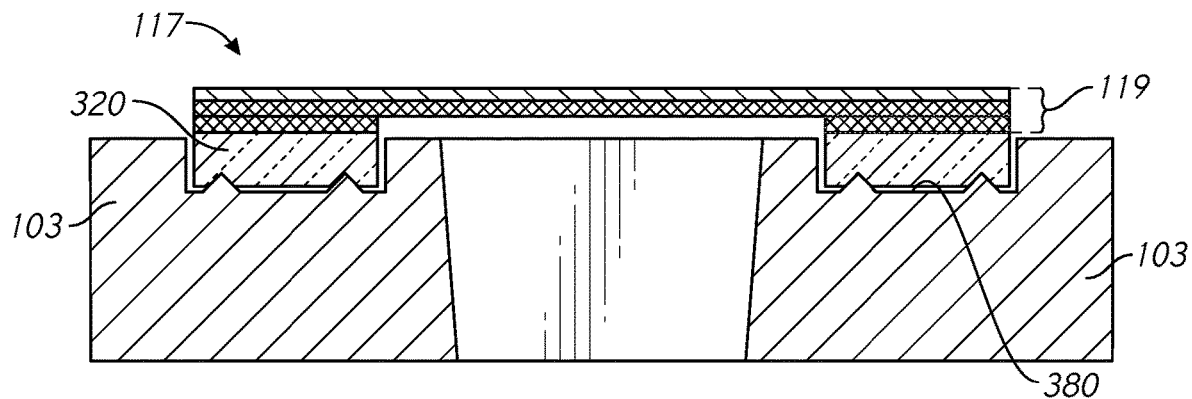

FIG. 17C shows the gasket 320 positioned in a receiving feature 380 in the base unit 103. The receiving feature 380 can be a trench, a recess, a channel, or other feature suitable for receiving at least a portion of the liner assembly 117. Other arrangements can be used to position the gasket 320 with respect to the base unit 103, as well as limiting movement of the liner assembly 117 with respect to the base unit 103 during use.

Figure 17D:
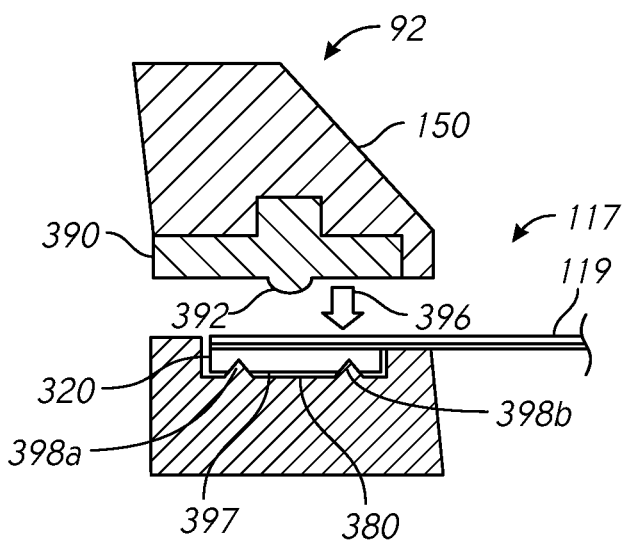

FIG. 17D shows a portion of the frame 150 ready to be placed on the liner assembly 117, illustrated schematically. The frame 150 can include an engagement member 390 with a protrusion 392 that cooperates with ridges 398a, 398b (collectively "ridges 398") to provide desired sealing. The protrusion 392 can have a curved or semi-circular cross section, and the ridges 398 can have V-shaped cross sections, U-shaped cross sections, or other suitable configuration. The frame 150 can be moved downwardly, as indicated by arrow 396, to compress a section 397 of the gasket 320 located between ridges 398a, 398b of the receiving feature 380. Other arrangements can be used to achieve the desired sealing capability.

Figure 17E:
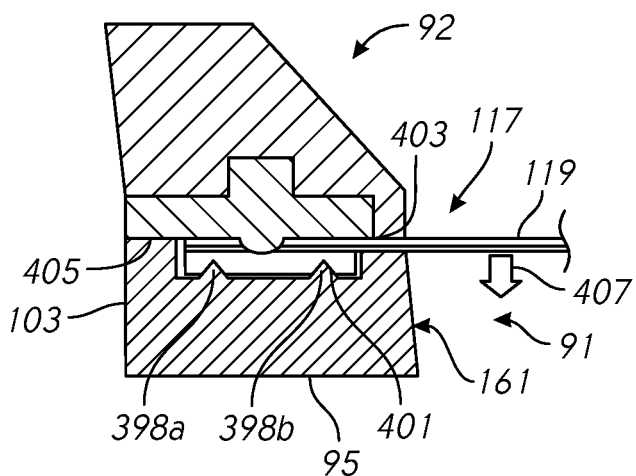

FIG. 17E shows the contoured head 92 and liner assembly 117 installed on the base unit 103 such that the liner 119 extends across a tissue-receiving cavity 91 to form a closed chamber. As discussed in connection with FIGS. 12-14, the base unit 103 can be operated to clamp onto the liner assembly 117. Accordingly, the base unit 103 can pull the head 92 against the liner assembly 117 to form and maintain a seal 401 (e.g., a hermetic seal) between, for example, the liner assembly 117 and the base unit 103, a seal 403 between the liner assembly 117 and the contoured head 92, a seal 405 between the head 92 and the base unit 103, and/or additional seals.

Figure 17F:
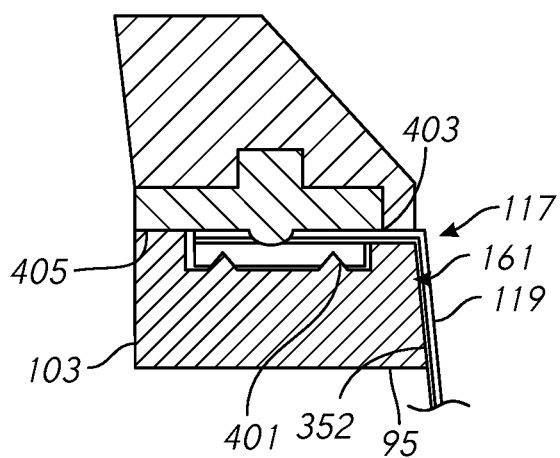

The base unit 103 can suck the liner 119 into the cavity 91 (indicated by arrow 407) and then against the conductive surface 161. Because the liner 119 is positioned directly over the cavity 91, it deforms less than liners or sleeved applied to the outside of applicators. As shown in FIGS. 17E and 17F, the liner 119 does not need to contact and conform to the lip of the mouth, so that liner assembly 117 can be used independent of the configuration of contoured head.

FIG. 17F shows the liner 119 after the adhesive surface 352 has been pulled against the conductive surface 161. The head 92 holds the periphery of the linear assembly 117 to keep the liner 119 aligned with the cup 95. A user can manually press the liner 119 against the surface 161 to remove trapped air, close gaps or voids, or otherwise apply the liner 119. Various techniques can be used to line the temperature-controlled cup 95 with the liner 119.

The liner 119 can overlie most or substantially the entire thermally conductive surface 161. In some procedures, the liner 119 covers all of the exposed surfaces of the cup 95 to prevent any contact between the patient and the cup 95. The liner 119 can be perforated to establish fluid communication between the base unit 103 and the tissue cavity 91. For example, one or more holes (e.g., opening 122 shown in FIG. 2) can be formed in the liner 119 using an instrument. In other embodiments, pre-formed portions of the liner 119 can be removed to form openings.

The liner 119 can remain securely coupled to the cup 95 throughout one or more treatment protocols, which may include repeatedly drawing tissue into the applicator, applying the applicator to multiple treatment sites, etc. Liner assemblies can include films, sheets, sleeves, or other components suitable for defining an interface surface to prevent direct contact between surfaces of the applicator and the subject's skin to reduce the likelihood of cross-contamination between patients, minimize cleaning requirements, etc. Exemplary protective liners can be sheets, sleeves, or other components constructed from latex, rubber, nylon, Kevlar®, or other substantially impermeable or semi-permeable material. For example, the liner 119 can be a latex sheet coated with a pressure-sensitive adhesive. Further details regarding a patient protection device may be found in U.S. Patent Publication No. 2008/0077201. In some procedures, a liner or protective sleeve may be positioned between an absorbent and the applicator to shield the applicator and to provide a sanitary barrier that is, in some embodiments, inexpensive and thus disposable. After installing the liner assembly 117, gel traps, filters, valves, and other components can be installed to keep applied substances (e.g., coupling gels, cryoprotectants, etc.) from being sucked into and/or through the base unit 103. In some embodiments, the liner 119 is configured to allow air to pass when drawing a vacuum and to restrict passage of a gel.

FIGS. 18-21 show applicators in accordance with various embodiments of the present technology. The description of the applicators in connection with FIGS. 1-17F applies equally to the applicators of FIGS. 18-21 unless indicated otherwise. For example, liner assemblies discussed in connection with FIG. 1-17F can be used with the applicators of FIG. 18-21. In some treatments, the liner assemblies can be eliminated by, for example, incorporating sealing members (e.g., gaskets) into contoured heads or using separate sealing members.

Figure 18:
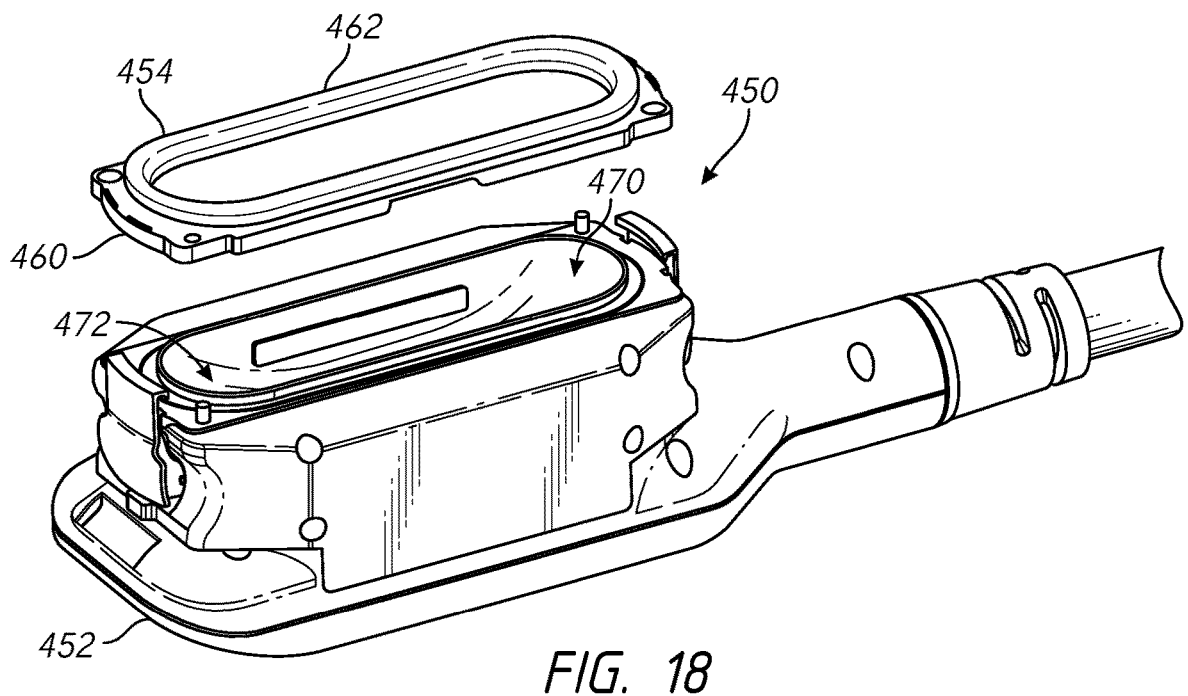
FIG. 18 is an exploded isometric view of an applicator in accordance with another embodiment of the disclosed technology.
Figure 19:
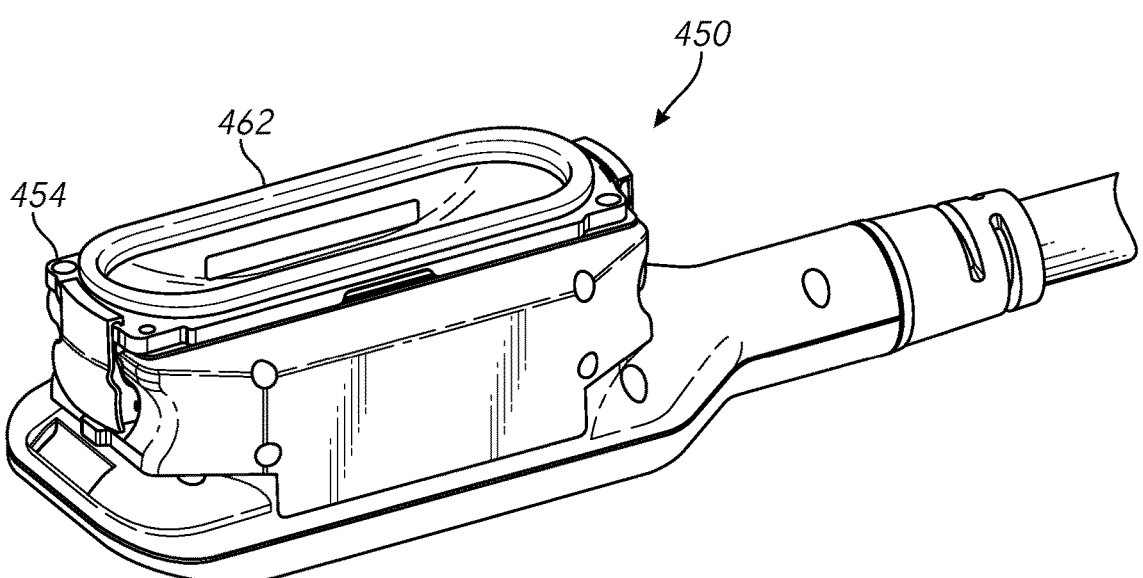
FIG. 19 is an isometric view of the applicator of FIG. 18.

FIG. 18 is an exploded isometric view of an applicator 450 with a base unit 452 and a contoured head 454. FIG. 19 shows the contoured head 454 installed on the base unit 452. The applicator 450 can be used with or without a liner assembly. The head 454 can include a mounting base or frame 460 and a contoured mouth 462. The contoured mouth 462 can have a generally rounded rectangular shape (as viewed from above) generally similar to the shape of an entrance 470 of a tissue-receiving cavity 472. The contoured mouth 462 has a generally uniform height for application to a generally flat treatment site (e.g., along a subject's back, flat abdomen section, etc.). In other embodiments, the contoured mouth 462 has a lip that is curved with respect to the length of the lip or a varying height for application to non-planar treatment sites.

Figure 20:
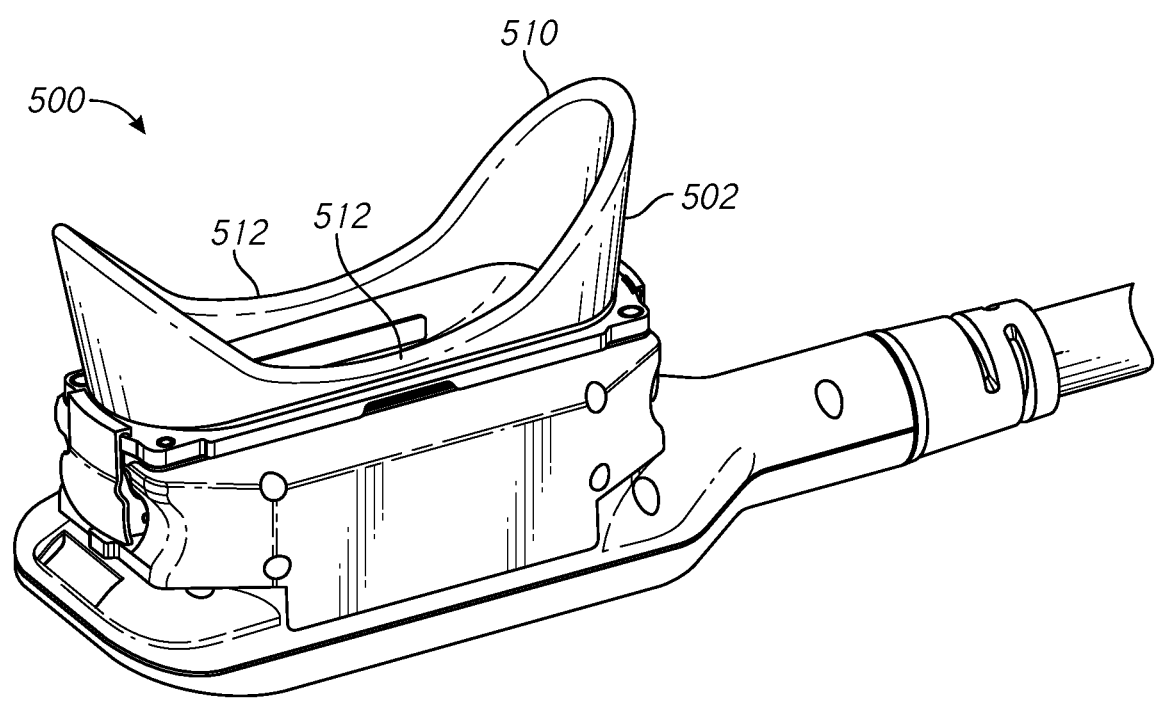
FIG. 20 is an isometric view of an applicator in accordance with another embodiment of the disclosed technology.
Figure 21:
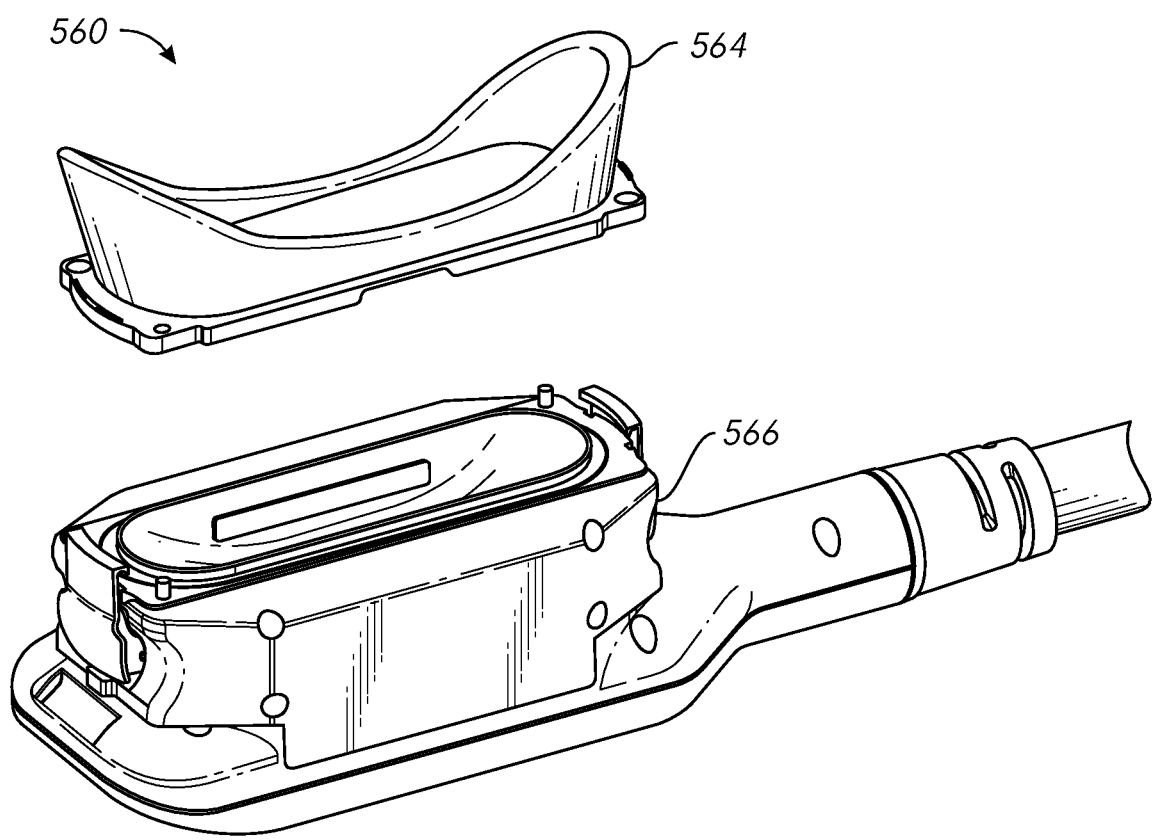
FIG. 21 is an exploded isometric view of an applicator in accordance with another embodiment of the disclosed technology.

FIG. 20 is isometric view of an applicator 500 with a contoured head 502 for treating a highly contoured treatment site. The contoured head 502 has a flexible mouth 510 with curved lips 512 suitable for circumferentially surrounding a patient's thigh, hip, etc. The curvature of the flexible mouth 510 can be selected to closely match the curvature of the treatment site. For example, FIG. 21 is an exploded isometric view of an applicator 560 with a contoured head 564 and a base unit 566. The contoured head 564 can be applied to a treatment site having a curvature less than the curvature at treatment sites suitable for the contoured head 502 of FIG. 20.

The geometries of the contoured heads can be selected to conform to a contour of a cutaneous layer. The sides, waistline, and other features of the contoured heads can be selected to facilitate conformation of heads to the contours of individual target areas. For example, the shape of a typical human torso may vary between having a relative large radius of curvature, e.g., on the stomach or back, and having a relatively small radius of curvature, e.g., on the abdominal sides. Moreover, the size of a head having an approximately consistent curvature may vary. Accordingly, an advantage of the present disclosure is the capability to provide flexible contour regions, lips, non-planar frames, etc. with various geometries, e.g., shapes and sizes, to suitably conform to the cutaneous contours of individual target areas. The heads may be fitted to individual lipid-rich cell deposits to achieve an approximately air-tight seal, achieve the vacuum pressure for drawing tissue into an interior cavity for treatment, maintain suction to hold the tissue, massage tissue (e.g., by altering pressure levels), and use little or no force to maintain contact between an applicator and a patient.

Attaching heads to base units creates specific contours to approximately fit tissue to be treated. The heads can be attached and detached in a plurality of combinations to achieve a desired contour for a treatment. Accordingly, a single base unit and/or umbilical cable may be combined with a set of interchangeable heads to form a wide variety of contours for treating different lipid-rich cell deposits in a cost effective manner. Further, a practitioner performing the treatment can demonstrate their expertise to the patient by tailoring the applicator contour to the specific body parts being treated. In this manner, the patient understands that their treatment is customized to their body for better comfort and for better treatment results.

Figure 22:
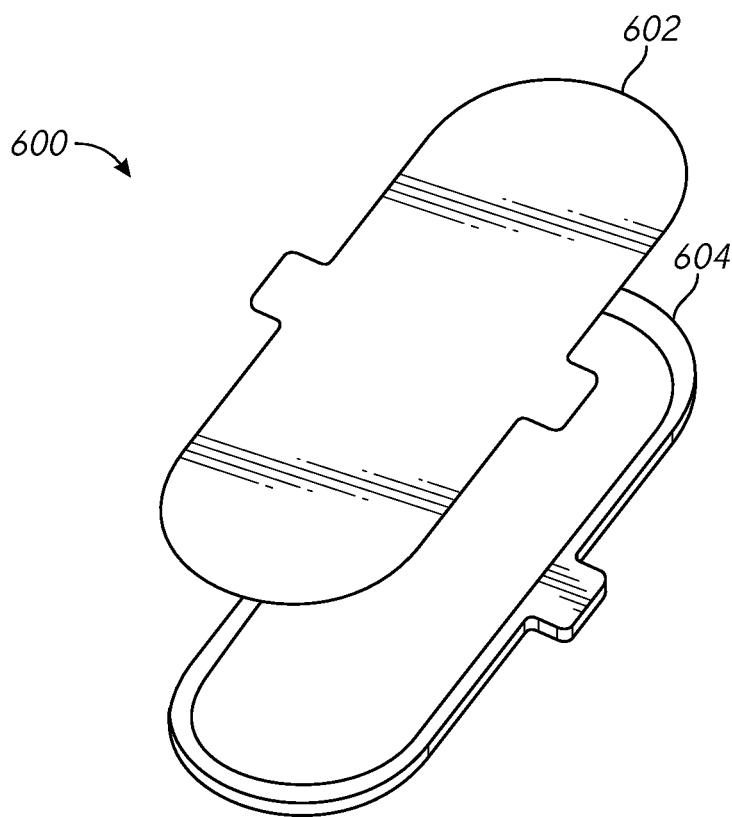
FIGS. 22 and 23 are exploded isometric views of multi-piece components in accordance with embodiments of the disclosed technology.

FIG. 22 is an exploded isometric view of a liner assembly 600 in accordance with embodiments of the present technology. The description of the linear assemblies discussed in connection with FIGS. 1-17F applies equally to the linear assembly 600 unless indicated otherwise. The liner assembly 600 can include a monolayer or multilayer liner 602 and a gasket 604. In some monolayer embodiments, an adhesive (e.g., flowable adhesive, adhesive sheet, etc.) can be applied to the conductive cup. The liner assembly 600 can then be installed on the base unit. In other embodiments, adhesive can be applied directly to the liner 602 before, during, and/or after installation of the liner assembly 600. The gasket 604 can be welded (e.g., sonically welded), bonded, adhered, or otherwise coupled to the liner 602.

Figure 23:
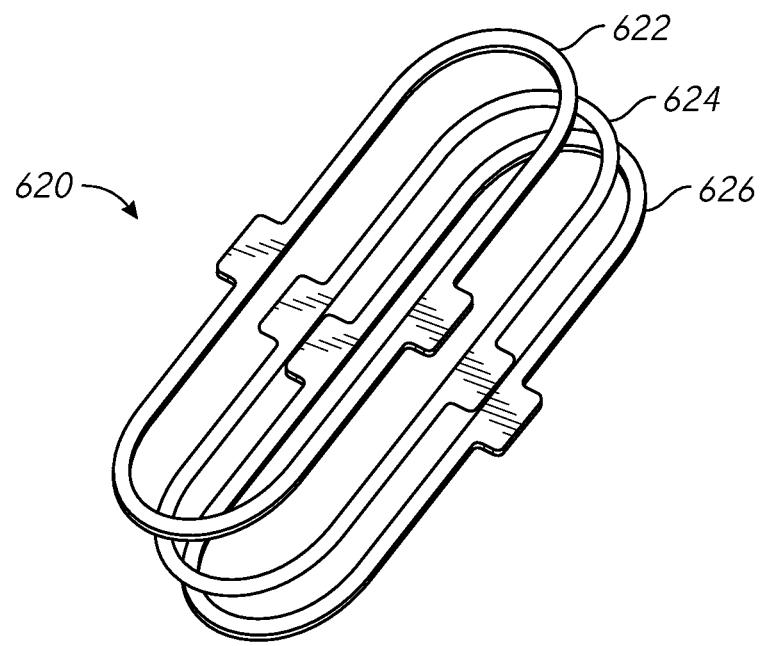

FIG. 23 is an isometric view of a sealing member 620 that can include a gasket 622, an adhesive layer 624, and a gasket 626. The gasket 622 can be a mono or multilayer structure permanently or temporarily coupled to the gasket 626 via the adhesive layer 624. The sealing member 620 can be used to provide sealing capability. In some embodiments, a separate liner or patient protection device can with an application having the sealing member 620. The liners disclosed herein can be eliminated to provide sealing members (or gaskets) capable of forming seals between various components.

Embodiments according to the present disclosure may provide one or more additional seal advantages. For example, the size, shapes, and other physical properties of the base units, liner assemblies, sealing members, gaskets, contoured heads, and components of the applicators may be selected to accommodate a heat removal sources (e.g., thermal devices, cooling devices, etc.) that may be used/reused with individual applicators. Modifications to flexible portions of individual applicators may enable the use of a standard heat removal source and accommodate different contours of individual cutaneous layers. In turn, this may make it possible to reuse base units, sealing members, liners, and/or contoured heads for different treatments. The rigid portions of the applicators (e.g., edge or mounting region of base unit), which are relatively stiff with respect to the flexible portions, provide an attachment point for heat removal sources that may resist bowing into the interior cavity and possibly separating from the heat removal sources when a vacuum (including a partial vacuum) is drawn in the applicators. Disposing temperature sensors inside the applicators, along temperature-controlled surfaces, within contoured heads, along liner assemblies, etc. may more accurately measure the temperature of skin surface, subcutaneous tissue, and so forth. The flexible portions of the applicator (e.g., flexible mouth) also allows some compliance to different subject body contours or geometries.

E. Treatment Methods

Figure 24:
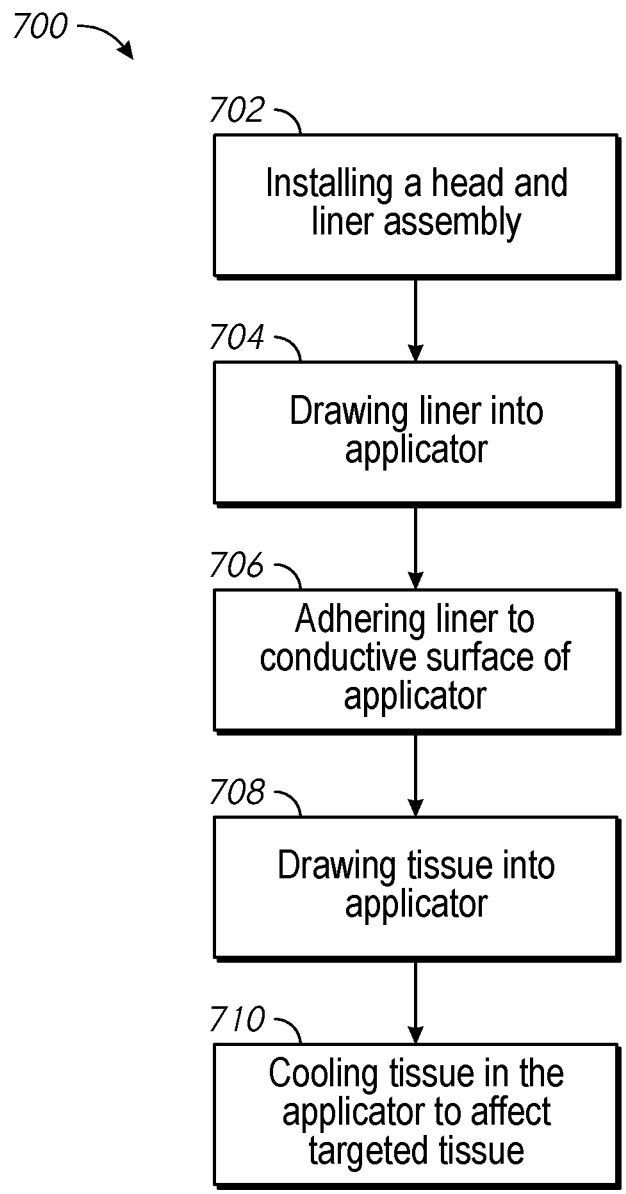
FIG. 24 is a flowchart of a method for treating a subject in accordance with embodiments of the disclosed technology.

FIG. 24 is a flowchart of a method 700 for treating a subject in accordance with embodiments of the disclosed technology. Generally, an applicator can be configured by installing a head, sealing member, or other components on a base unit. The applicator can then be applied to the treatment site to cool/heat targeted tissue. The sealing member can be a standalone component or part of a liner assembly. Details of the method 700 are discussed in connection the embodiments shown in FIGS. 1-17F.

At block 702, the contoured head 92 and/or liner assembly 117 can be installed. As discussed in connection with FIGS. 12-14, the liner assembly 117 can be clamped between the frame 150 and base unit 103. The base unit 103 can obtain information about the contoured head 92 to determine, for example, treatment protocols. For example, the base unit 103 can obtain information via the sensors 300a, 300b (FIG. 11) functioning as communication devices that communicate information. The information can be provided to the manufacturer so that the manufacturer can track usage of various heads and track any failures or treatment malfunctions or treatment parameters and treatment results associated with any head to better track and improve product performance.

At block 704, the liner 119 can be applied to the conductive surface 161 of the cup 95 as discussed in connection with FIGS. 17A-17F. As shown in FIG. 17E, the liner 119 can extend across the entrance of the tissue-receiving cavity 91 to from a closed chamber. A vacuum can be drawn in closed chamber to pull the liner 119 against the cup 95.

At block 706, the liner 119 can be adhered to the conductive surface 161 and perforated to allow a vacuum to be drawn in the tissue-receiving cavity 91. Once the liner 119 overlays the cup 95, the applicator 102 can be applied to the treatment site.

At block 708, the mouth 152 can be held against the subject while the pressurization device 123 (FIG. 1) operates to urge tissue into the applicator 102. The mouth 152 (FIG. 8) and sidewalls 260a, 260b (FIG. 6) can be splayed out to conformably suck tissue into the tissue-receiving cavity 91. The pressure level can be selected to partially or completely fill the tissue-receiving cavity 91 with tissue. If the vacuum level is too low, tissue will not be drawn adequately into the cavity 91. The vacuum level can be increase to reduce or eliminate gaps between the skin surface and the liner 119. If the pressure level is too high, undesirable discomfort to the patient and/or tissue damage could occur. The vacuum level can be selected to comfortably pull the tissue into contact with the desired area of the applicator 102, and the skin and underlying tissue can be pulled away from the subject's body which can assist in cooling underlying tissue by, e.g., lengthening the distance between targeted subcutaneous fat and the muscle tissue.

In some treatments, tissue can be drawn into the tissue-receiving cavity 91 such that substantially all of the skin surface within the cavity 91 overlies the conductive surface 161. For example, 90%, 95%, 95%, or more of the surface area of the skin located in the cavity 91 can overlie the conductive surface 161. The size of the vacuum ports can be increased or decreased to decrease or increase the area of the conductive surface 161.

After a sufficient amount of tissue fills most or all of the cavity 91, the tissue is cooled/heated. The pressure level (e.g., vacuum level) can be controlled to comfortably hold the tissue within the applicator 102. During cooling/heating, the tissue can fill substantially the entire cavity 91. In various embodiments, the tissue can occupy at least 70%, 80%, 90%, or 95% of the volume of the cavity 91 to avoid or minimize air pockets that may impair heat transfer. Blood flow through the dermis and subcutaneous layer of the tissue is a heat source that counteracts the cooling of the targeted tissue (e.g., sub-dermal fat). If the blood flow is not reduced, cooling the subcutaneous tissues would require not only removing the specific heat of the tissues but also that of the blood circulating through the tissues. Thus, reducing or eliminating blood flow through the tissue by increasing the vacuum can improve the efficiency of cooling and avoid excessive heat loss from the dermis and epidermis.

The conductive surface 161 can thermally contact an area of the subject's skin equal to or less than about 20 $cm^2$, 40 $cm^2$, 80 $cm^2$, 100 $cm^2$, 140 $cm^2$, 160 $cm^2$, 180 $cm^2$, 200 $cm^2$, 300 $cm^2$, or other suitable area. For example, the temperature-controlled surface area of the cooling cup 95 can be, for example, equal to or less than 20 $cm^2$, 40 $cm^2$, 80 $cm^2$, 100 $cm^2$, 140 $cm^2$, 160 $cm^2$, 180 $cm^2$, 200 $cm^2$, 300 $cm^2$, or another suitable area. The temperature-controlled conductive surface 161 can be cooled to a temperature equal to or less than a selected temperature (e.g., 5° C., 0° C., -2° C., -5° C., -7° C., -10° C., -15° C., -20° C., -25° C., etc.) to cool most of the skin surface of the retained tissue. In one embodiment, most of a heat-exchanging surface 161 can be cooled to a temperature equal to or less than about 0° C., -2° C., -5° C., -10° C., or -15° C.

At block 710, the applicator 102 can hold the tissue in thermal contact with the liner assembly 117 and cup 95. Heat from the tissue can be conductively transferred through the liner assembly 117 to the cooled surface 161 such that heat flows across substantially all of the applicator/skin interface. The cup 95 can be designed for rapid cooling and/or heating to, for example, reduce treatment times and/or produce generally flat temperature profiles over the heat-exchanging surface 161 or a portion thereof. Because the subject's body heat can be rapidly conducted to the cup 95, the cooled skin can be kept at a generally flat temperature profile (e.g., ±3° C. of a target temperature) even though regions of the skin, or underlying tissue, may experience different amounts of blood flow. Because non-lipid-rich cells usually can withstand colder temperatures better than lipid-rich cells, the subcutaneous lipid-rich cells can be injured selectively while maintaining the non-lipid-rich cells (e.g., non-lipid-rich cells in the dermis and epidermis). Accordingly, subcutaneous lipid-rich cells in a subcutaneous layer can be cooled an amount sufficient to be biologically effective in affecting (e.g., damaging and/or reducing) such lipid-rich cells without affecting non-target cells to the same or greater extent.

In contrast to invasive procedures in which coolant is injected directly into targeted tissue, each of the sidewalls 260a, 260b and bottom 262 (FIG. 7) can conductively cool tissue to produce a desired temperature in target tissue without bruising, pain, or other problems caused by injections and perfusion of injected fluid. For example, perfusion of injected fluid can affect the thermal characteristics of the treatment site and result in undesired temperature profiles. As such, the non-invasive conductive cooling provided by the applicator 102 can be more accurate than invasive procedures that rely on injecting fluids. Targeted tissue can be cooled from about -20° C. to about 10° C., from about 0° C. to about 20° C., from about -15° C. to about 5° C., from about −5° C. to about 15° C., or from about −10° C. to about 0° C. In one embodiment, liner 117 can be kept at a temperature less than about 0° C. to extract heat from subcutaneous lipid-rich cells such that those cells are selectively reduced or damaged.

Although the illustrated applicator 102 of FIG. 1 is positioned along the hips, applicators can also be positioned to treat tissue at the thighs, buttock, abdomen, submandibular region, neck region, or other target regions. The applicator 102 can reduce localized adipose tissue along the abdomen, hips, submental region, or the like. In procedures for reducing a double chin, the applicator 102 can sized and then aligned with and placed generally at the submental region (i.e., the submental triangle). It will be appreciated that the applicator 102 can be placed at other locations along the patient's body and the orientation of the applicator 102 can be selected to facilitate a relatively close fit.

Other elements, materials, components (e.g., gel pads, absorbents, etc.) can be located between the skin and the applicators. U.S. Pub. No. 2007/0255362 and U.S. Patent Publication No. 2008/0077201 and U.S. application Ser. No. 14/610,807 disclose components, materials (e.g., coupling gels, cryoprotectants, compositions, etc.), and elements (e.g., coupling devices, liners/protective sleeves, absorbents, etc.) that can be placed between the skin and the applicator.

The control module 106 (FIG. 1) can automatically perform various acts. For example, upon installation of the head, the control module 106 can automatically select a pressurization level suitable for drawing the liner into the base unit. Once the liner has been applied to the conductive cup, the control module 106 can notify a user to, for example, inspect the liner, apply the applicator, or perform another task.

The control module 106 (FIG. 1) can then command the pressurization device 123 to draw tissue into the applicator 102. The control module 106 can notify the operator that the applicator 102 is ready for treatment based on sensor reading. The operator can inspect the applicator 102 and can begin treatment using the control module 106.

It will be appreciated that while a region of the body has been cooled or heated to the target temperature, in actuality that region of the body may be close but not equal to the target temperature, e.g., because of the body's natural heating and cooling variations. Thus, although the applicator 102 may attempt to heat or cool the target tissue to the target temperature or to provide a target heat flux, the sensors 268 (FIG. 6) may measure a sufficiently close temperature or heat flux. If the target temperature or heat flux has not been reached, operation of the cooling unit can be adjusted to change the heat flux to maintain the target temperature or "set-point" selectively to affect targeted tissue. When the prescribed segment duration expires, the next treatment profile segment can be performed.

The treatment procedures disclosed herein can also involve use of cryoprotectant between the applicator and skin. The cryoprotectant can be a freezing point temperature depressant that may additionally include a thickening agent, a pH buffer, a humectant, a surfactant, and/or other additives. The temperature depressant may include, for example, polypropylene glycol (PPG), polyethylene glycol (PEG), dimethyl sulfoxide (DMSO), or other suitable alcohol compounds. In a particular embodiment, a cryoprotectant may include about 30% polypropylene glycol, about 30% glycerin (a humectant), and about 40% ethanol. In another embodiment, a cryoprotectant may include about 40% propylene glycol, about 0.8% hydroxyethylcellulose (a thickening agent), and about 59.2% water. In a further embodiment, a cryoprotectant may include about 50% polypropylene glycol, about 40% glycerin, and about 10% ethanol. Other cryoprotectants or agents can also be used and can be carried by a cotton pad or other element. U.S. application Ser. No. 14/610,807 is incorporated by reference in its entirety and discloses various compositions that can be used as cryoprotectants.

It may take a few days to a few weeks, or longer, for the adipocytes to break down and be absorbed. A significant decrease in fat thickness may occur gradually over 1-3 months following treatment. Additional treatments can be performed until a desired result is achieved. For example, one or more treatments can be performed to substantially reduce (e.g., visibly reduce) or eliminate targeted tissue.

F. Computing Environments

Figure 25:
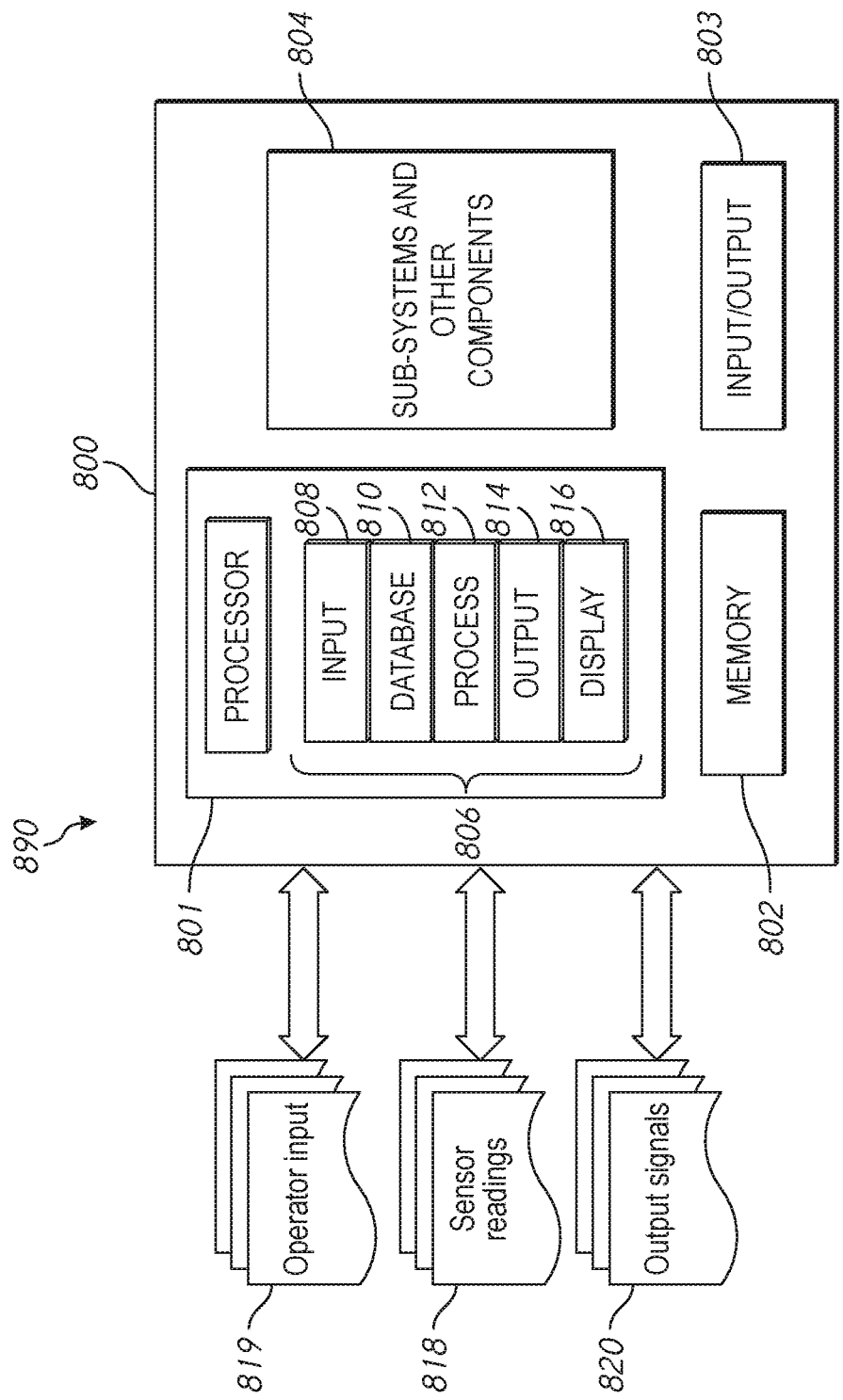
FIG. 25 is a schematic block diagram illustrating subcomponents of a controller in accordance with an embodiment of the technology.

FIG. 25 is a schematic block diagram illustrating subcomponents of a controller in accordance with an embodiment of the disclosure. The controller can be part of the control module 106 (FIG. 1). For example, the controller 790 can be the controller 114 of FIG. 1 or can be incorporated into the applicators or other components disclosed herein. The controller 790 can include a computing device 800 having a processor 801, a memory 802, input/output devices 803, and/or subsystems and other components 804. The computing device 800 can perform any of a wide variety of computing processing, storage, sensing, imaging, and/or other functions. Components of the computing device 800 may be housed in a single unit or distributed over multiple, interconnected units (e.g., though a communications network). The components of the computing device 800 can accordingly include local and/or remote memory storage devices and any of a wide variety of computer-readable media.

As illustrated in FIG. 25, the processor 801 can include a plurality of functional modules 806, such as software modules, for execution by the processor 801. The various implementations of source code (i.e., in a conventional programming language) can be stored on a computer-readable storage medium or can be embodied on a transmission medium in a carrier wave. The modules 806 of the processor can include an input module 808, a database module 810, a process module 812, an output module 814, and, optionally, a display module 816.

In operation, the input module 808 accepts an operator input 819 via the one or more input devices, and communicates the accepted information or selections to other components for further processing. The database module 810 organizes records, including patient records, treatment data sets, treatment profiles and operating records and other operator activities, and facilitates storing and retrieving of these records to and from a data storage device (e.g., internal memory 802, an external database, etc.). Any type of database organization can be utilized, including a flat file system, hierarchical database, relational database, distributed database, etc.

In the illustrated example, the process module 812 can generate control variables based on sensor readings 818 from sensors and/or other data sources, and the output module 814 can communicate operator input to external computing devices and control variables to the controller. The display module 816 can be configured to convert and transmit processing parameters, sensor readings 818, output signals 820, input data, treatment profiles and prescribed operational parameters through one or more connected display devices, such as a display screen 118 (FIG. 1), printer, speaker system, etc.

In various embodiments, the processor 801 can be a standard central processing unit or a secure processor. Secure processors can be special-purpose processors (e.g., reduced instruction set processor) that can withstand sophisticated attacks that attempt to extract data or programming logic. The secure processors may not have debugging pins that enable an external debugger to monitor the secure processor's execution or registers. In other embodiments, the system may employ a secure field programmable gate array, a smartcard, or other secure devices.

The memory 802 can be standard memory, secure memory, or a combination of both memory types. By employing a secure processor and/or secure memory, the system can ensure that data and instructions are both highly secure and sensitive operations such as decryption are shielded from observation. In various embodiments, the memory 802 can be flash memory, secure serial EEPROM, secure field programmable gate array, or secure application-specific integrated circuit. The memory 802 can store instructions for causing the applicators to cool/heat tissue, pressurization devices to draw a vacuum, or other acts disclosed herein. In one embodiment, the memory 802 stores instructions executable by the controller 790 for the thermal device to sufficiently cool conductive cups disclosed herein such that submental vacuum applicators non-invasively cool the subcutaneous lipid-rich cells to a desired temperature, such as a temperature less than about 0° C. In some embodiments, the memory 802 can contain liner installation or draw instructions for causing the liner to drawn into a conductive cup, tissue draw instructions for causing the applicator to draw tissue into the applicator, treatment instructions for heating/cooling tissue, tissue release instructions for releasing tissue, and instructions for monitoring treatment. For example, the liner installation or draw instructions can be executed by the controller 790 to command the pressurization device 123 to suck the liner against a conductive surface of the conductive cup.

The input/output device 118 can include, without limitation, a touchscreen, a keyboard, a mouse, a stylus, a push button, a switch, a potentiometer, a scanner, an audio component such as a microphone, or any other device suitable for accepting user input and can also include one or more video monitor, a medium reader, an audio device such as a speaker, any combination thereof, and any other device or devices suitable for providing user feedback. For example, if an applicator moves an undesirable amount during a treatment session, the input/output device 803 can alert the subject and/or operator via an audible alarm. The input/output device 118 can be a touch screen that functions as both an input device and an output device. The control panel can include visual indicator devices or controls (e.g., indicator lights, numerical displays, etc.) and/or audio indicator devices or controls. The control panel may be a component separate from the input/output device 118 and/or output device 120, may be integrated applicators, may be partially integrated with one or more of the devices, may be in another location, and so on. In alternative embodiments, the controller 114 can be contained in, attached to, or integrated with the applicators. Further details with respect to components and/or operation of applicators, control modules (e.g., treatment units), and other components may be found in commonly-assigned U.S. Patent Publication No. 2008/0287839.

The controller 790 can include any processor, Programmable Logic Controller, Distributed Control System, secure processor, and the like. A secure processor can be implemented as an integrated circuit with access-controlled physical interfaces; tamper resistant containment; means of detecting and responding to physical tampering; secure storage; and shielded execution of computer-executable instructions. Some secure processors also provide cryptographic accelerator circuitry. Suitable computing environments and other computing devices and user interfaces are described in commonly assigned U.S. Pat. No. 8,275,442, entitled "TREATMENT PLANNING SYSTEMS AND METHODS FOR BODY CONTOURING APPLICATIONS," which is incorporated herein in its entirety by reference.

G. Conclusion

The treatment systems, applicators, and methods of treatment can be used reduce adipose tissue or treat subcutaneous tissue, acne, hyperhidrosis, wrinkles, structures (e.g., structures in the epidermis, dermis, subcutaneous fat, muscle, nerve tissue, etc.), and so on. Systems, components, and techniques for reducing subcutaneous adipose tissue are disclosed in U.S. Pat. No. 7,367,341 titled "METHODS AND DEVICES FOR SELECTIVE DISRUPTION OF FATTY TISSUE BY CONTROLLED COOLING" to Anderson et al., U.S. Patent Publication No. US 2005/0251120 titled "METHODS AND DEVICES FOR DETECTION AND CONTROL OF SELECTIVE DISRUPTION OF FATTY TISSUE BY CONTROLLED COOLING" to Anderson et al., and U.S. Patent Publication No. 2007/0255362 titled "CRYOPROTECTANT FOR USE WITH A TREATMENT DEVICE FOR IMPROVED COOLING OF SUBCUTANEOUS LIPID-RICH CELLS," the disclosures of which are incorporated herein by reference in their entireties. Vacuum applicators can stretch, stress, and/or mechanically alter skin to increase damage and fibrosis in the skin, affect glands, control freeze events (including initiating freeze events), etc. Methods for cooling tissue and related devices and systems in accordance with embodiments of the present invention can at least partially address one or more problems associated with conventional technologies as discussed above and/or other problems whether or not such problems are stated herein.

Unless the context clearly requires otherwise, throughout the description, the words "comprise," "comprising," and the like are to be construed in an inclusive sense as opposed to an exclusive or exhaustive sense; that is to say, in a sense of "including, but not limited to." Words using the singular or plural number also include the plural or singular number, respectively. Use of the word "or" in reference to a list of two or more items covers all of the following interpretations of the word: any of the items in the list, all of the items in the list, and any combination of the items in the list. Furthermore, the phrase "at least one of A, B, and C, etc." is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.).

Any patents, applications and other references, including any that may be listed in accompanying filing papers, are incorporated herein by reference. Aspects of the described technology can be modified, if necessary, to employ the systems, functions, and concepts of the various references described above to provide yet further embodiments. These and other changes can be made in light of the above Detailed Description. While the above description details certain embodiments and describes the best mode contemplated, no matter how detailed, various changes can be made. Implementation details may vary considerably, while still being encompassed by the technology disclosed herein. As noted above, particular terminology used when describing certain features or aspects of the technology should not be taken to imply that the terminology is being redefined herein to be restricted to any specific characteristics, features, or aspects of the technology with which that terminology is associated.

What is claimed is:

1. An apparatus for treating a subject's tissue, comprising: an applicator configured to cool and affect targeted tissue and including
    a base unit including a temperature-controlled cup having a conductive heat-exchanging surface defining a tissue-receiving cavity,
    a head removably coupleable to the base unit and including a contoured mouth,
    a sealing member being positionable between the head and the base unit to create a vacuum seal therebetween,
    latches located on opposite sides of the base unit and movable from unlocked positions to locked positions to pull the head toward the base unit such that the sealing member, which is positioned in a trench of the base unit, is compressed to form the vacuum seal, wherein the trench circumferentially surrounds an entrance of the tissue-receiving cavity, and
    a liner assembly having the sealing member and a liner coupled to the sealing member, wherein the liner is configured to extend across the entrance of the tissue receiving cavity when the sealing member is positioned between the head and the base unit;
  a controller programmed to command the applicator to draw a vacuum in the tissue-receiving cavity to pull the tissue into thermal contact with the conductive heat-exchanging surface; and
  a vacuum source fluidically coupled to the applicator and operable to cause the liner and tissue to be drawn to a bottom of the tissue-receiving cavity to bring the tissue into thermal contact with a portion of the conductive heat-exchanging surface at the bottom of the tissue-receiving cavity.

2. The apparatus of claim 1, wherein the controller is programmed to command the vacuum source to draw the tissue into thermal contact with the conductive heat-exchanging surface to eliminate air gaps between the tissue and the conductive heat-exchanging surface, and the controller containing instructions for causing a thermal device of the base unit to cool the temperature-controlled cup to non-invasively cool subcutaneous lipid-rich cells to a temperature less than about 0° C.

* * * * *